US012557990B2

(12) United States Patent
Wu et al.

(10) Patent No.: US 12,557,990 B2
(45) Date of Patent: Feb. 24, 2026

(54) BRADYKINESIA MOTION ANALYSIS FOR BEHAVIOR IDENTIFICATION BY DETERMINING MOTION CENTER AND VELOCITY FROM THE VIDEO FRAMES

(71) Applicant: Medtronic, Inc., Minneapolis, MN (US)

(72) Inventors: Jianping Wu, Medina, MN (US); Chih Lai, Woodbury, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1038 days.

(21) Appl. No.: 17/582,903

(22) Filed: Jan. 24, 2022

(65) Prior Publication Data

US 2022/0142513 A1 May 12, 2022

Related U.S. Application Data

(63) Continuation of application No. 14/104,057, filed on Dec. 12, 2013, now Pat. No. 11,229,364.

(Continued)

(51) Int. Cl.
*A61B 5/00* (2006.01)
*A61B 5/021* (2006.01)
(Continued)

(52) U.S. Cl.
CPC .......... *A61B 5/0077* (2013.01); *A61B 5/0022* (2013.01); *A61B 5/0036* (2018.08);
(Continued)

(58) Field of Classification Search
CPC ... A61B 5/0077; A61B 5/0022; A61B 5/0036; A61B 5/1114; A61B 5/1121;
(Continued)

(56) References Cited

U.S. PATENT DOCUMENTS 5,441,047 A   8/1995   David et al.
5,960,111 A   9/1999   Chen et al.
(Continued)

FOREIGN PATENT DOCUMENTS

WO   2012101093 A2   8/2012
WO   2013059227 A1   4/2013

OTHER PUBLICATIONS

Chang et al., "An automated form of video image analysis applied to classification of movement disorders," Journal of Disability and Rehabilitation, vol. 22, No. 1/2, Jan. 10, 2000, pp. 97-108.
(Continued)

*Primary Examiner* — Serkan Akar
(74) *Attorney, Agent, or Firm* — Shumaker & Sieffert, P.A.

(57) ABSTRACT

Devices, systems, and techniques for analyzing video information to objectively identify patient behavior are disclosed. A system may analyze obtained video information of patient motion during a period of time to track one or more anatomical regions through a plurality of frames of the video information and calculate one or more movement parameters of the one or more anatomical regions. The system may also compare the one or more movement parameters to respective criteria for each of a plurality of predetermined patient behaviors and identify the patient behaviors that occurred during the period of time. In some examples, a device may control therapy delivery according to the identified patient behaviors and/or sensed parameters previously calibrated based on the identified patient behaviors.

9 Claims, 30 Drawing Sheets

Related U.S. Application Data

(60) Provisional application No. 61/835,405, filed on Jun. 14, 2013.

(51) Int. Cl.

| | |
|---|---|
| *A61B 5/024* | (2006.01) |
| *A61B 5/08* | (2006.01) |
| *A61B 5/11* | (2006.01) |
| *A61B 5/318* | (2021.01) |
| *A61B 5/369* | (2021.01) |
| *A61B 5/389* | (2021.01) |
| *G06T 7/254* | (2017.01) |
| *G06T 7/262* | (2017.01) |
| *G16H 30/40* | (2018.01) |
| *A61N 1/05* | (2006.01) |
| *A61N 1/36* | (2006.01) |

(52) U.S. Cl.

CPC .......... *A61B 5/1114* (2013.01); *A61B 5/1121* (2013.01); *A61B 5/1128* (2013.01); *A61B 5/4082* (2013.01); *A61B 5/7246* (2013.01); *A61B 5/7257* (2013.01); *A61B 5/7264* (2013.01); *A61B 5/7282* (2013.01); *A61B 5/743* (2013.01); *G06T 7/254* (2017.01); *G06T 7/262* (2017.01); *G16H 30/40* (2018.01); *A61B 5/021* (2013.01); *A61B 5/024* (2013.01); *A61B 5/08* (2013.01); *A61B 5/1124* (2013.01); *A61B 5/318* (2021.01); *A61B 5/369* (2021.01); *A61B 5/389* (2021.01); *A61B 5/4803* (2013.01); *A61B 5/4809* (2013.01); *A61B 5/4839* (2013.01); *A61B 5/4848* (2013.01); *A61B 2576/00* (2013.01); *A61N 1/0534* (2013.01); *A61N 1/36067* (2013.01); *A61N 1/36135* (2013.01); *G06T 2207/10016* (2013.01); *G06T 2207/30196* (2013.01)

(58) Field of Classification Search

CPC ... A61B 5/1128; A61B 5/4082; A61B 5/7246; A61B 5/7257; A61B 5/7264; A61B 5/7282; A61B 5/743; A61B 5/021; A61B 5/024; A61B 5/08; A61B 5/1124; A61B 5/318; A61B 5/369; A61B 5/389; A61B 5/4803; A61B 5/4809; A61B 5/4839; A61B 5/4848; A61B 2576/00; G06T 7/254; G06T 7/262; G06T 2207/10016; G06T 2207/30196; G16H 30/40; G16H 50/20; G16H 40/67; A61N 1/0534; A61N 1/36067; A61N 1/36135

See application file for complete search history.

(56) References Cited

U.S. PATENT DOCUMENTS

| | | | |
|---|---|---|---|
| 7,519,431 | B2 | 4/2009 | Goetz et al. |
| 2002/0123673 | A1 | 9/2002 | Webb et al. |
| 2005/0124863 | A1 | 6/2005 | Cook |
| 2005/0163349 | A1 | 7/2005 | Brunner et al. |
| 2005/0234309 | A1 | 10/2005 | Klapper |
| 2007/0281892 | A1 | 12/2007 | Martin et al. |
| 2008/0033502 | A1 | 2/2008 | Harris et al. |
| 2008/0100438 | A1 | 5/2008 | Marrion et al. |
| 2008/0267447 | A1 | 10/2008 | Kelusky et al. |
| 2009/0062696 | A1* | 3/2009 | Nathan ............... A61B 5/1101 600/595 |
| 2009/0082641 | A1 | 3/2009 | Giftakis et al. |
| 2009/0099627 | A1 | 4/2009 | Molnar et al. |
| 2010/0049095 | A1 | 2/2010 | Bunn et al. |
| 2010/0159497 | A1 | 6/2010 | Kimia et al. |
| 2010/0162303 | A1 | 6/2010 | Cassanova |
| 2010/0168603 | A1 | 7/2010 | Himes |
| 2011/0102568 | A1 | 5/2011 | Bonnet |
| 2014/0153794 | A1 | 6/2014 | Varaklis et al. |
| 2014/0371544 | A1 | 12/2014 | Wu et al. |
| 2014/0371599 | A1 | 12/2014 | Wu et al. |
| 2015/0004581 | A1 | 1/2015 | Selman et al. |

OTHER PUBLICATIONS

Cho et al., "A Vision-based Analysis System for Gait Recognition in Patients with Parkinson's Disease," Expert Systetms with Applications, vol. 36(3), Apr. 2009, pp. 7033-7039.

International Preliminary Report on Patentability from International Application No. PCT/US2014/033412, dated Dec. 15, 2015, 8 pp.

International Search Report and Written Opinion of counterpart International Patent Application No. PCT/US2014/033412, mailed Jul. 21, 2014, 13 pp.

MedGadget, "System Allows for Brain Activity Mapping Without Patient Cooperation," MedGadget, retrieved from the internet http://www.medgadget.com/2013/06/system-allows-for-brain-activity-mapping-without-patient-cooperation.html, Jun. 7, 2013, 3pp.

Ruzicka et al., "Video as a Tool for Quantitative Analysis of Tremor and Bradykinesia," European Neurological Society, Jun. 10, 2012, 1 pp.

Shih et al., "Integrated digital image and accelerometer measurements of rat locomotor and vibratory behavior," Journal of Neuroscience Methods, vol. 166, Issue 1, Oct. 15, 2007, pp. 81-88.

Sonka et al., "Image Processing, Analysis, and Machine Vision, Chapter 15: Motion Analysis," Processing, Analysis, and Machine vision, PWS Publ, Jan. 1999, pp. 679-685.

Soran et al., "Tremor Detection Using Motion Filtering and SVM," University of Washington, Nov. 11-15, 2012, 4 pp.

Taha et al., "Motion Cue Analysis for Parkinsonian Gait Recognition," The Open Biomedical Engineering Journal, vol. 7(1), Jan. 15, 2013, pp. 1-8.

Taha Khan et al., "Motion Cue Analysis for Parkinsonian Gait Recognition," The Open Biomedical Engineering Journal, vol. 7(1), Jan. 15, 2013, pp. 1-8.

Uhrikova et al., "Periodic Motion Detection on Patient with Motion Disorders," Computer-Based Medical Systems, 21st IEEE International Symposium on CBMS '08, Jun. 2008, pp. 90-92.

Uhrikova et al., "TremAn: A tool for measuring tremor frequency from video sequences," Movement Disorders, vol. 25, No. 4, Mar. 2010, pp. 504-506.

Wu et al., "Video-Motion Detection for Objectively Quantifying Movements in Patients with Parkinson's Disease," Neuromodulation Research, Medtronic Inc., format: Microsoft Power Point, Jun. 17, 2013, 1 pp.

Wu et al., "Video-Motion Detection for Objectively Quantifying Movements in Patients with Parkinson's Disease," Neuromodulation Research, Medtronic Inc., format: Microsoft Word, Jun. 17, 2013, 2 pp.

Zhu et al., "Detecting Video Events Based on Action Recognition in Complex Scenes Using Spatio-Temporal Descriptor," Proceedings of the 17th ACM international conference on Multimedia, Oct. 19-24, 2009, pp. 165-174.

Prosecution History from U.S. Appl. No. 14/104,057, dated Jan. 22, 2016 through Nov. 12, 2021, 543 pp.

Prosecution History from U.S. Appl. No. 14/104,078, dated Dec. 13, 2013 through Oct. 8, 2020, 374 pp.

* cited by examiner

40

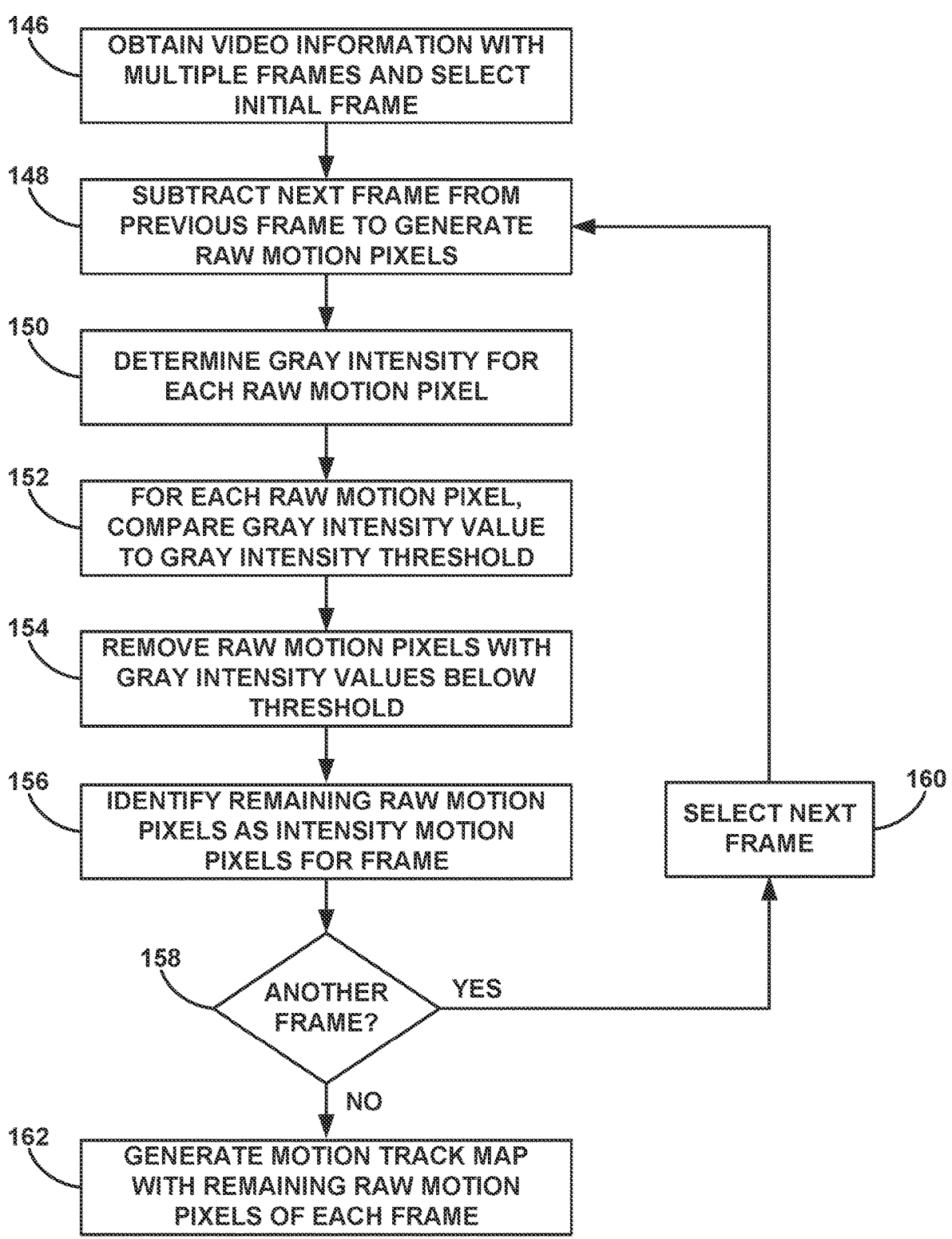

146 — OBTAIN VIDEO INFORMATION WITH MULTIPLE FRAMES AND SELECT INITIAL FRAME

148 — SUBTRACT NEXT FRAME FROM PREVIOUS FRAME TO GENERATE RAW MOTION PIXELS

150 — DETERMINE GRAY INTENSITY FOR EACH RAW MOTION PIXEL

152 — FOR EACH RAW MOTION PIXEL, COMPARE GRAY INTENSITY VALUE TO GRAY INTENSITY THRESHOLD

154 — REMOVE RAW MOTION PIXELS WITH GRAY INTENSITY VALUES BELOW THRESHOLD

156 — IDENTIFY REMAINING RAW MOTION PIXELS AS INTENSITY MOTION PIXELS FOR FRAME

160 — SELECT NEXT FRAME

158 — ANOTHER FRAME?

YES

NO

162 — GENERATE MOTION TRACK MAP WITH REMAINING RAW MOTION PIXELS OF EACH FRAME

FIG. 9

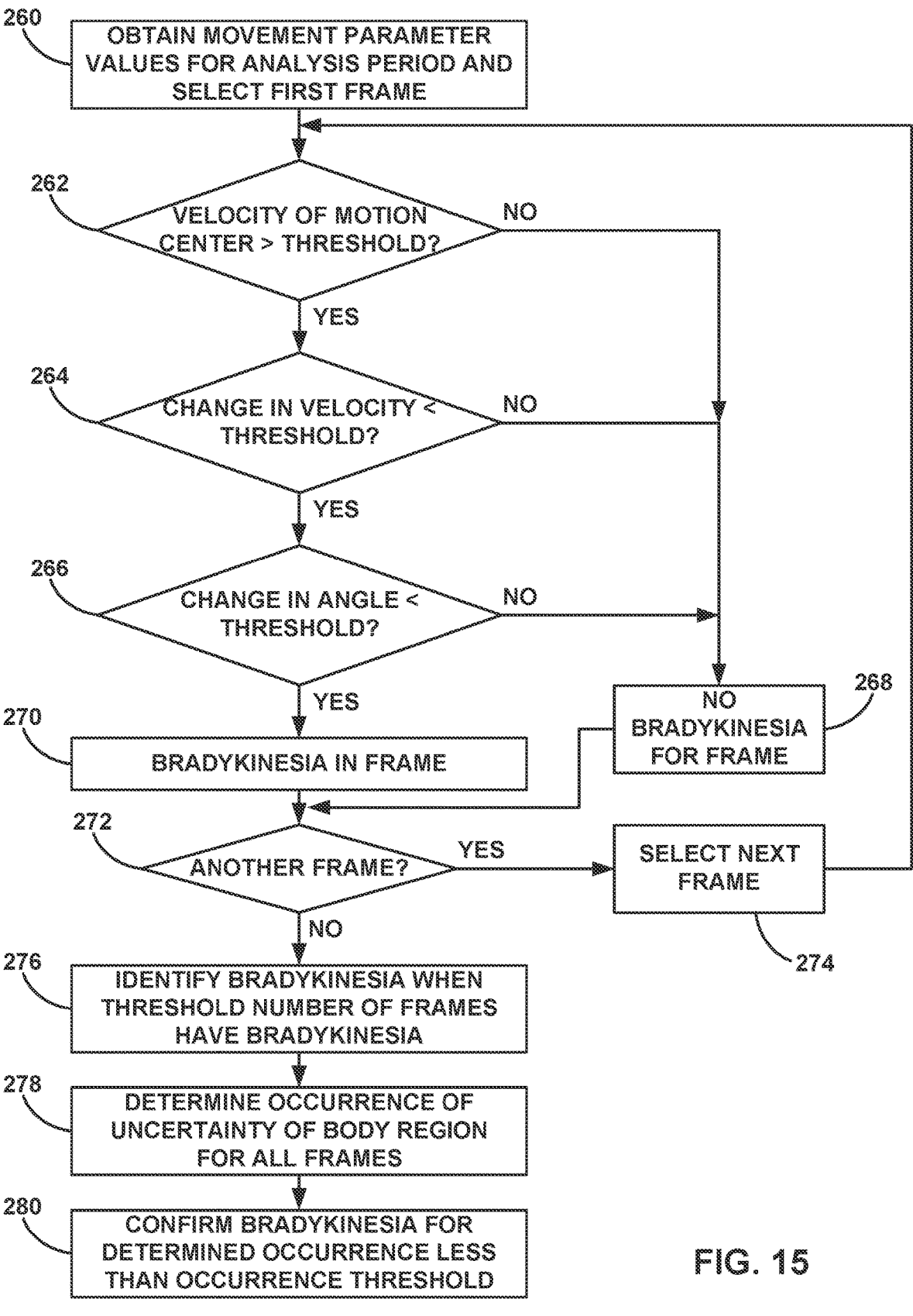

260 — OBTAIN MOVEMENT PARAMETER VALUES FOR ANALYSIS PERIOD AND SELECT FIRST FRAME

262 — VELOCITY OF MOTION CENTER > THRESHOLD?

NO

YES

264 — CHANGE IN VELOCITY < THRESHOLD?

NO

YES

266 — CHANGE IN ANGLE < THRESHOLD?

NO

YES

268 — NO BRADYKINESIA FOR FRAME

270 — BRADYKINESIA IN FRAME

272 — ANOTHER FRAME?

YES

NO

SELECT NEXT FRAME

274

276 — IDENTIFY BRADYKINESIA WHEN THRESHOLD NUMBER OF FRAMES HAVE BRADYKINESIA

278 — DETERMINE OCCURRENCE OF UNCERTAINTY OF BODY REGION FOR ALL FRAMES

280 — CONFIRM BRADYKINESIA FOR DETERMINED OCCURRENCE LESS THAN OCCURRENCE THRESHOLD

FIG. 15

312    OBTAIN VIDEO INFORMATION OF
PATIENT MOVEMENT

313    SCAN FRAMES OF VIDEO INFORMATION
FOR CANDIDATE FRAME FOR
SELECTION OF SAMPLE AREA OF THE
PATIENT'S HEAD

314    SELECT ONE OR MORE FRAMES FOR
USER DEFINITION OF A SAMPLE AREA
OF THE HEAD

315    RECEIVE SAMPLE AREA
IDENTIFICATION FOR THE FRAME(S)
FROM A USER

316    PERFORM ANALYSIS OF VIDEO
INFORMATION TO IDENTIFY PATIENT
BEHAVIOR

426C

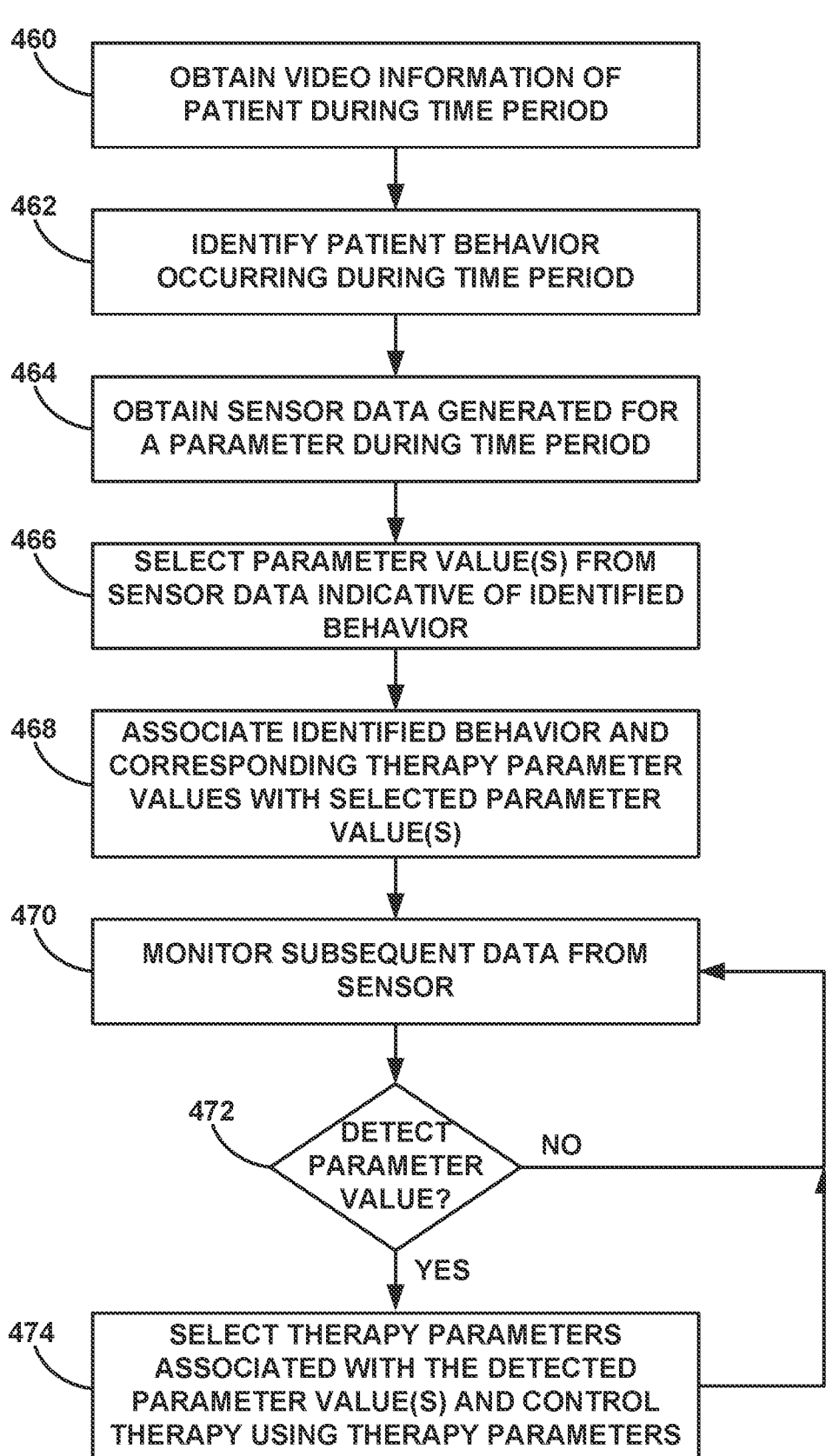

460 — OBTAIN VIDEO INFORMATION OF PATIENT DURING TIME PERIOD

462 — IDENTIFY PATIENT BEHAVIOR OCCURRING DURING TIME PERIOD

464 — OBTAIN SENSOR DATA GENERATED FOR A PARAMETER DURING TIME PERIOD

466 — SELECT PARAMETER VALUE(S) FROM SENSOR DATA INDICATIVE OF IDENTIFIED BEHAVIOR

468 — ASSOCIATE IDENTIFIED BEHAVIOR AND CORRESPONDING THERAPY PARAMETER VALUES WITH SELECTED PARAMETER VALUE(S)

470 — MONITOR SUBSEQUENT DATA FROM SENSOR

472 — DETECT PARAMETER VALUE?

NO

YES

474 — SELECT THERAPY PARAMETERS ASSOCIATED WITH THE DETECTED PARAMETER VALUE(S) AND CONTROL THERAPY USING THERAPY PARAMETERS

FIG. 29

BRADYKINESIA MOTION ANALYSIS FOR BEHAVIOR IDENTIFICATION BY DETERMINING MOTION CENTER AND VELOCITY FROM THE VIDEO FRAMES

This application is a continuation of U.S. patent application Ser. No. 14/104,057, to Wu, filed Dec. 12, 2013, and entitled "PATIENT MOTION ANALYSIS FOR BEHAVIOR IDENTIFICATION BASED ON VIDEO FRAMES WITH USER SELECTING THE HEAD AND TORSO FROM A FRAME", which claims the benefit of U.S. Provisional Patent Application No. 61/835,405, to Wu, filed Jun. 14, 2013, and entitled "MOTION ANALYSIS FOR BEHAVIOR IDENTIFICATION," both of which are incorporated herein by reference in their entirety.

TECHNICAL FIELD

The disclosure relates to motion analysis and, more particularly, identification of patient behavior using motion analysis.

BACKGROUND

Various diseases and conditions, such as movement disorders, can cause individuals to experience certain behaviors of movement. For example, a patient diagnosed with Parkinson's Disease may exhibit movement behaviors that may include one or more of tremor, rigidity, bradykinesia, and dyskinesia. Evaluation and identification of these patient behaviors is typically performed by a clinician viewing the movements of the patient. An example evaluation technique of Parkinson's Disease involves the use the Unified Parkinson's Disease Rating Scale, motor scale (mUPDRS). During this test, the clinician asks the patient to perform a routine of passive and active motor tasks, and the clinician provides scores to characterize the movements of the patient during these tasks.

A clinician may also treat a patient with a movement disorder using one or more therapies. Oral medication may be prescribed for some patients. Patients may also or alternatively be treated using drug delivery therapy and/or electrical stimulation therapy. Electrical stimulation therapy may include deep brain stimulation (DBS), although other types of electrical stimulation therapy may be employed for some patients.

SUMMARY

In general, the disclosure is directed to devices, systems, and techniques for analyzing video information to objectively identify patient behavior. A camera may generate video information that captures patient motion, or movement. A system may obtain and analyze the video information captured during a period of time to track one or more anatomical regions through a plurality of frames of the video information. The system may then calculate one or more movement parameters that characterize the motion of the one or more anatomical regions. The system may also compare the one or more movement parameters to respective criteria (e.g., one or more thresholds and/or ranges) for each of a plurality of predetermined patient behaviors and identify the patient behaviors that occurred during the period of time.

In addition, the system (and/or another device) may control the delivery of therapy according to the identified patient behaviors. In one example, the system may control therapy in response to identifying the patient behavior from the video information. In another example, the system may control therapy in response to a sensed value of a patient parameter that has been previously associated with (or calibrated by) the patient behaviors identified from the video information. In either case, controlling therapy may include at least one of selecting an oral medication dose, selecting a dose of medication from drug delivery therapy, and selecting a set of therapy parameters that defines electrical stimulation therapy.

In one example, the disclosure is directed to a method that includes obtaining video information of patient motion captured over a period of time, wherein the video information comprises a plurality of frames, receiving, with respect to one frame of the plurality of frames, a selection of a sample area representative of an anatomical region, analyzing, by one or more processors, each of the other plurality of frames for respective areas corresponding to the sample area, calculating, by the one or more processors, one or more movement parameters of the anatomical region during the period of time from at least one difference between the sample area and one or more respective areas of at least a subset of the plurality of frames, comparing, by the one or more processors, the one or more movement parameters of the period of time to respective criteria for each of a plurality of predetermined patient behaviors, and identifying, based on the comparison and by the one or more processors, each one of the predetermined patient behaviors that occurred during the period of time.

In another example, the disclosure is directed to a system that includes one or more processors configured to obtain video information of patient motion captured over a period of time, wherein the video information comprises a plurality of frames, receive, with respect to one frame of the plurality of frames, a selection of a sample area representative of an anatomical region, analyze each of the other plurality of frames for respective areas corresponding to the sample area, calculate one or more movement parameters of the anatomical region during the period of time from at least one difference between the sample area and one or more respective areas of at least a subset of the plurality of frames, compare the one or more movement parameters of the period of time to respective criteria for each of a plurality of predetermined patient behaviors, and identify, based on the comparison, each one of the predetermined patient behaviors that occurred during the period of time.

In another example, the disclosure is directed to a computer-readable storage medium that includes instructions that cause one or more processors to obtain video information of patient motion captured over a period of time, wherein the video information comprises a plurality of frames, receive, with respect to one frame of the plurality of frames, a selection of a sample area representative of an anatomical region, analyze each of the other plurality of frames for respective areas corresponding to the sample area, calculate one or more movement parameters of the anatomical region during the period of time from at least one difference between the sample area and one or more respective areas of at least a subset of the plurality of frames, compare the one or more movement parameters of the period of time to respective criteria for each of a plurality of predetermined patient behaviors, and identify, based on the comparison, each one of the predetermined patient behaviors that occurred during the period of time.

In another example, the disclosure is directed to a method that includes receiving, from a computing device, an indication of a patient behavior for a period of time, wherein the patient behavior is determined by the computing device from video information captured during the period of time, determining, based on the indication of the patient behavior and by one or more processors, a therapy to be delivered to the patient, and outputting the determination for at least one of delivery of the therapy to the patient and display to the user.

In another example, the disclosure is directed to a system that includes one or more processors configured to, receive, from a computing device, an indication of a patient behavior for a period of time, wherein the patient behavior is determined by the computing device from video information captured during the period of time, determine, based on the indication of the patient behavior, a therapy to be delivered to the patient, and output the determination for at least one of delivery of the therapy to the patient and display to the user.

In another example, the disclosure is directed to a computer-readable storage medium that includes instructions that cause one or more processors to receive, from a computing device, an indication of a patient behavior for a period of time, wherein the patient behavior is determined by the computing device from video information captured during the period of time, determine, based on the indication of the patient behavior, a therapy to be delivered to the patient, and output the determination for at least one of delivery of the therapy to the patient and display to the user.

The details of one or more example are set forth in the accompanying drawings and the description below. Other features, objects, and advantages will be apparent from the description and drawings, and from the claims.

BRIEF DESCRIPTION OF DRAWINGS

FIG. 9 is a flow diagram that illustrates an example process for filtering raw motion pixels from noise in the video information.

FIG. 15 is a flow diagram that illustrates an example process for identifying bradykinesia in a patient.

FIG. 29 is a flow diagram illustrating an example process for associating sensed patient parameter values with patient behavior identified from video information.

DETAILED DESCRIPTION

Figure 1:
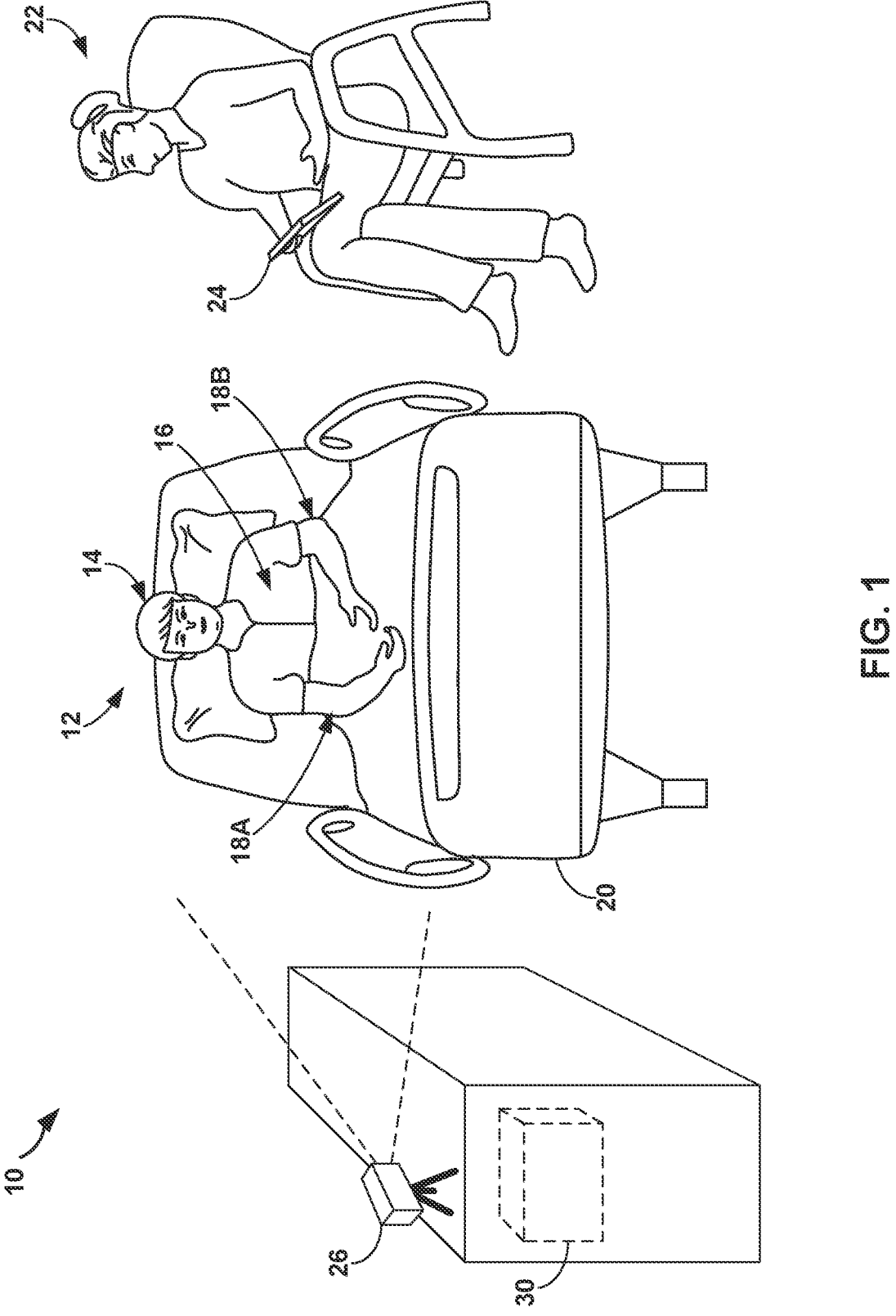
FIG. 1 is a conceptual diagram illustrating an example system that includes a camera for capturing video information of patient movements during a period of time.

This disclosure is generally directed to devices, systems, and techniques for analyzing video information to objectively identify patient behavior such as patient movement. A clinician (e.g., doctor, nurse, or other healthcare professional) diagnose or evaluate a movement disorder of a patient may visually monitoring the movements of the patient. A movement disorder may be caused by neurological disorders and/or other physiological disorders. Various scales and tests have been developed to perform such evaluations. For example, the Unified Parkinson's Disease Rating Scale, motor scale (mUPDRS) is typically used to evaluate motor performance of patients suspected or diagnosed with Parkinson's disease. During the test, the clinician asks the patient to perform a routine of passive and active motor tasks while the clinician provides scores intended to characterize the movement and/or capabilities of the patient. However, tests such as the mUPDRS test may be inaccurate, inconsistent, and/or unreliable because they rely on clinician training and experience, are only available during limited visits to a clinic, and are subject to patient and clinician fatigue.

As disclosed herein, algorithms are described to objectively identify and evaluate patient movement as one or more patient behaviors (e.g., movement disorders associated with abnormal behavior). A system may incorporate one or more devices to automatically identify patient behavior from patient motion. For example, a camera may generate video information (e.g., a plurality of image frames) that captures patient motion or movement during a period of time. This patient movement may be passive (i.e., uninstructed by a clinician or system). Alternatively, the patient movement may be active (i.e., in response to commands given to the patient).

A system (e.g., a networked server or external programmer) may obtain and analyze the video information captured during the period of time. The system may determine one or more sample areas of respective anatomical regions in one or more of the frames and analyze the other frames to determine areas that correspond to the sample areas. The system may also calculate one or more movement parameters that characterize the movement of the areas within the frames of the period of time. The system may then compare the calculated values of the respective movement parameters to criteria of each of a plurality of patient behaviors (e.g., abnormal behaviors). Based on this comparison, the system may identify which ones of the patient behaviors were exhibited by the patient during the period of time in which the video information was captured. In this manner, the system can be configured to identify a plurality of different patient behaviors from the same video information and over the same period of time. Therefore, video information captured during passive patient movement, instead of instructed active patient movement, can be analyzed to identify patient behavior. However, behavior identification may still be used based on video information captured during instructed active patient movement.

The identified patient behavior may be used to diagnose movement disorders, evaluate and assess movement disorder severity, and/or monitor the progression of any disease underlying the movement disorder. In addition, a system or device may control therapy (e.g., electrical stimulation therapy, drug delivery therapy, and/or oral medication therapy) in response to identifying a patient behavior from the video information. In this manner, the identified patient behavior may be used as feedback for controlling the therapy. Video information may be captured continuously, periodically, and/or on-demand and analyzed to identify the patient behavior for feedback.

In other examples, the identified patient behavior may be correlated with other patient parameters that are used as feedback to control therapy delivery. For example, the system may obtain values for one or more patient parameters sensed during the same time as video information was captured of the patient. After identifying the patient behaviors occurring during the period of time, the system may correlate, or associate, the values of the sensed patient parameters with the patient behaviors that occurred at the same time. In this manner, the system may generate respective thresholds, ranges, formulas, look up tables, for one or more patient parameters that indicate when the patient is experiencing each of a plurality of patient behaviors. Although the video information may be used to calibrate one or more patient parameters to the patient behaviors, a device may control therapy in response to sensing one or more sensed values of the patient parameters. Patient parameters may include, local field potentials (LFPs), electrograms (EEGs), electroencephalograms (EEG), patient accelerations, relative accelerations, patient speech, physiological chemistry, or any other parameter of the patient that may be indicative of a behavior associated with a movement disorder.

FIG. 1 is a conceptual diagram illustrating example system 10 that includes camera 26 for capturing video information of patient movements during a period of time. As shown in FIG. 1, system 10 may include camera 26, computing device 30, and external programmer 24. FIG. 1 also illustrates patient 12 lying in bed 20 and clinician 22 sitting next to patient 12 and holding external programmer 24. An implantable medical device (not shown) may be implanted within patient 12 and configured to deliver therapy to patient 12. Programmer 24 may communicate with the implantable medical device (IMD) to adjust therapy, obtain sensed values of one or more patient parameters, and/or communicate any other commands between the two devices.

System 10 may be configured to capture video information of the motion of patient 12. As patient 12 lies in bed 20, patient 12 may move head 14, torso 16, arm 18A or arm 18B (example anatomical regions). In some cases, patient 12 may also move one or both legs, fingers, hands, feet, or any other anatomical regions. These movements may be voluntary and/or involuntary as a result of movement disorder experienced by patient 12. When the movements of patient 12 are not performed in response to a command to perform a certain movement or action, the movement of patient 12 may be described as passive movement. If patient 12 has a movement disorder, various patient behaviors (e.g., the result of one or more anatomical region movements) may manifest themselves during a period of time. Camera 26 may be positioned to capture the movement of patient 12 over a period of time using a plurality of video frames. These video frames may be at least part of the video information captured of patient 12.

Camera 26 may include one or more types of sensors for detecting patient motion. In one example, camera 26 may have one or more sensors (e.g., charge-coupled device (CCD) or complementary metal-oxide-semiconductor (CMOS)) configured to convert visible light to electrical signals representing the visible light. In other examples, camera 26 may include other sensors that are configured to capture infra-red electromagnetic radiation and/or any other medium representative of the movement of patient 12. In other examples, two or more cameras may be placed at different locations with respect to patient 12 in order to obtain different perspectives of the patient movement that may be undetectable at some angles or vantage points. Although camera 26 may generally be positioned to capture the entire body of patient 12, camera 26 may be focused to one or more specific anatomical regions in other examples.

Camera 26 may capture video information (e.g., video frames and, in some examples, information regarding the frames such as time and location the frames were captured) of patient movement over various periods of time. Camera 26 may capture video information for minutes, hours, days, or even months. Camera 26 may capture video information continuously (e.g., at a specified frame rate) over the period of time. In other examples, camera 26 may be configured to capture video information periodically such as at scheduled times and/or at various frame rates. For example, camera 26 may be configured to capture video information of patient 12 during the time of day at which patient 12 is likely to be active and moving (e.g., during the day time, during meals, or during scheduled activities). In this manner, camera 12 may be configured to capture video information in response to user input requesting video information. In other examples, camera 26 may be configured to capture video information in response to a request to capture video information. The request may be generated in response to receiving a user request, in response to a sensed parameter (e.g., an accelerometer indicating patient 12 is moving), or in response to a request for additional video information due to potential problems with identified patient behaviors.

Camera 26 may transmit the captured (or generated) video information to computing device 30 via wired or wireless communication protocols. Computing device 30 may be configured to temporarily or permanently store the video information from camera 26. In some examples, computing device 30 may also be configured to control the operation of camera 26 based on stored instructions and/or commands received from another device over a network. In this manner, computing device 30 may be in wired or wireless communication with additional computing devices (e.g., a networked server, programmer 24, and/or other computing device) via a network, such as network 42 of FIG. 3. In other examples, programmer 24 may be configured to at least partially control the operation of camera 26.

Although camera 26 may be a separate device, camera 26 may be integrated into a computing device. For example, camera 26 may be integrated into the housing of computing device 30 and/or a display coupled to computing device 30. In other examples, camera 26 may be housed by a mobile computing device or notebook computer. In this manner, video information may be captured by devices other than a standalone camera positioned within a single room. Instead, a mobile computing device (e.g., a smartphone, a tablet computer, or programmer 24) may include camera 26 configured to capture the video information used to objectively identify patient behavior. Clinician 22 or even patient 12 may then capture video information of patient movement at any location.

In some examples, computing device 30 may obtain the video information from camera 26, analyze the video information, and identify patient behaviors from the video information. Computing device 30 may also be associated with a display configured to present the identified patient behavior to clinician 22. Computing device 30 may instead transmit the identified patient behavior to external programmer 24 for presentation to clinician 22. In other examples, computing device 30 may be configured to transmit the video information to a networked server via a network. Computing device 30 may continuously or periodically transfer the video information captured by camera 26 to a device configured to analyze the video information and identify any patient behavior that occurred in the video information.

As described herein, one or more processors of a computing device may be configured to identify patient behaviors from video information captured by camera 26. For example, the computing device may be configured to obtaining video information of patient motion captured over a period of time, such that the video information comprises a plurality of frames. The computing device may then receive, with respect to one or more frames of the plurality of frames, a selection of a sample area representative of an anatomical region (e.g., head 14, torso 16, arm 18A, or arm 18B). This sample area may be defined by user input and/or the one or more processors. The computing device may also analyze each of the other plurality of frames for respective areas corresponding to the sample area. The computing device can then calculate one or more movement parameters (e.g., velocity, angle of movement, or frequency of movement) of the anatomical region during the period of time from at least one difference between the sample area and one or more respective areas of at least a subset of the plurality of frames. The computing device may also be configured to compare the one or more movement parameters of the period of time to respective criteria for each of a plurality of predetermined patient behaviors (e.g., types of movements or movement disorders) and identify, based on the comparison, each one of the predetermined patient behaviors that occurred during the period of time.

The identified patient behaviors may be abnormal behaviors that are included in or representative of respective movement disorders. The identified patient behaviors may indicate a type of movement (e.g., dyskinesia, bradykinesia, or tremor) and the severity of each type of movement. The identified patient behaviors may be transmitted to external programmer 24, or another clinician device, for viewing by clinician 22. Clinician 22 may diagnose patient 12 and/or monitor the progression of a disease using the identified patient behaviors. In addition, clinician 22 may establish a treatment regimen in response to receiving the identified patient behavior. In the situation in which an IMD (e.g., an electrical stimulator and/or drug pump) is within patient 12, clinician 22 may interact with external programmer 24 to command the IMD to control therapy based on the identified patient behavior. In some examples, a computing device such as a networked server or external programmer 24 may select one or more therapies (e.g., select therapy parameters) in response to receiving the identified patient behaviors. In this manner, the identified patient behaviors may be used to influence some therapy for patient 12.

Although video information is described as being captured as patient 12 lies in bed 20, camera 26 may capture video information of any activity of patient 12. Camera 26 may capture video information of patient 12 as patient 12 walks across the room, watches television, sits in a chair, maintains a selected posture, talks, eats a meal, interacts with clinician 22 or any other healthcare professional, or performs any other normal routine tasks or activities.

If the one or more anatomical regions of patient 12 are undetectable in the captured video information, the system may determine an uncertainty as to the location of the anatomical region and exclude such frames from the motion analysis. In this manner, video information captured over an extended period of time and patient activities may be analyzed to identify patient movement without unwanted patient positions affecting the accuracy of the identified patient movement.

Figure 2:
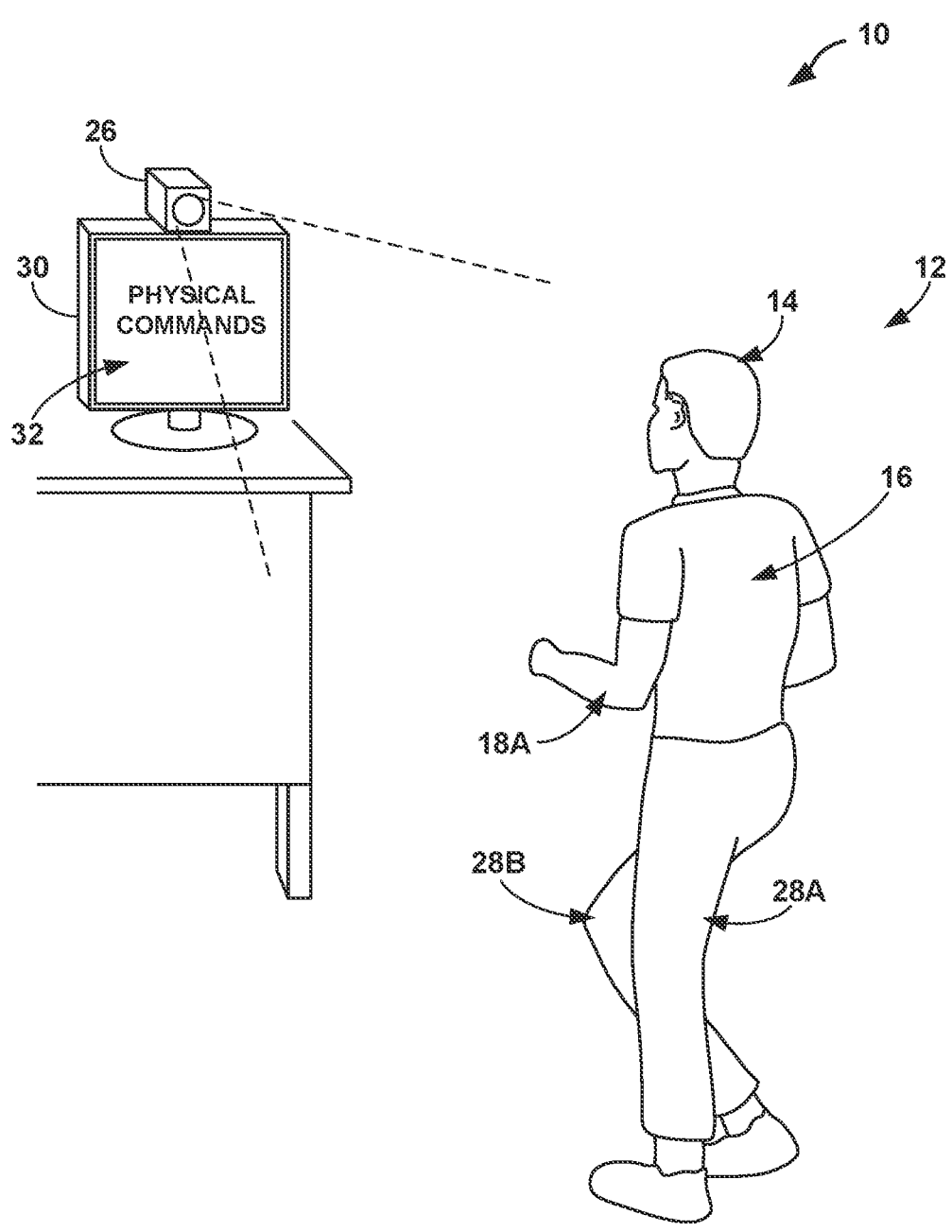
FIG. 2 is a conceptual diagram illustrating an example system that includes a display for presenting commands to a patient and a camera for capturing video information of patient movements that occur in response to the commands.

FIG. 2 is a conceptual diagram illustrating example system 10 that includes display 32 for presenting commands to patient 12 and camera 26 for capturing video information of patient movements that occur in response to the commands. As shown in FIG. 2, system 10 includes camera 26, computing device 30, and display 32. System 10 may be configured to capture video information while display 32 presents physical commands for patient 12 to complete. In some examples, patient behavior may be identified based on the ability or inability of patient 12 to perform certain actions. System 10 may be configured to instruct patient 12 to perform these actions in an automated manner that does not require a clinician to interact with patient 12. In some examples, system 10 may present the instructions in a game-type format that challenges patient 12 to complete a certain task to receive a certain score. In this manner, patient movement may be assessed outside of the clinic setting, such as at the home of patient 12. In addition, the movement assessment may be performed more frequently to closely monitor the progression of any movement disorder and corresponding neurological disease or physiological issue.

Computing device 30 may be configured to conduct a movement assessment of patient 12 during which video information is captured of patient movement. The assessment may be initiated by patient input, a scheduled time to begin the assessment, or remote initiation via a network. Computing device 30 may generate and output various physical commands to be displayed to patient 12. These physical commands may be selected according to assessment instructions stored within a memory of computing device 30 or obtained from another computing device (e.g., a networked server or remote computing device) via a network. Display 32 may be configured to display or present the physical commands to patient 12. The physical commands may be in the form of text, audio, and/or images of a person performing the requested actions.

Camera 26 may be positioned in such a manner to capture the movements of one or more anatomical regions of patient 12. Although camera 26 may be configured to capture the entire body of patient 12 within the field of view of camera 26, camera 26 may be configured to capture video information for a portion of patient 12. Computing device 30 may be configured to control camera 26 to capture video information during the period of time in which patient 12 is performing the movements instructed by the physical commands. For example, the video information may include patient 12 moving head 14, torso 16, arm 18A, legs 28A and 28B, or any other movements. The movements may include intentional movements desired by patient 12 and unintentional movements resulting from the movement disorder of patient 12. The physical commands may include commands to move individual anatomical regions such as an arm, perform various coordinated movements between anatomical regions, or full body motions such as walking, sitting, or standing. For instance, system 10 (or a clinician) may instruct patient 12 to perform tasks such as performing finger taps between the thumb and index finger of one or more hands in rapid succession, opening and closing one or more hands in rapid succession, performing rapid alternating movements of one or more hands, and/or any additional movements. As another example, system 10 or a clinician may instruct patient 12 to attempt to rise from a chair while maintaining the patient's arms folded across the chest. Leg and foot agility of patient 12 may be tested via heel taps instructed to be performed in rapid succession while the patient's leg is raised by predetermined magnitude or angle, such as three inches, during each tap. In other examples, a clinician may devise customized tests whereby patient 12 is instructed to go through specific motions. The clinician may, in some examples, apply resistance while patient 12 performs some motions to further test the patient's capabilities. System 10 may implement and conduct each of these tests by presenting instructions to patient 12 and/or a clinician and capturing video information of the patient's motion during each test.

Since camera 26 may be configured to capture movements of the entire body of patient 12, the captured video information may include motions from all anatomical regions of patient 12. Therefore, the single video information may be analyzed for the presence of multiple patient behaviors (e.g., abnormal behaviors) as described herein. The assessment described in FIG. 2 may be performed instead of or in addition to the passive movement assessment described with respect to FIG. 1. Physical commands given to patient 12 may be time stamped, or otherwise correlated to the captured video frames, for comparison to the video information to assess the patient movement.

In other examples, one or more sensors may sense a respective patient parameter during the patient movement of FIG. 1 or 2. These patient parameters may obtain non-video information indicative of some aspect of patient movement. The patient parameters may be calibrated with the identified patient behavior from the captured video information to provide feedback indicative of patient behavior. This feedback may be used to supplement behavior monitoring of patient 12 and/or to control therapy delivered to patient 12. The sensors may be attached to patient 12, implanted within patient 12, or associated with another object in contact with patient 12. Example sensors may include electrodes and electrical signal sensing modules, accelerometers, microphones, chemical sensors, or any other type of sensor configured to obtain information regarding the movement of patient 12.

Figure 3:
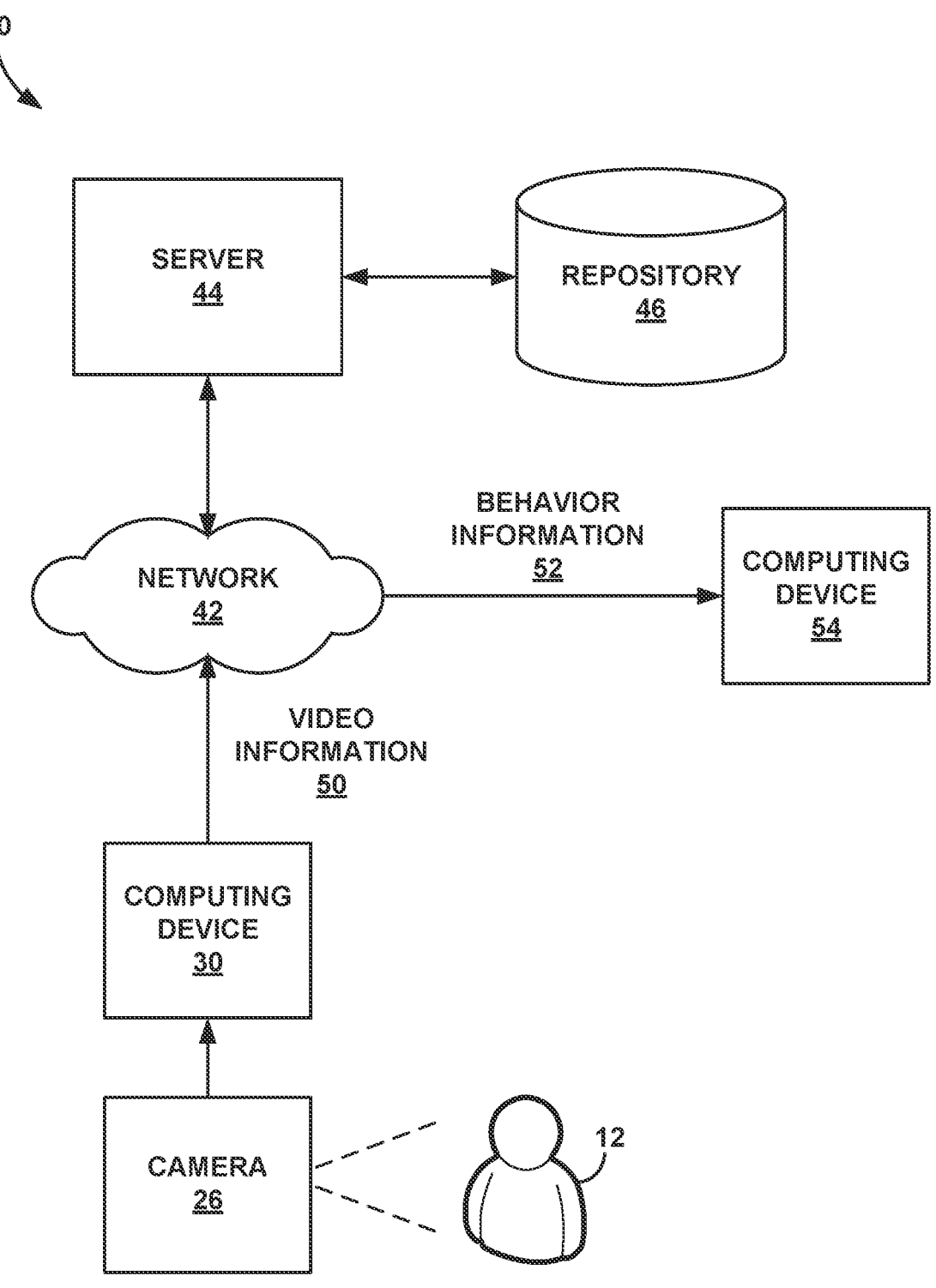
FIG. 3 is a conceptual diagram illustrating an example system that includes a networked server for identifying patient behavior based on the video information captured by the camera of FIG. 1 or FIG. 2.

FIG. 3 is a conceptual diagram illustrating example system 40 that includes networked server 44 configured to identify patient behavior based on video information 50 captured by camera 26 of FIG. 1 or FIG. 2. As shown in FIG. 3, system 40 includes computing device 30, camera 26, network 42, networked server 44 (e.g., a computing device), repository 46, and computing device 54. Computing device 30, in some examples, is or is a part of a portable computing device (e.g., a mobile phone, a smartphone, a netbook computer, a notebook computer, a tablet computing device, or a smart watch). In other examples, computing device 30 may be at least a part of a workstation or other non-portable computing device. Computing device 30 may also include a display device (e.g., display 32 of FIG. 2) and be configured to control the display device. The display device may be housed by computing device 30 or external from computing device 30. Although camera 26 may be a separate device in communication with computing device 30, camera 26 may be coupled to or at least partially within a housing of computing device 30. Computing device 30 may receive video information 50 from camera 26 and/or generate at least a portion of video information 50 such as time stamps, any physical commands given to user 12, or any other metadata associated with the video frames of video information 50.

Computing device 30 may be configured to connect to network 42 (e.g., a wired or wireless network). In some examples, computing device 30 may also be configured to communicate with networked server 44 via network 42 to transmit captured video information 50. Although network 42 may be a single network, network 42 may be representative of two or more networks configured to provide network access to server 44 and/or repository 46. Computing device 30 may be configured to transmit captured video information 50 after the video information is completed generated or stream video information 50 to networked server 44 as the video information is captured. In some examples, computing device 30 may receive instructions from networked server 44 to control camera 26 to begin or terminate the capturing of video information. In other examples, networked server 44 may provide finer control of video information capture, such as video frame rates, video capture settings, compression of video information, or any other aspect related to capturing the video information of patient movement.

Computing device 30 may include various components that provide respective functionality. For example, computing device 30 may control a display device such as display 32 of FIG. 2. Computing device 30 may include one or more input devices and/or output devices that facilitate user (e.g., a clinician or a patient) communication with computing device 30. In one example, a user interface may include the display device and separate input devices or a display device may be touch screen interface (e.g., a presence-sensitive display that includes a presence-sensitive input device). In other examples, the display device may include a display and one or more buttons, pads, joysticks, mice, tactile devices, or any other device capable of turning user actions into electrical signals that control computing device 30. In any example, the user clinician may interact with the display device or any other input devices to provide input prior to or during the processes described herein.

Computing device 30 may be configured to transmit video information 50 to networked server 44 via network 42. Networked server 44 may be configured to store video information 50 in repository 46 until the video information is to be analyzed and/or for long-term storage. Both computing device 30 and networked server 44 may connect to network 42. Network 42 may be embodied as one or more of the Internet, a wireless network, a wired network, a cellular network, or a fiber optic network. In other words, network 42 may be any data communication protocol or protocols that facilitate data transfer between two or more devices. Networked server 44 may also connect to repository 46 to store and/or retrieve video information 50 received from computing device 30, patient information, patient parameter values, behavior identification rules, or any other data or instructions needed to identify the patient behavior exhibited during capture of video information 50.

Networked server 44 and repository 46 may each include one or more servers or databases, respectively. In this manner, networked server 44 and repository 46 may be embodied as any hardware necessary to store video information 50, generated behavior information 52, or any other information related to the diagnosis, monitoring, and/or treatment of patient 12. Networked server 44 may include one or more servers, desktop computers, mainframes, minicomputers, or other computing devices capable of executing computer instructions and storing data. In some examples, functions attributable to networked server 44 herein may be attributed to respective different servers for respective functions. Repository 46 may include one or more memories, repositories, hard disks, or any other data storage device. In some examples, repository 46 may be included within networked server 44.

Repository 46 may be included in, or described as, cloud storage. In other words, EGM signal data, EGM summaries, patient reports, instructions, or any other such information may be stored in one or more locations in the cloud (e.g., one or more repositories 46). Networked server 44 may access the cloud and retrieve the appropriate data as necessary. In some examples, repository 46 may include Relational Database Management System (RDBMS) software. In one example, repository 46 may be a relational database and accessed using a Structured Query Language (SQL) interface that is well known in the art. Repository 46 may alternatively be stored on a separate networked computing device and accessed by networked server 44 through a network interface or system bus. Repository 46 may thus be an RDBMS, an Object Database Management System (ODBMS), Online Analytical Processing (OLAP) database, or any other suitable data management system.

System 40 may be configured to identify patient behaviors from video information 50. For example, networked server 44 may employ various techniques and processes described herein with respect to FIGS. 6-18 to analyze video information 50 and identify one or more patient behaviors that occurred within the video information. For example, one or more processors of networked server 44 may be configured to calculate movement parameters of one or more anatomical regions within the frames of video information 50, compare values of the movement parameters to respective criteria for predetermined patient behaviors, and identify which patient behaviors occurred within video information 50. Networked server 44 may also identify the severity or progression of each of the patient behaviors. Networked server 44 may compile behavior information 52 that may include the identified patient behaviors, times at which each behavior occurred, a severity of each behavior, confidence levels that such behaviors occurred, or any other information related to the analysis of video information 50 captured by camera 26.

Networked server 44 may transmit the generated behavior information 52 to computing device 54. Computing device 54 may be a computing device configured to deliver information to clinician 22 or patient 12 via a display device or any other such interface. Computing device 54 may be a workstation, mobile computing device, external programmer 24, or any other such device. Computing device 54 may receive behavior information 52 continuously, periodically, in response to generation of behavior information 52 by networked server 44, or in response to user request via computing device 54. Computing device 54 may allow clinician 22 and/or patient 12 to view the movement disorder diagnosis included in behavior information 52, movement parameter values calculated by server 44, at least a portion of video information 50 (e.g., video samples) captured by camera 26, or any other information. In some examples, networked server 44 may also generate suggested actions to take based on the identified patient behavior such as mediations and dosages to take, activities to avoid, or contacting clinician 22 or another healthcare professional.

Computing device 54 may include input/output capabilities such as a user interface configured to accept user input. In some examples, networked server 44 may require user input to analyze video information 50 and identify the patient behaviors. For example, user input may be received by computing device 54 to define a sample area of one or more video frames that corresponds to a desired anatomical region. The sample area may be of head 14, torso 16, or any other anatomical region of interest. Computing device 54 may then transmit the user input and/or sample area back to networked server 44 for completion of the analysis and identification. In addition, networked sever 44 may require the user to, at least initially, set one or more criteria for one or more of the patient behaviors to be identified. The criteria may include one or more thresholds, ranges, comparisons, or any other values desired by clinician 22 or specific to patient 12. Computing device 54 may transmit the user defined criteria to networked server 44 for use in identifying the patient behavior present within video information 50. Networked server 44 may store the user defined criteria in repository 46. Networked server 44 may also store any generated behavior information 52 in repository 46.

Although server 44 is generally disclosed as the computing device configured to generate behavior information 52 and perform other tasks, different computing devices may perform these functions in other examples. For example, computing device 30 or computing device 54 may perform some or all of the steps described herein with respect to identifying patient behavior from video information 50. In this manner, other computing devices, such as computing device 30, may perform the operations attributed to server 44. In still other examples, server 44, computing device 30, computing device 54, and/or other computing devices may operate cooperatively to perform the processes described herein with respect to analyzing video information 50 and generating behavior information 52.

Figure 4:
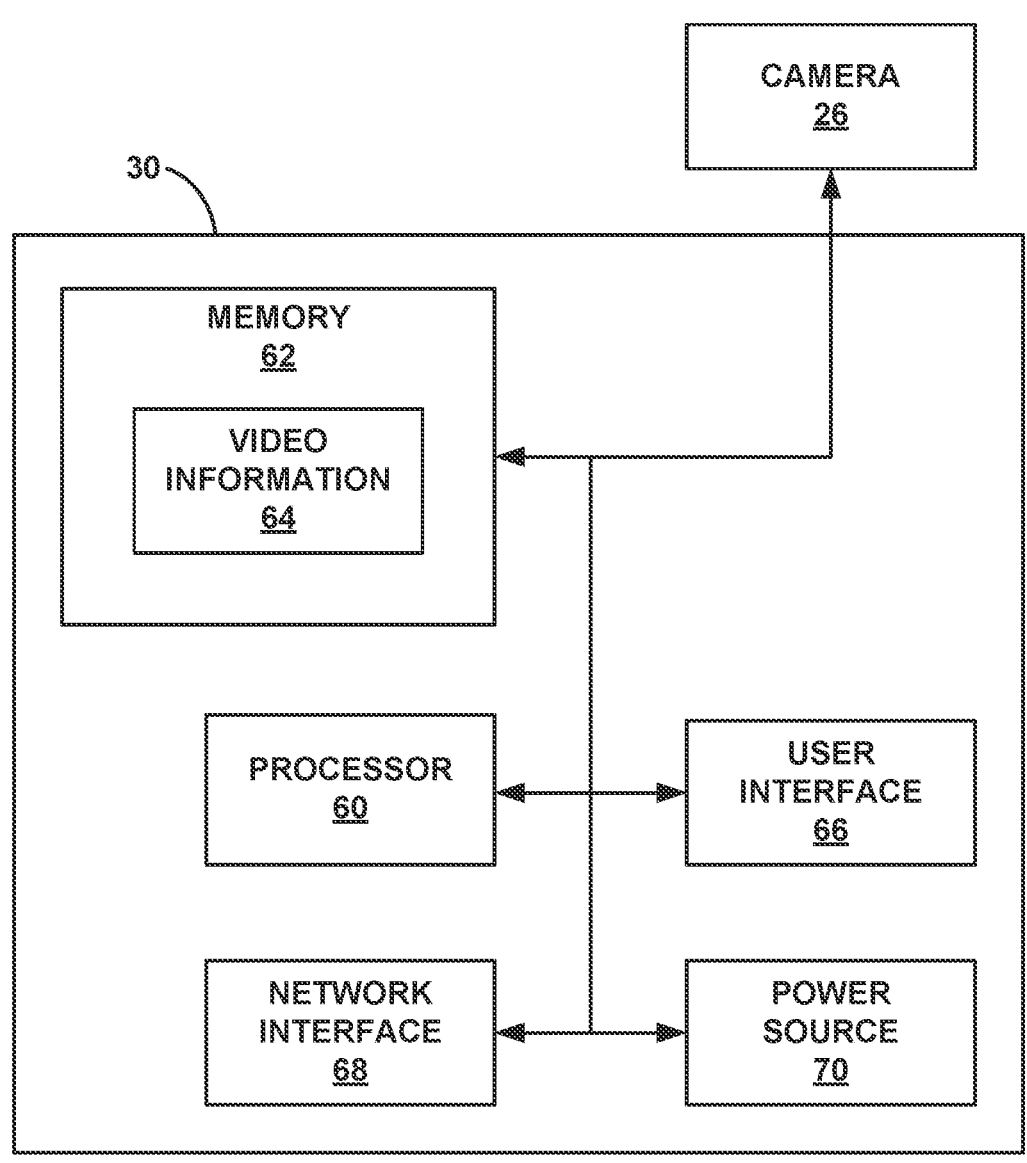
FIG. 4 is a block diagram of the example computing device of FIGS. 1 and 2.

FIG. 4 is a block diagram of example computing device 30 of FIGS. 1, 2, and 3. FIG. 4 illustrates only one particular example of computing device 30, and many other example embodiments of computing device 30 may be used in other instances. For example, computing device 30 may include additional components and run multiple different applications. Computing device 30 may be configured to obtain and/or generate video information from camera 26 and transmit the video information to networked server 44 for analysis.

As shown in FIG. 4, computing device 30 may include processor 60, memory 62, user interface 66, telemetry module 68, and power sources 70. Camera 26 may be located separately from computing device 30 and in communication with computing device 30 and processor 60. In other examples, camera 26 may be incorporated within computing device 30. Each of components 26, 60, 62, 66, 68 and 70 may be interconnected (physically, communicatively, and/or operatively) for inter-component communications and functionality.

Processor 60, in one example, is configured to implement functionality and/or process instructions for execution, such as controlling camera 26 to capture video information and storing video information 64 (e.g., video information 50 of FIG. 3), for temporary and/or long term storage, within memory 62. Processor 60 may also be configured to process instructions stored within memory 62. Processor 60 may also be configured to generate metadata or supplemental data (e.g., time stamps, video parameter values, or any other related information) to the plurality of video frames captured by camera 26 and store such data with the video frames as the video information 64.

Memory 62, in one example, is configured to store information within computing device 30 during operation. Memory 62, in some examples, is described as a computer-readable storage medium. Memory 62 may also be described as a storage device or computer-readable storage device. In some examples, memory 62 is a temporary memory, meaning that a primary purpose of memory 62 is not long-term storage. However, memory 62 may also be described as non-transitory. Memory 62, in some examples, may be described as a volatile memory, meaning that memory 62 does not maintain stored contents when the computer is turned off. Examples of volatile memories include random access memories (RAM), dynamic random access memories (DRAM), static random access memories (SRAM), and other forms of volatile memories known in the art. In some examples, memory 62 is used to store program instructions for execution by processor 60.

Computing device 30, in some examples, also includes a network interface 68. Computing device 30, in one example, utilizes network interface 68 to communicate with other computing devices (e.g., networked server 44 of FIG. 3), programmers (e.g., programmer 24 of FIG. 1), computing devices 54 of FIG. 3, or more networks, such as network 42 shown in FIG. 3. In this manner, computing device 30 may transmit captured video information 64 to other computing devices and/or receive instructions related to capturing the video information. Network interface 68 may be a network interface card, such as an Ethernet card or other wired interface. In other examples, network interface 68 may include an optical transceiver, a radio frequency transceiver, or any other type of device that can send and receive information. Other examples of such network interfaces may include Bluetooth, 3G and WiFi radios in mobile computing devices as well as USB. In some examples, computing device 30 utilizes network interface 68 to wirelessly communicate with another computing device (e.g., computing device 54 of FIG. 3) or other networked computing devices.

Computing device 30, in one example, also includes one or more user interfaces 66. User interface 66 may include a touch-sensitive and/or a presence-sensitive screen, mouse, a keyboard, a voice responsive system, camera, or any other type of device for detecting a command from a user. In one example, user interface 66 may include a touch-sensitive screen, sound card, a video graphics adapter card, or any other type of device for converting a signal into an appropriate form understandable to humans or machines. In addition, user interface 66 may include a speaker, a cathode ray tube (CRT) monitor, a liquid crystal display (LCD), or any other type of device that can generate intelligible output to a user.

Computing device 30, in some examples, includes one or more power sources 70, which provide power to computing device 30. Generally, power source 70 may utilize power obtained from a wall receptacle or other alternating current source. However, in other examples, power source 70, may include one or more rechargeable or non-rechargeable batteries (e.g., constructed from nickel-cadmium, lithium-ion, or other suitable material). In other examples, power source 70 may be a power source capable of providing stored power or voltage from another power source.

Figure 5:
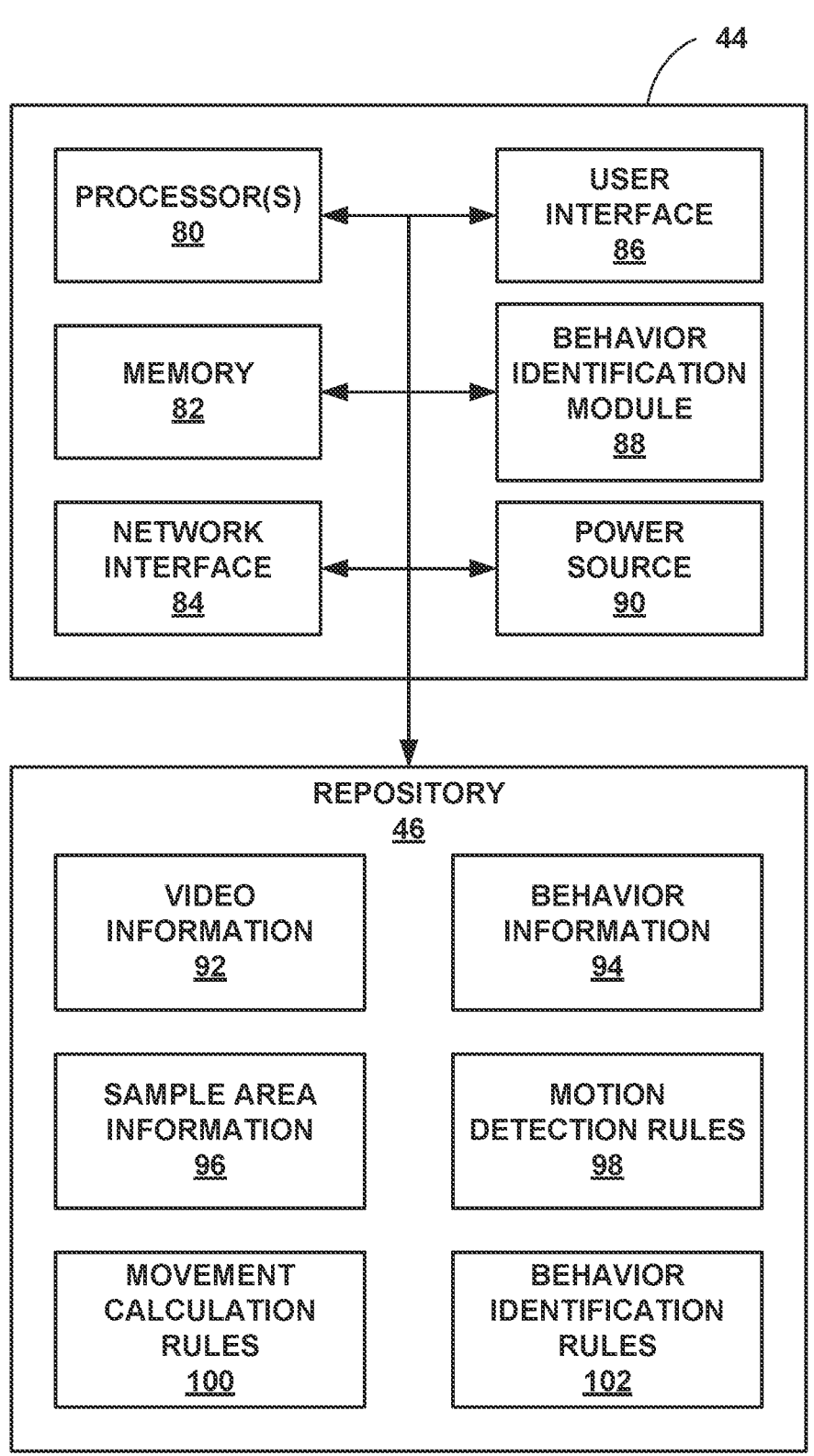
FIG. 5 is a block diagram of the example networked server of FIG. 3.

FIG. 5 is a functional block diagram illustrating an example configuration of networked server 44 and repository 46 of FIG. 3. FIG. 5 illustrates only one particular example of server 44, and many other example embodiments of server 44 may be used in other instances. For example, server 44 may include additional components and run multiple different applications. Server 44 may be configured to identify patient behavior from captured video information (e.g., video information 50 of FIG. 3) and, in some examples, select one or more therapies to be delivered to patient 12 based on the identified behaviors. For example, server 44 may be configured to perform some or all of the processes described with respect to FIGS. 6-18.

As shown in the specific example of FIG. 5, server 44 may include and/or house one or more processors 80, memory 82, a network interface 84, user interface 86, behavior identification module 88, and power source 90. Server 44 may be in communication with repository 46, such that repository 46 is located external of server 44. In other examples, repository 46 may include one or more storage devices within an enclosure of server 44. Server 44 may also include an operating system, which may include modules and/or applications that are executable by processors 80 and server 44. Each of components 80, 82, 84, 86, 88, and 90 may be interconnected (physically, communicatively, and/or operatively) for inter-component communications.

Processors 80, in one example, are configured to implement functionality and/or process instructions for execution within server 44, such as identifying patient behavior from video information captured of patient movement. For example, processors 80 may be capable of processing instructions stored in memory 82 or instructions stored in repository 46. These instructions may define or otherwise control the operation of server 44. In some examples, behavior identification module 88 (which may include one or more dedicated processors) may be configured to analyze the video information 50 and identify the patient behaviors that occurred within the video information.

Memory 82, in one example, is configured to store information within server 44 during operation. Memory 82, in some examples, is described as a computer-readable storage medium. Memory 82 may also be described as a storage device or computer-readable storage device. In some examples, memory 82 is a temporary memory, meaning that a primary purpose of memory 82 is not long-term storage. However, memory 82 may also be described as non-transitory. Memory 82, in some examples, may be described as a volatile memory, meaning that memory 82 does not maintain stored contents when the computer is turned off. Examples of volatile memories include random access memories (RAM), dynamic random access memories (DRAM), static random access memories (SRAM), and other forms of volatile memories known in the art. In some examples, memory 82 is used to store program instructions for execution by processors 80. Memory 82, in one example, is used by software or applications running on server 44 to temporarily store information during program execution. Although memory 82 of FIG. 5 is not described as including motion detection rules 98, movement calculation rules 100 or behavior identification rules 102, for example, memory 82 may store such instructions and other data in other examples.

Repository 46, in some examples, also includes one or more computer-readable storage media, such as one or more storage devices. Repository 46 may be configured to store larger amounts of information than memory 82. Repository 46 may further be configured for long-term storage of information. In some examples, repository 46 may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Repository 46 may be configured to store information related to or collected from each of multiple patients. For example, repository 46 may be configured to store video information collected from one or more patients as video information 92. Each patient, and each period of time during which video information was captured for each patient, may be have separate memories or allocated space to store such data. Repository 46 may also store the behavior information (e.g., behavior information 50) generated for each patient. Behavior information 94 may include the patient behaviors that were identified for each period of time in which video information was captured for each respective patient. Repository 46 may also store additional data, such as movement parameter values, that is generated during the process of identifying patient behavior from video information.

Repository 46 may also include data used to allocate sample areas of respective anatomical regions represented within the plurality of frames of the video information and analyze the frames. For example, sample area information 96 may include instructions for allocating, or determining, sample areas used to track anatomical region movement between frames of the captured video information. The instructions of sample area information 96 may request a user to define a sample area corresponding to an anatomical region in a sample frame. In addition, sample area information 96 may include instructions for automatically defining a supplemental sample area based on the location of the sample area defined by the user (e.g., the sample area may represent head 14 of patient 12 and the supplemental sample area may be torso 16 of patient 12). In some examples, sample area information 96 may include instructions for automatically analyzing, or searching, the video frames of the captured video information for one or more frames suitable for defining a sample area. Repository 46 may also store any sample areas defined by user input and/or determined by server 44. Examiner processes and techniques stored as sample area information 96 may be included in FIGS. 7 and 18.

In addition, repository 46 may store additional rules and instructions used to identify patient behavior from video information. Motion detection rules 98 may include rules or instructions for processors 80 to determine motion of anatomical regions between frames of video information. Motion detection rules 98 may include at least some of the processes described in example FIGS. 8-10. For example, motion detection rules 98 may instruct processors 80 to filter the captured pixels and generate a motion track map.

Movement calculation rules 100 may be stored by repository 46 and provide instructions to processors 80 regarding calculating values of movement parameters. The calculated movement parameter values may characterize the movement of anatomical regions between frames of the video information. Movement detection rules 100 may include at least some of the processes and techniques described in example FIGS. 11-13. For example, movement detection rules 100 may include instructions for calculating the velocities and velocity angles of anatomical region movement and/or frequencies of movement in each frame. These movement parameter values may be used to identify which patient behaviors are present within the captured video information.

Behavior identification rules 102 may be stored by repository 46 and provide instructions to processors 80 regarding the criteria for identifying behaviors from the calculated movement parameters. The patient behaviors may be predetermined and selected when the movement parameter values indicate that the patient behavior has occurred. Behavior identification rules 102 may include the processes and techniques of example FIGS. 14-17. For example, behavior identification rules 102 may include criteria for determining when the calculated movement parameter values indicate that the predetermined patient behaviors of dyskinesia, bradykinesia, or tremor have occurred in one or more anatomical region of patient 12.

According to the rules and information stored in repository 46, processors 80 may thus automatically analyze video information 50 to determine which patient behaviors occurred in the frames of the video information. In one example, processors 80 may be configured to obtain video information 50 of patient motion captured over a period of time. The video information may include a plurality of frames (e.g., video frames). Processors 80 may be configured to receive, with respect to one frame of the plurality of frames, a selection of a sample area representative of an anatomical region. Processors 80 may then be configured to analyze each of the other plurality of frames for respective areas corresponding to the sample area and calculate one or more movement parameters of the anatomical region during the period of time from at least one difference between the sample area and one or more respective areas of at least a subset of the plurality of frames. Processors 80 may next be configured to compare the one or more calculated movement parameters of the period of time to respective criteria for each of a plurality of predetermined patient behaviors. Using these comparisons, processors 80 may be configured to identify, based on the comparison, each one of the predetermined patient behaviors that occurred during the period of time.

Server 44, in some examples, also includes a network interface 84. Server 44, in one example, utilizes network interface 84 to communicate with other computing devices (e.g., computing device 54 of FIG. 3), programmers (e.g., programmer 24 of FIG. 3), medical devices, or more networks, such as network 42 shown in FIG. 3. In this manner, server 44 may receive video information 50 and transmit information such as behavior information 50. Network interface 84 may be a network interface card, such as an Ethernet card or other wired interface. In other examples, network interface 84 may include an optical transceiver, a radio frequency transceiver, or any other type of device that can send and receive information. Other examples of such network interfaces may include Bluetooth, 3G and WiFi radios in mobile computing devices as well as USB. In some examples, server 44 utilizes network interface 84 to wirelessly communicate with another computing device (e.g., computing device 54 of FIG. 3) or other networked computing devices.

Server 44, in one example, also includes one or more user interfaces 86. User interface 86 may include a touch-sensitive and/or a presence-sensitive screen, mouse, a keyboard, a voice responsive system, camera, or any other type of device for detecting a command from a user. In one example, user interface 86 may include a touch-sensitive screen, sound card, a video graphics adapter card, or any other type of device for converting a signal into an appropriate form understandable to humans or machines. In addition, user interface 86 may include a speaker, a cathode ray tube (CRT) monitor, a liquid crystal display (LCD), or any other type of device that can generate intelligible output to a user.

Server 44, in some examples, includes one or more power sources 90, which provide power to server 44. Generally, power source 90 may utilize power obtained from a wall receptacle or other alternating current source. However, in other examples, power source 90, may include one or more rechargeable or non-rechargeable batteries (e.g., constructed from nickel-cadmium, lithium-ion, or other suitable material). In other examples, power source 90 may be a power source capable of providing stored power or voltage from another power source.

Server 44 may, in some examples, utilize behavior identification module 88 to identify which patient behaviors occurred within the video information. Behavior identification module 88 may communicate with repository 46 to retrieve, in accordance with instructions such as stored commands or user input, sample area information 96, motion detection rules 98, movement calculation rules 100, and behavior identification rules 102 as needed to identify the behaviors of the patient. Behavior identification module 88 may include dedicated hardware (e.g., one or more processors), firmware, and/or software to perform the functions described herein. In other examples, one or more of processors 80 may perform some or all of the functions described herein within respect to behavior identification module 88. Any software implemented within or executed by server 44 may be implemented or contained within, operable by, executed by, and/or be operatively/communicatively coupled to components of server 44 (e.g., processors 80, memory 82, network interface 84, and/or repository 46).

FIGS. 6-18 are flow diagrams illustrating various processes and techniques that may be used to identify patient movement behaviors from video information captured of patient 12. Each of FIGS. 6-18 may provide portions or subparts of the overall process that may be used in some examples. Generally, one or more processors 80 of networked server 44 are described as performing the described processes in FIGS. 6-18. However, the processes may be performed by one or more other devices or systems (e.g., computing device 30 or computing device 54 or combinations of different processors and/or devices in other examples.

Figure 6:
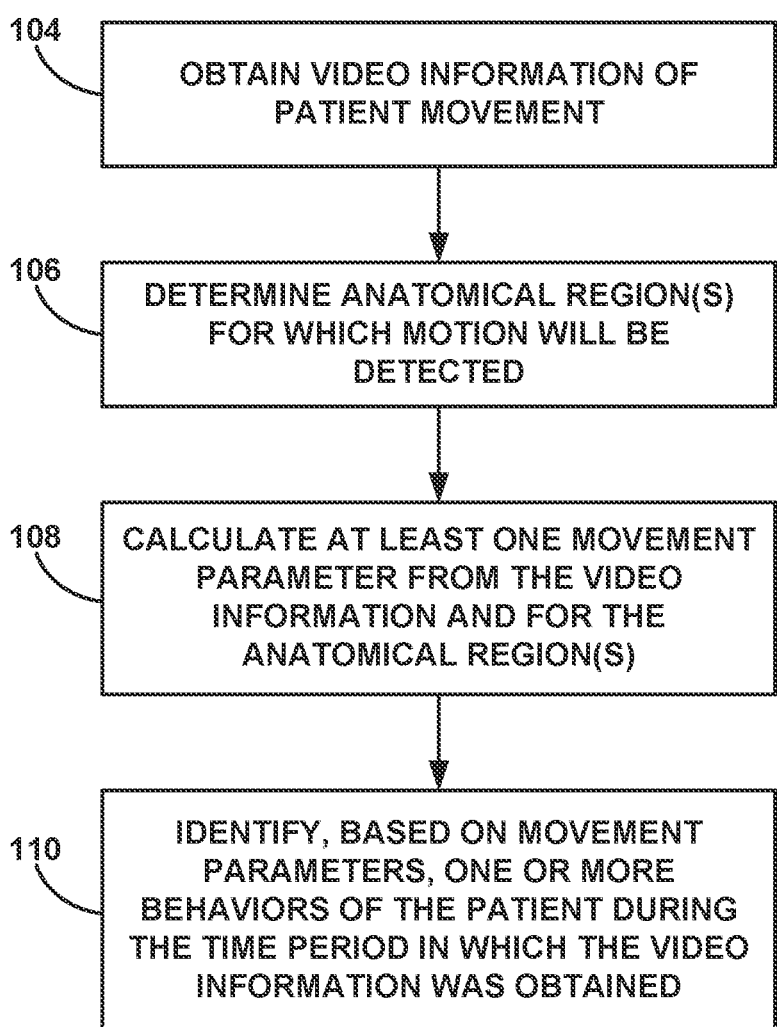
FIG. 6 is a flow diagram that illustrates an example process for identifying patient behaviors based on analyzed video information of the patient.

FIG. 6 is a flow diagram that illustrates an example process for identifying patient behaviors based on analyzed video information 50 of patient 12. As shown in FIG. 6, an example overall process may be used by processors 80 to identify one or more patient behaviors that occurred during the period of time in which video information 50 was captured by camera 26. Processors 80 may obtain video information 50 of the movement of patient 12 captured during a period of time (104). Video information 50 may include a plurality of frames. Processors 80 may also determine the anatomical region or regions for which motion will be detected from video information 50 (106). Determining the anatomical regions may include receiving user input defining one or more sample area of one or more video frames that correspond to the desired anatomical regions. In other examples, processors 80 may define a sample area for another anatomical region based on the user defined first sample area.

Processors 80 may also calculate at least one movement parameter from video information 50 and for the one or more anatomical regions defined in the one or more frames (108). In some examples, processors 80 may analyze the frames of video information 50 to identify the areas within frames that correspond to each respective sample area. In this manner, processors 80 may define the anatomical region within each of the frames prior to calculating the movement parameters. In response to calculating the movement parameter values for each of the frames of video information 50, processors 80 may identify, based on the movement parameter values, one or more patient behaviors of patient 12 during the period of time in which video information 50 was obtained (110). Since this identification may be based on the comparison of movement parameter values to criteria for each of a plurality of predefined patient behavior, processors 80 may generate an objective indication of the patient behavior and movement disorders. Networked server 44 may then output the identified patient behaviors to computing device 54 via network 42, in some examples.

In some examples, processors 80 may identify patient behavior based on movement parameters for multiple anatomical regions. For example, one region may be head 14 of patient 12 and another region may be torso 16 of patient 12. Processors 80 may determine the respective areas of each frame that correspond to the anatomical regions and calculate one or more movement parameters of the head and torso regions during the period of time from at least one difference between the respective sample areas and one or more respective areas of a subset of the plurality of frames corresponding to the respective sample areas. Processors 80 may then be configured to identify each one of the predetermined patient behaviors that occurred during the period of time based on the respective movement parameters of both the head and the torso regions of patient 12.

Figure 7:
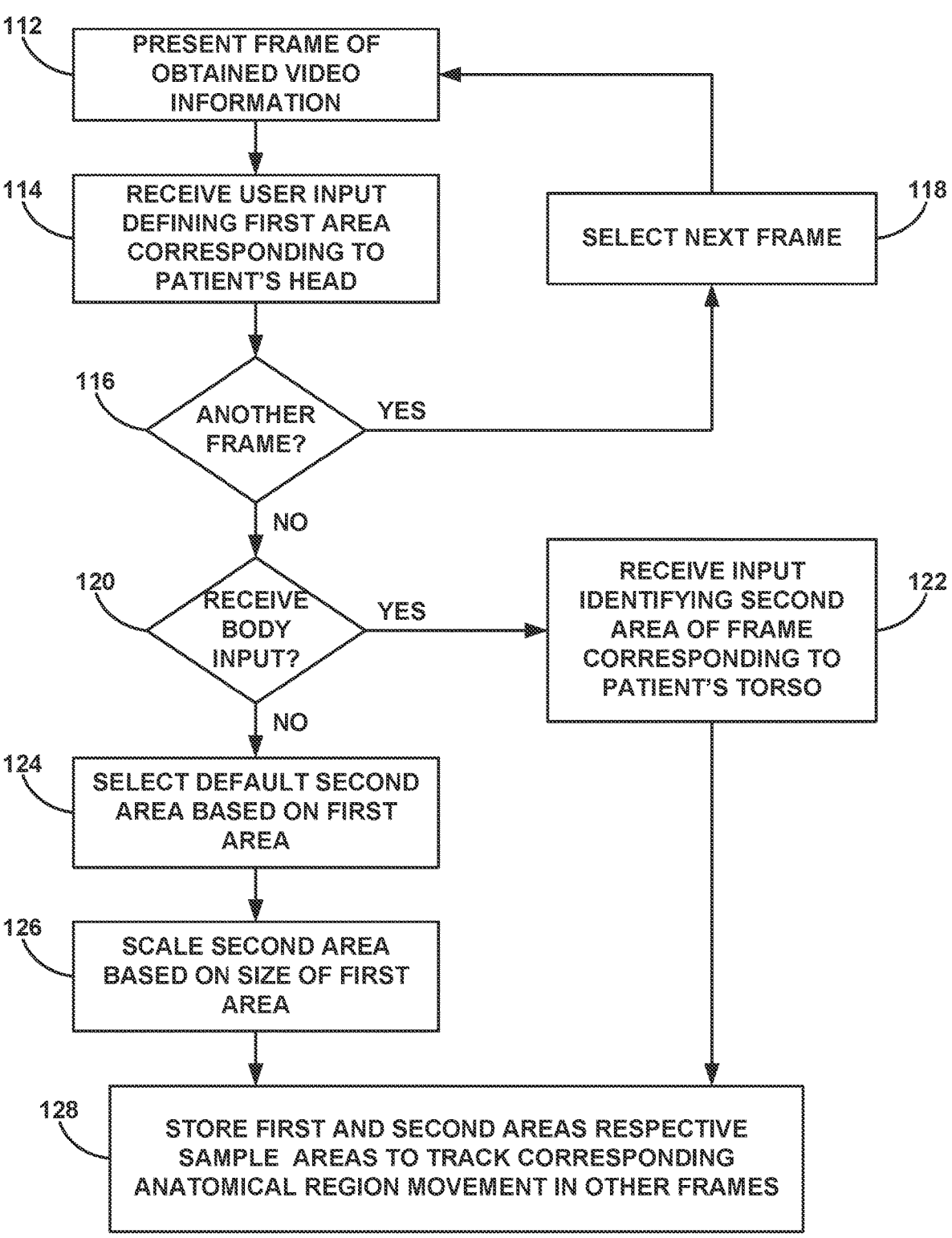
FIG. 7 is a flow diagram that illustrates an example process for allocating sample areas representing a respective anatomical region captured in the video information.

FIG. 7 is a flow diagram that illustrates an example process for allocating sample areas representing a respective anatomical region captured in video information 50. As shown in FIG. 7, processors 80 may obtain video information 50 of patient 12 and output or control a display device to present a frame of video information 50 (112). For example, processors 80 may transmit the frame to computing device 54 for presentation to a user. Processors 80 may receive, with respect to the one frame presented to the user, a selection or a user input defining a first area corresponding to head 14 of patient 12 (114). If there is another frame in which a sample area should be defined ("YES" branch of block 116), processors 80 may select the next frame (118) and continue to output or present the frame to a user (112). Multiple sample areas for the same anatomical region may be defined for the video information to account for variations in video quality, non-continuous video information, and/or different angles in which one sample area may not be sufficient to track the anatomical region through other frames.

If there is no other frame to select a sample area ("NO" branch of block 116), processors 80 may check to see if there is any user input to select the body or torso 16 anatomical region of patient 12 (120). If there is input to receive ("YES" branch of block 120), processors may receive indications of input identifying a second sample area of the frame that corresponds to torso 16 of patient 12 (112). If there is no input to receive ("NO" branch of block 120), then processors 80 may automatically determine or select a default second sample area that corresponds to torso 16 and is based on the head sample area (124). For example, processors 80 may determine a rectangular area below the center of the sample area of head 14 as the area corresponding to torso 16. Processors 80 may define the top two corners of the rectangular area as the shoulders of patient 12. The rectangular area of the torso may be a default rectangle stored in memory.

Since the default rectangle may not be the appropriate size to the torso of patient 12 in the frame, processors 80 may scale the default rectangle to the size of the sample area of head 14 defined by the user (126). As described herein, various velocity and motion thresholds may be dynamically adjusted based on the size of one or more anatomical regions defined by the corresponding sample area. After processors 80 have determined each of the first and second sample areas that represent the respective anatomical regions, processors 80 may store the sample areas to track the corresponding anatomical region movement through other frames of the period of time in which the video information was captured.

Although the anatomical regions of FIG. 7 are described as head 14 and body 16 of patient 12, any portions of the anatomy of patient 12 may be selected to perform the motion analysis. Only one anatomical region may be identified with a sample area or more than two regions may be identified by respective sample areas. In other examples, the sample area may correspond to other anatomical regions, such as one or more arms, hands, legs, feet, or any combination thereof.

Figure 8:
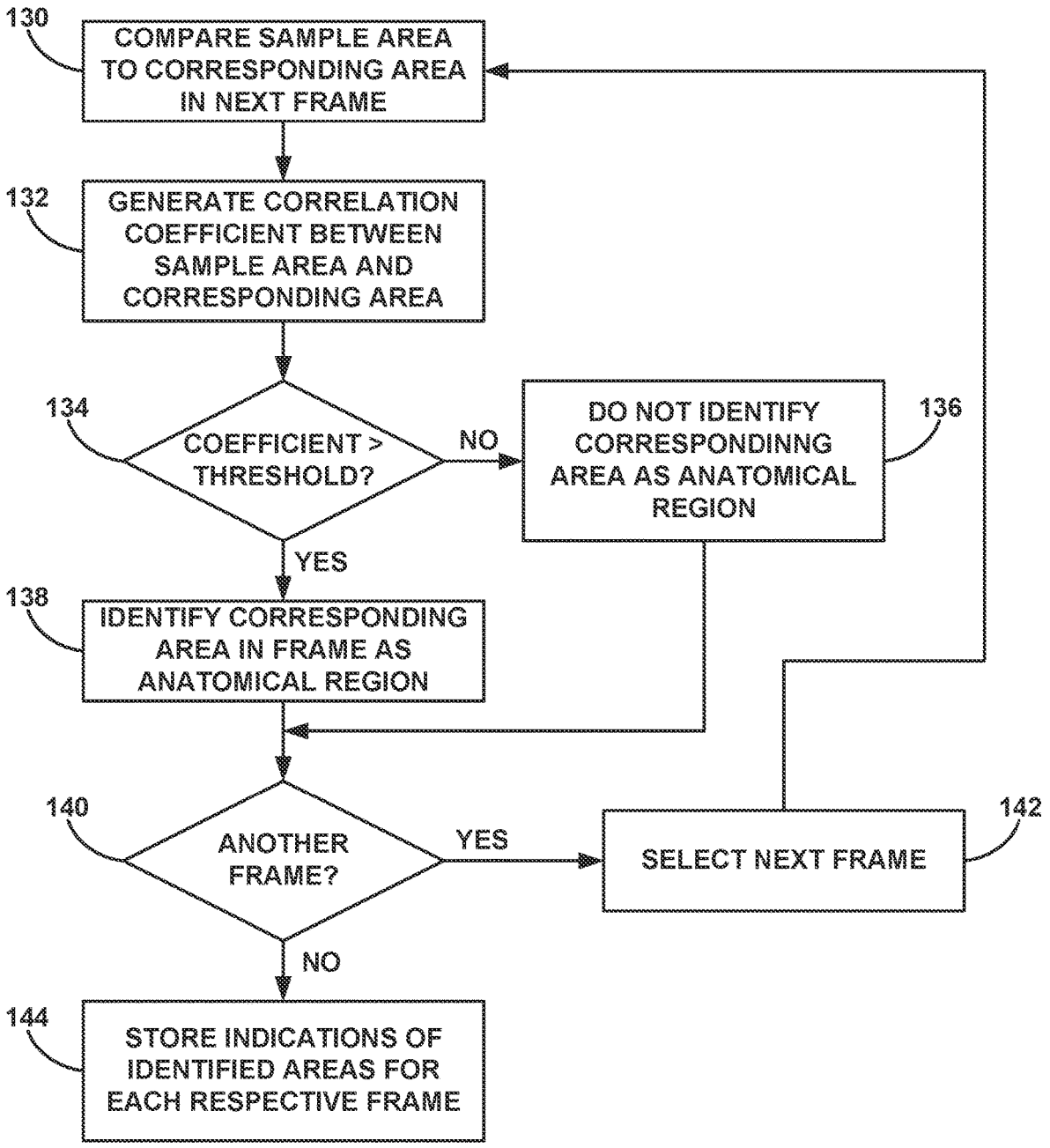
FIG. 8 is a flow diagram that illustrates an example process for identifying areas of video frames corresponding to the sample area of a different frame.

FIG. 8 is a flow diagram that illustrates an example process for identifying areas of video frames corresponding to the sample area of a different frame. Once a sample area is identified, processors 80 can compare the sample area to corresponding areas in the next frame (130). Processors 80 may analyze each of the other frames from the frame with the sample area for respective areas that correspond to the sample area. To complete this process, processors 80 may search successive frames from the area that is temporally contiguous with another area most similar to the sample area. Processors 80 may this determine where the sample area has moved within the frames of the video information.

Since the area of the next frame that is most similar to the sample area may not be exactly the same, processors 80 may generate a correlation coefficient between the sample area and the corresponding area in the subsequent frame by comparing the sample area to the corresponding area (132). If the correlation coefficient is not greater than a correlation threshold ("NO" branch of block 134), processors 80 may not identify the corresponding area in the next frame as the anatomical region of the sample area (136). If the correlation coefficient is greater than the correlation threshold ("YES" branch of block 134), processors 80 may identify the corresponding area in the next frame as the anatomical region of the sample area (138). The correlation threshold may be user-specific, program-specific based on the anatomical region or other criteria, or predetermined.

If there is another frame to analyze for a corresponding area to the sample area ("YES" branch of block 140), processors 80 may select the next frame (142) and again compare the sample area to possible corresponding areas in the next frame (130). If there are no other frames to analyze, ("NO" branch of block 140), processors 80 may store indications of the identified corresponding areas for each of the respective frames (144). Processors 80 may perform the process of FIG. 8 for each of the sample areas and/or anatomical regions (e.g., a head and a torso) selected by a user or otherwise defined in the video information.

FIG. 9 is a flow diagram that illustrates an example process for filtering raw motion pixels from noise in video information 50. As shown in FIG. 9, processors 80 may obtain video information 50 with multiple video frames and select the initial frame of the video information (146). Processors 80 may filter the data in each frame by subtracting the next, or subsequent, frame from the previous frame to generate raw motion pixels (148). In this manner, processors 80 may be configured to generate raw motion pixels for each of the plurality of frames, wherein the raw motion pixels are a difference between pixels of each of the other plurality of frames and its respective prior frame.

For each raw motion pixel of the frame, processors 80 may determine a gray intensity value (150). For each raw motion pixel of the frame processors 80 may compare the respective gray intensity value to a gray intensity threshold (152). Processors 80 may then remove any raw motion pixels with a gray intensity value below the gray intensity threshold (154). Stated another way, processors 80 may be configured to identify raw motion pixels having a gray intensity value greater than the gray intensity threshold as intensity motion pixels for that frame (156). If there is another frame to be filtered ("YES" branch of block 158), processors 80 may select the next frame (160) and generate raw motion pixels for that next frame (148). If there are no other frames to be filtered ("NO" branch of block 158), processors 80 may generate a motion track map comprising the intensity motion pixels of each of the other plurality of frames (162). The process of FIG. 9 may be referred to as gray-intensity filtering.

Figure 10:
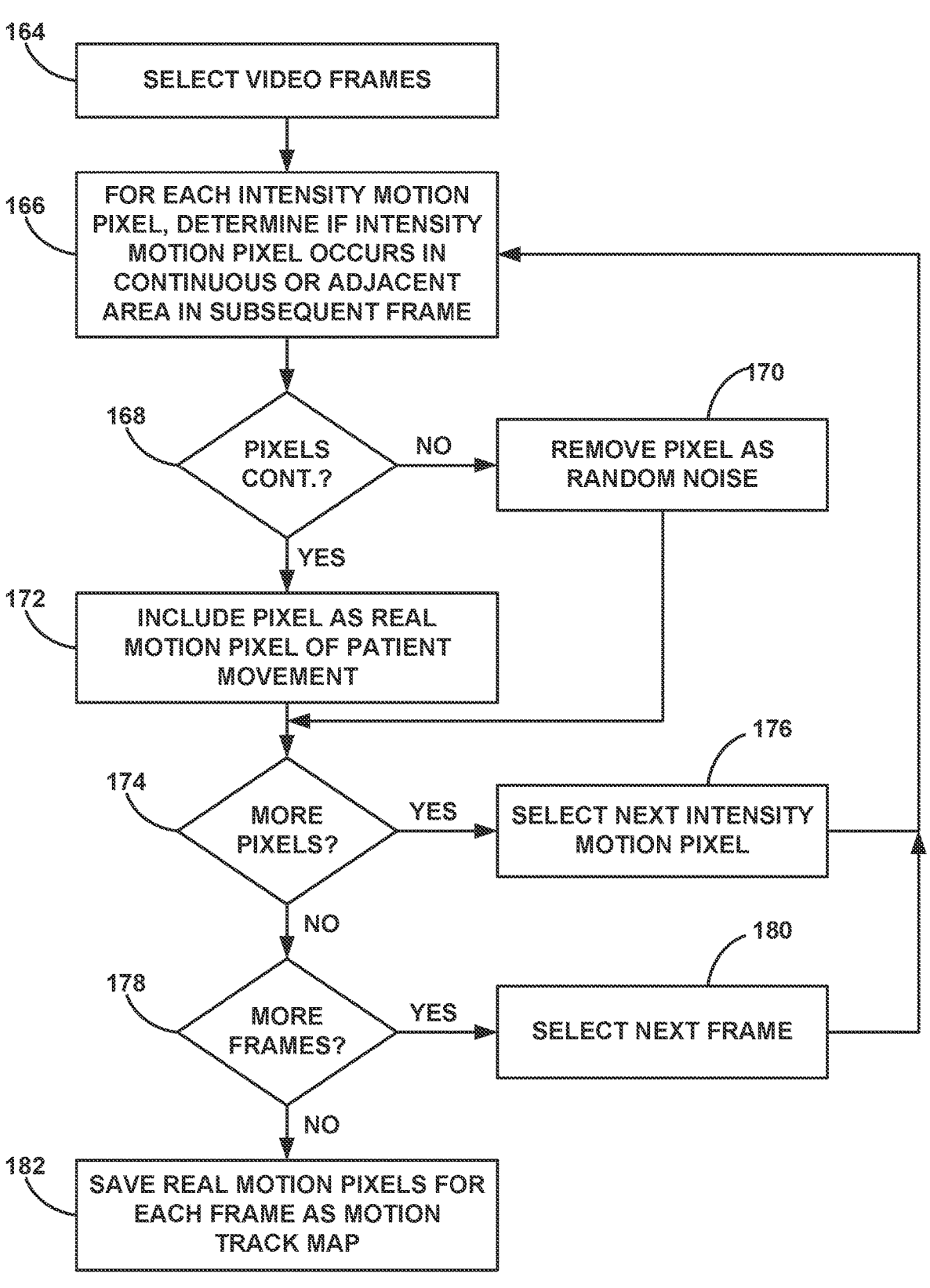
FIG. 10 is a flow diagram that illustrates an example process for generating a motion track map with pixels indicative of patient motion.

FIG. 10 is a flow diagram that illustrates an example process for generating a motion track map with pixels indicative of patient motion. The process of FIG. 10 may be an additional filtering mechanism to the gray-intensity filtering of FIG. 9. Processors 80 may first select the video frames to filter, which may be all of the frames from the video information (164). For each intensity motion pixel generated in FIG. 9, processors 80 may determine if the intensity motion pixel occurs in a continuous or adjacent area in a subsequent frame (166). If the pixels in the pair of frames are not continuous ("NO" branch of block 168), processors 80 may remove the pixel as random noise in the original frame (170). If the pixels in the pair of frames are continuous with each other ("YES" branch of block 168), processors 80 may identify and include the pixel as a real motion pixel representative of movement of the anatomical region (172).

If there are more intensity motion pixels to analyze ("YES" branch of block 174), processors 80 may select the next intensity motion pixel (176) and again determine the continuity of the pixel to a subsequent frame (166). If there are no more pixels in the frame to analyze ("NO" branch of block 174), processors may determine if there are more frames to analyze (178). If there are more frames to analyze ("YES" branch of block 178), processors 80 may select the next frame (180) and again determine the continuity of the pixel in the next frame to a subsequent frame (166). After all intensity motion pixels are analyzed or filtered, processors 80 may save the real motion pixels for each frame as a motion track map (182). In other words, processors 80 may update the motion track map to include only the identified real motion pixels.

Figure 11:
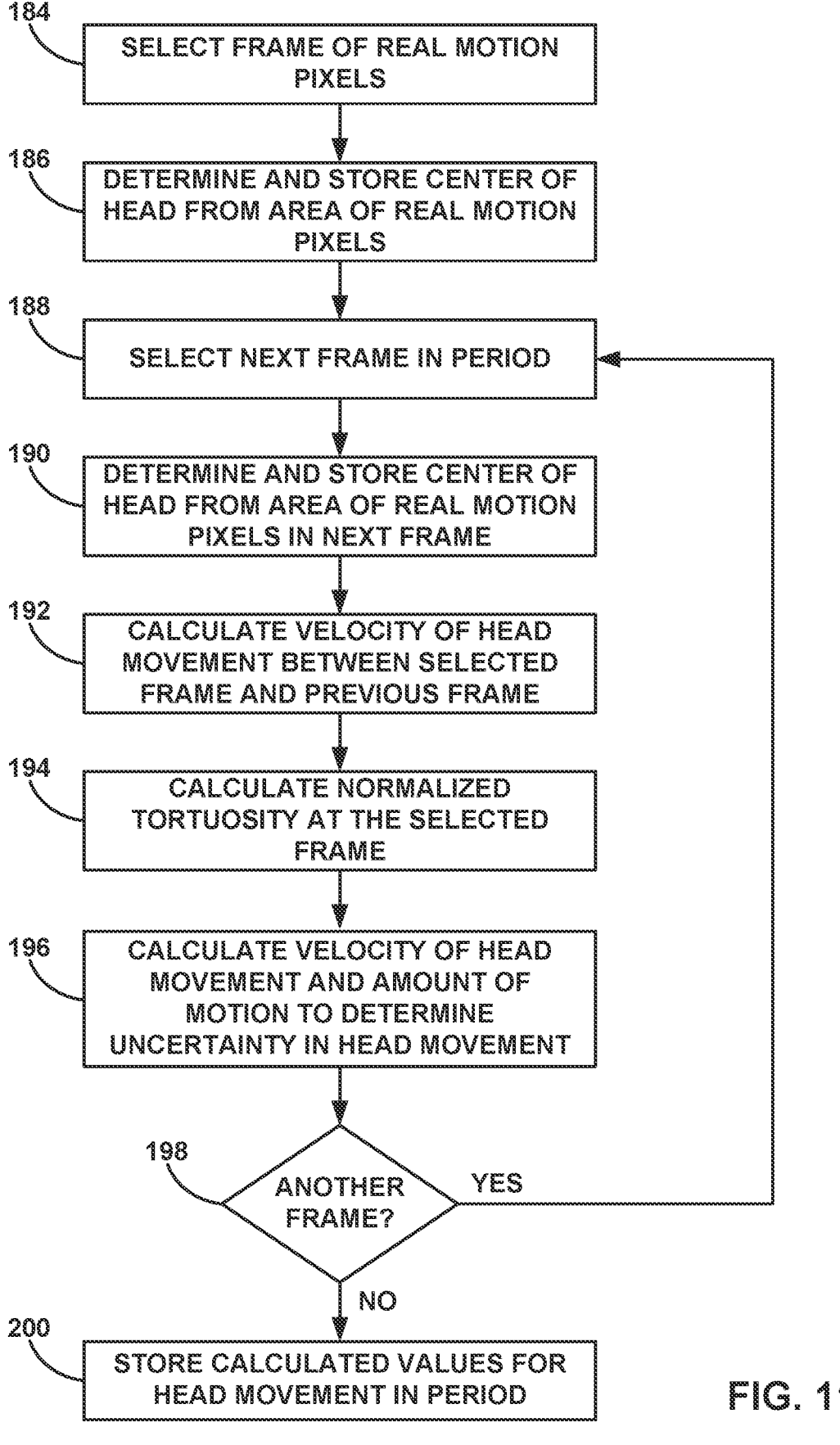
FIG. 11 is a flow diagram that illustrates an example process for calculating movement parameters for each frame of the motion track map of FIG. 10.

FIG. 11 is a flow diagram that illustrates an example process for calculating values of movement parameters for each frame of the motion track map of FIG. 10. The process of FIG. 11 is described with respect to a head of patient 12. However, the same process may be used for other anatomical regions. As shown in FIG. 11, processors 80 may select a frame with the real motion pixels (184). Processors 80 may then determine and store a center of the head from the area of real motion pixels corresponding to the head region (186). After selecting the next frame for the period of time (188), processors 80 may determine and store the center of the head from the area of real motion pixels in this next frame (190). Based on the two center positions of the head in the pair of frames, processors 80 may calculate the velocity of the head movement between the selected frame and the previous frame (192).

Processors 80 may also calculate the normalized tortuosity at the selected frame (194). The normalized tortuosity may be a measure of how much effort patient 12 was using to maintain the head in a certain location. The normalized tortuosity may be a ratio of a distance the center of the corresponding area moved from the prior frame to a distance a center of the anatomical region moved during the period of time. In other words, the ratio is the movement of the head over a short period of time to the movement of the head over a long period of time. A greater ratio indicates a larger tortuosity value and the more effort that a patient needs to use to keep the head in a desired location.

Put another way, the normalized tortuosity may be defined mathematically. At any given frame, the normalized tortuosity may be calculated as:

$$R_F = 1 - \frac{EL_F}{PL_F}, \quad (1)$$

wherein $R_F$ is the normalized tortuosity, $EL_F$ is then end-point length or the distance the head has actually moved over a specified period, and $PL_F$ is the path length or distance the head moved between frames (or between the two frames in which the distance is to be calculated). According to the equation (1), the normalized tortuosity will be close to 1 when the head is quivering between frames and the overall end-point length remains close to zero. Conversely, the normalized tortuosity value may be close to 0 when there is not much quivering motion or total motion of the head.

Processors 80 may also calculate the velocity of the head movement and the amount of motion in addition to the uncertainty of the head movement (196). Processors 80 may determine the uncertainty in the head movement by analyzing the correlation coefficient of the head, determining if the head center moves more than a distance threshold in consecutive frames, and/or a ratio of the movement displacement contradicts the velocity of the head (e.g., there is a small movement displacement and a large velocity). These uncertainty determinations may establish when the behavior may be reliable and when it is not reliable.

Figure 12:
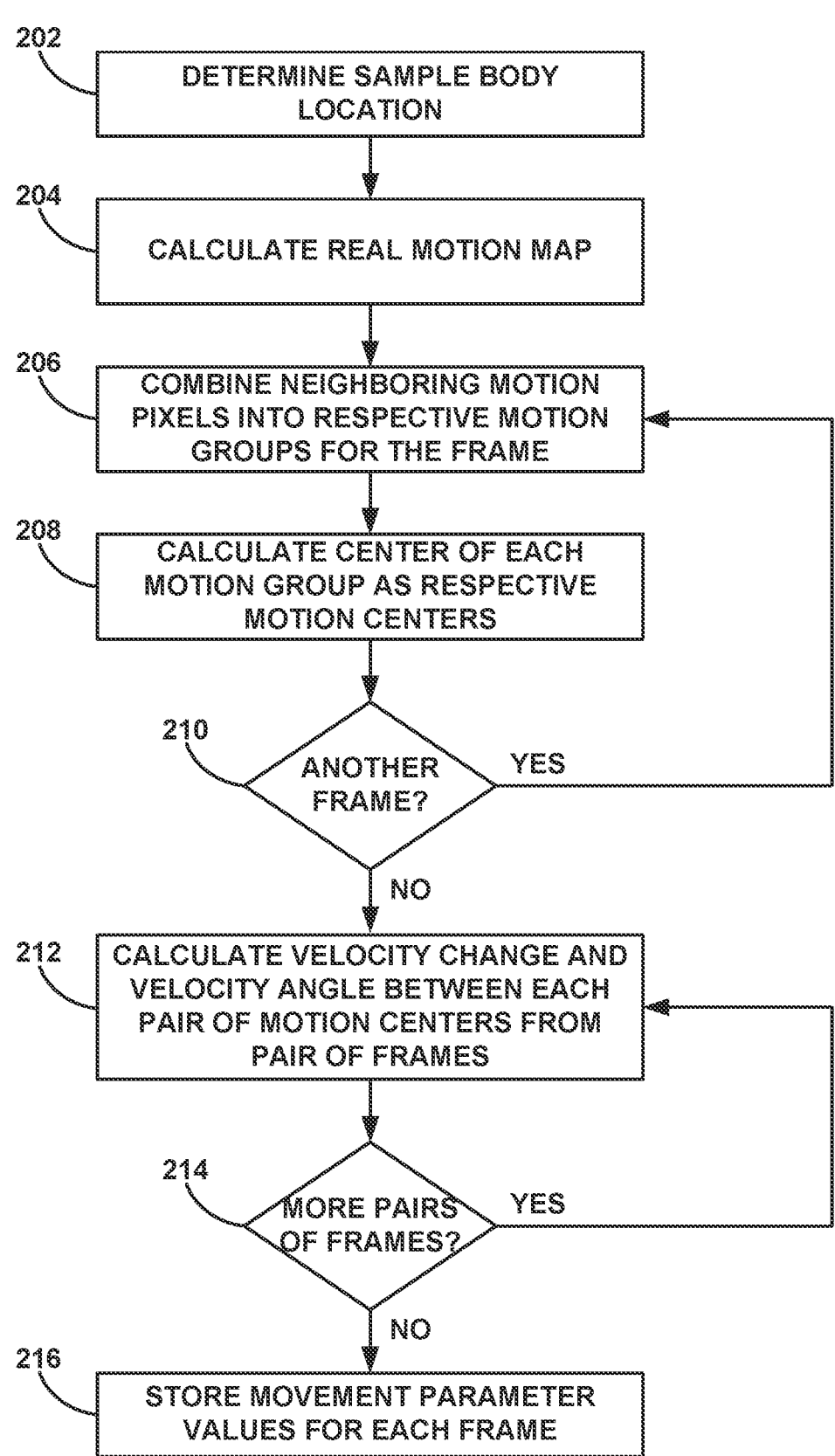
FIG. 12 is a flow diagram that illustrates an example process for generating motion groups of pixels and calculating movement parameters for each of the motion groups.

FIG. 12 is a flow diagram that illustrates an example process for generating motion groups of pixels and calculating movement parameters for each of the motion groups. As shown in FIG. 12, processors 80 may determine or receive a sample body location (e.g., a sample area corresponding to the torso of patient 12) (202) and calculate a real motion map (204) according to the processes described herein. For the identified real motion pixels each of the other plurality of frames, processor 80 may be configured to combine neighboring real motion pixels into respective motion groups (206). Processors 80 may then calculate a motion center for each of the respective motion groups (208). If there is another frame from which motion groups need to be determined ("YES" branch of block 210), processors 80 may select the next frame and combine the neighboring motion pixels into motion groups (206).

If there are no additional frames to analyze ("NO" branch of block 210), processors 80 may, for each of the motion centers, calculate a velocity for the respective frame and calculate a velocity change and a velocity angle between the motion center and the corresponding motion center from the prior frame (212). If there are more pairs of frames ("YES" branch of block 214), processors 80 may again calculate the respective velocity change and velocity angle (212). If there are no further pairs of frames to analyze ("NO" branch of block 214), processors 80 may store the movement parameter values (e.g., storing the velocity, the velocity change, and the velocity angle as respective movement parameter values (216). In some examples, the uncertainty of the body movement described in FIG. 12 may be determined by the uncertainty of the head region previously calculated or other body specific correlation coefficients.

Processors 80 may, in one example, determine the closest pair of motion centers between two consecutive frames $M_F$ and $M_{F-T}$, where T is the length of an analysis period between frames. Let $C_{F,i}$ denote the $i^{th}$ motion center in $M_F$ and $C_{F-T,j}$ denote the $j^{th}$ motion center in $M_{F-T}$ (i.e. $C_{F,i} \in M_F$ and $C_{F-T,j} \in M_{F-T}$). Each pair of motion centers thus indicates a possible movement in a body region in the period of T. If $\{C_{F,i}, C_{F-T,j}\}$ is a matching pair of motion centers in video frame F and (F-T), a movement velocity between $\{C_{F,i}, C_{F-T,j}\}$, denoted as $V_{F,i}$ can then be calculated as $C_{F,i}-C_{F-T,j}$. The velocity angle of $V_{F,i}$, denoted as $A_{F,i}$, is computed as the angle between $V_{F,i}$ and the x-axis. The velocity change $\Delta V_{F,i}$ and angular change $\Delta A_{F,i}$ from frame (F-T) to F for motion center $C_{F,i}$ can then be obtained as $V_{F,i}-V_{F-T,j}$ and $A_{F,i}-A_{F-T,j}$, respectively.

Figure 13:
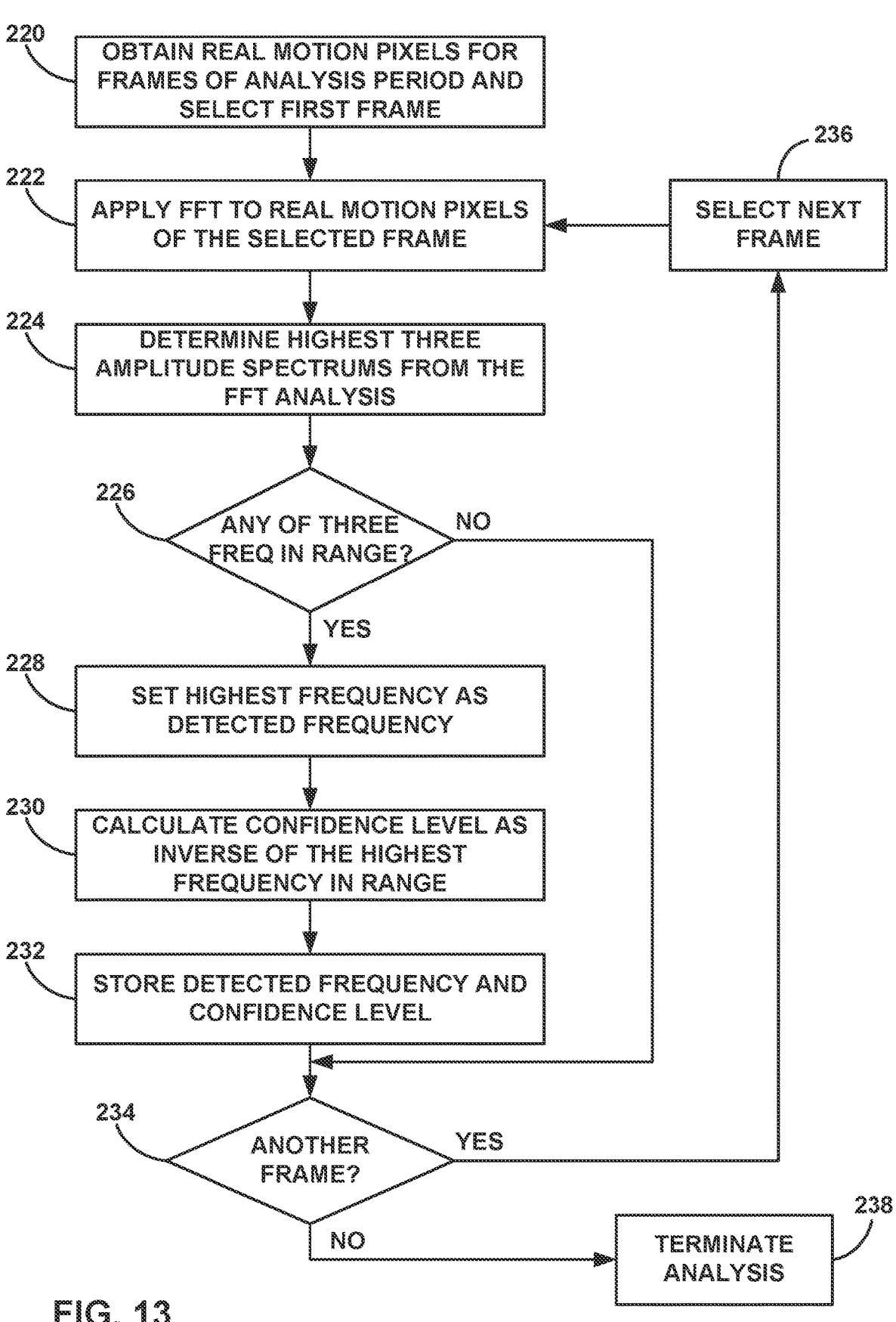
FIG. 13 is a flow diagram that illustrates an example process for calculating movement parameters representing frequency of patient motion.

FIG. 13 is a flow diagram that illustrates an example process for calculating movement parameters representing frequency of patient motion. As shown in FIG. 13, processors 80 may obtain real motion pixels (e.g., from the process of FIG. 10) for frames of an analysis period and select a first frame (220). Processors 80 may apply a fast Fourier transform (FFT) to the real motion pixels of the selected frame (222) and determine the highest three amplitude spectrums from the FFT analysis (224). The highest three amplitude spectrums may be the most common frequencies within the analysis. Processors 80 may determine if any of the three amplitude spectrums are within a predetermined frequency range (226). For example, the predetermined frequency range may be selected according to a certain behavior, such as tremor. An example range of frequency may be approximately 4-8 Hz for detecting the presence of a tremor. Other ranges of frequencies associated with other types of movement disorders may be used in addition to or alternatively from the predetermined frequency range for tremor. Frequency ranges may fall within any movement disorder frequency such as between approximately 0.1 Hz to 50 Hz.

If none of the three highest amplitude spectrums are within the predetermined frequency range ("NO" branch of block 226), processors 80 may select another frame to analyze (234). If any of the three highest amplitude spectrums are within the predetermined frequency range ("YES" branch of block 226), processors 80 may set the highest, or most common, frequency as the detected frequency (228). Processors 80 may also calculate the confidence level as the inverse of the highest frequency in the range (230) and store the detected frequency and confidence level (232). For example, if highest amplitude spectrum is within the predetermined frequency range, the confidence level would be 1. If the third highest amplitude spectrum is within the predetermined frequency range, the confidence level would be ⅓. This frequency analysis may allow processors 80 to extract rhythmic movements for diagnosis and treatment such as tics, blinking, twinges, spasms, hand or limb movements, and trunk movement. If there is another frame to analyze ("YES" branch of block 234), processors 80 may select the next frame (236) and apply the FFT to the next frame (232). If there is no other frame to analyze ("NO" branch of block 234), processors 80 may terminate the analysis (238). Although only the top three amplitude spectrums may be used in this example, other examples may include ranging all of the amplitude spectrums to see if any fall within the predetermined frequency range. The confidence level may then be the inverse of the rank of the frequency.

Figure 14:
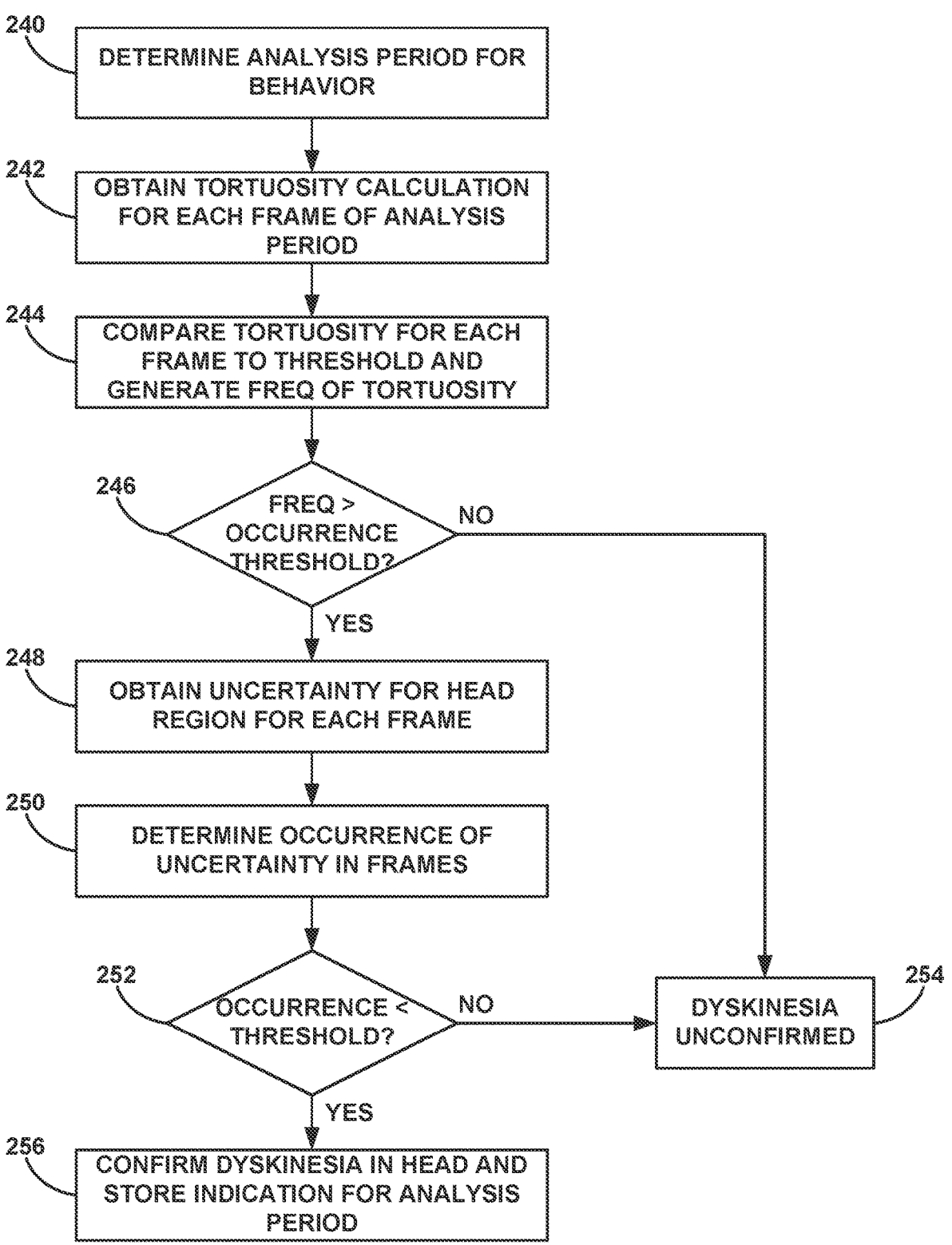
FIG. 14 is a flow diagram that illustrates an example process for identifying dyskinesia in the head of a patient.

FIG. 14 is a flow diagram that illustrates an example process for identifying dyskinesia in the head of patient 12. In other examples, the process of FIG. 14 may be used to identify dyskinesia in a limb or other location of the body. As shown in FIG. 14, processors 80 may determine the analysis period for the behavior (e.g., the period of time that the video information was captured) (240) and obtain the tortuosity calculation for each frame of the analysis period (242). The tortuosity calculation is described in FIG. 11.

For each of the plurality of frames, processors 80 may compare the value of the tortuosity parameter to a tortuosity threshold and generate, based on the comparison for each of the other plurality of frames, a frequency for which the value of the normalized tortuosity exceeded the tortuosity threshold during the period of time (244). If the frequency is less than the tortuosity threshold ("NO" branch of block 246), processors 80 do not confirm dyskinesia of the head (254).

If the frequency is greater than the tortuosity threshold ("YES" branch of block 246), processors 80 may obtain or generate, for each of the other plurality of frames, an uncertainty of the respective areas corresponding to the anatomical region (248). Processors 80 may also determine the occurrence of the uncertainty in the frames. If the uncertainty of the respective areas is greater than an uncertainty occurrence threshold ("NO" branch of block 252), processors 80 may determine that dyskinesia is unconfirmed or not an issue (254). If the uncertainty of the respective areas is less than the occurrence threshold ("YES" branch of block 252), processors 80 may, in response to determining the occurrence of uncertainty, processors 80 may confirm dyskinesia in the head and store the indication for the analysis period.

FIG. 15 is a flow diagram that illustrates an example process for identifying bradykinesia as a patient behavior in a patient. As shown in FIG. 15, processors 80 may obtain the movement parameter values for the analysis period and select a first frame (260). For example, the movement parameter values may be calculated according to the process of FIG. 12. Processors 80 may compare the velocity of the motion center to a velocity threshold (262), compare the change in velocity to a change threshold (264), and compare the change in velocity angle to an angle threshold (266). If processors 80 determine that at least one of one or more motion centers within the respective frame have a velocity greater than a velocity threshold (262), a velocity change less than a velocity change threshold (264), and a velocity angle less than a velocity angle threshold (266), processors 80 may indicate, based on the determination, that bradykinesia occurred in the respective frame (270). If processors 80 determine that at least one of one or more motion centers within the respective frame have a velocity less than a velocity threshold (262), a velocity change greater than a velocity change threshold (264), and a velocity angle greater than a velocity angle threshold (266), processors 80 may indicate, based on the determination, that no bradykinesia was identified within the frame (268).

If processors 80 determine that there is another frame to analyze ("YES" branch of block 272), processors 80 may select the next frame (274) and compare the movement parameter values to their respective thresholds. If processors 80 determine that there are no other frames to be analyzed ("NO" branch of block 272). Processors 80 may identify bradykinesia, or determine that bradykinesia occurred, when bradykinesia has been identified in more than a threshold number of frames (276). Processors 80 may also determine an uncertainty of the respective areas corresponding to the anatomical region occurred at a frequency less than an uncertainty occurrence threshold (278). In response to determining that bradykinesia was identified in a threshold number of frames and that the occurrence uncertainty was less than the uncertainty occurrence threshold, processors 80 may confirm and identify that bradykinesia occurred for the anatomical region during the period of time in which video information was captured (280). The process of FIG. 15 may include various criteria for identifying the patient behavior of bradykinesia. Each of the thresholds may be user-selected, device-selected, or predefined.

Figure 16:
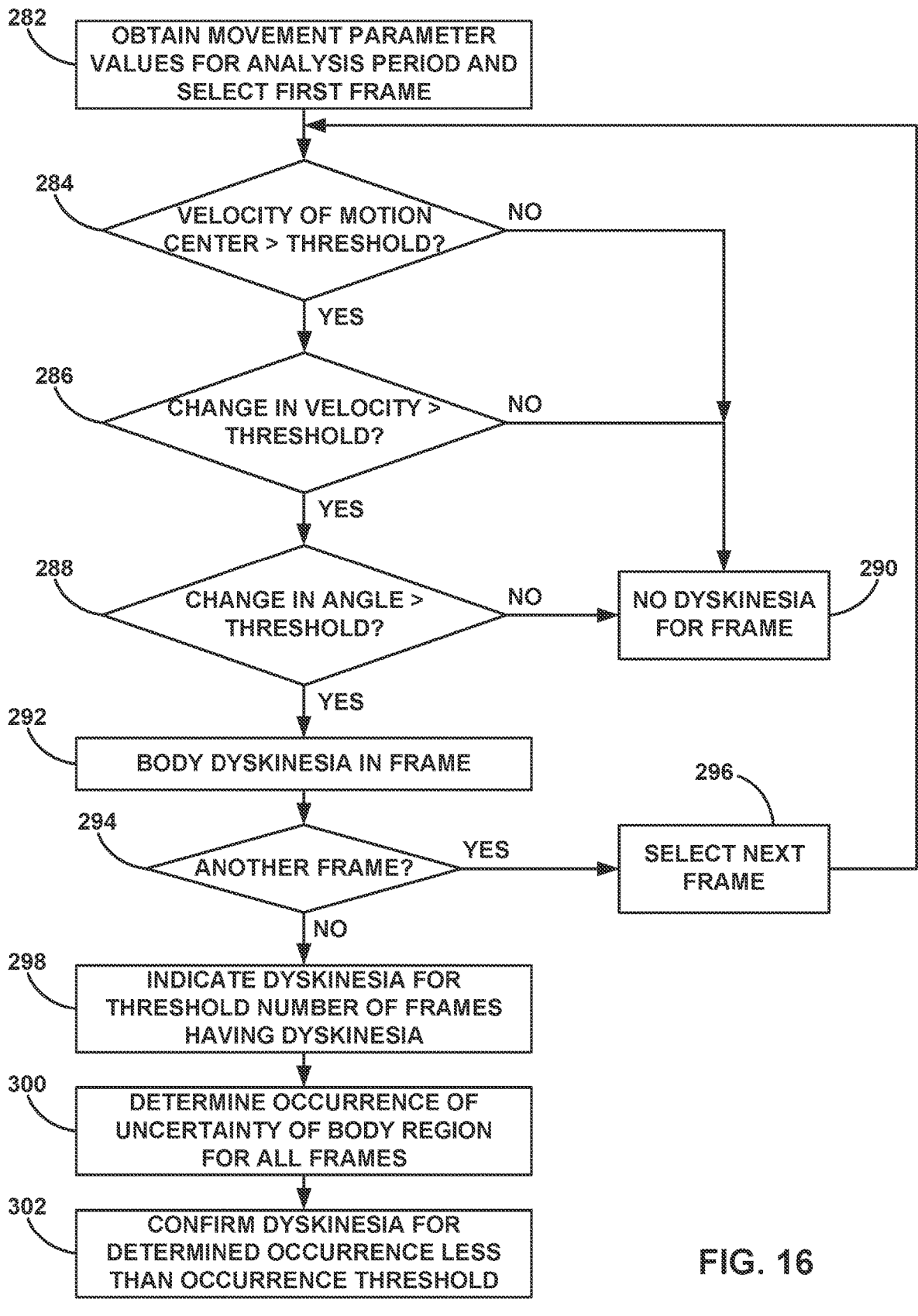
FIG. 16 is a flow diagram that illustrates an example process for identifying dyskinesia in a body of a patient.

FIG. 16 is a flow diagram that illustrates an example process for identifying dyskinesia in a body of a patient. As shown in FIG. 16, processors 80 may obtain the movement parameter values for the analysis period and select a first frame (282). For example, the movement parameter values may be calculated according to the process of FIG. 12 for a sample area corresponding to a body area such as torso 16. Processors 80 may compare the velocity of the motion center to a velocity threshold (284), compare the change in velocity to a change threshold (286), and compare the change in velocity angle to an angle threshold (288). If processors 80 determine that at least one of one or more motion centers within the respective frame have a velocity greater than a velocity threshold (284), a velocity change greater than a velocity change threshold (286), and a velocity angle greater than a velocity angle threshold (288), processors 80 may indicate, based on the determination, that dyskinesia occurred in the respective frame (292). If processors 80 determine that at least one of one or more motion centers within the respective frame have a velocity less than a velocity threshold (284), a velocity change less than a velocity change threshold (286), and a velocity angle less than a velocity angle threshold (288), processors 80 may indicate, based on the determination, that no dyskinesia was identified within the frame (290).

If processors 80 determine that there is another frame to analyze ("YES" branch of block 294), processors 80 may select the next frame (296) and compare the movement parameter values to their respective thresholds. If processors 80 determine that there are no other frames to be analyzed ("NO" branch of block 294). Processors 80 may identify dyskinesia, or determine that dyskinesia occurred, when dyskinesia has been identified in more than a threshold number of frames (298). Processors 80 may also determine an uncertainty of the respective areas corresponding to the anatomical region occurred at a frequency less than an uncertainty occurrence threshold (300). In response to determining that dyskinesia was identified in a threshold number of frames and that the occurrence uncertainty was less than the uncertainty occurrence threshold, processors 80 may confirm and identify that dyskinesia occurred for the anatomical region (such as a torso region) during the period of time in which video information was captured (302). The process of FIG. 16 may include various criteria for identifying the patient behavior of dyskinesia. Each of the thresholds may be user-selected, device-selected, or predefined.

Figure 17:
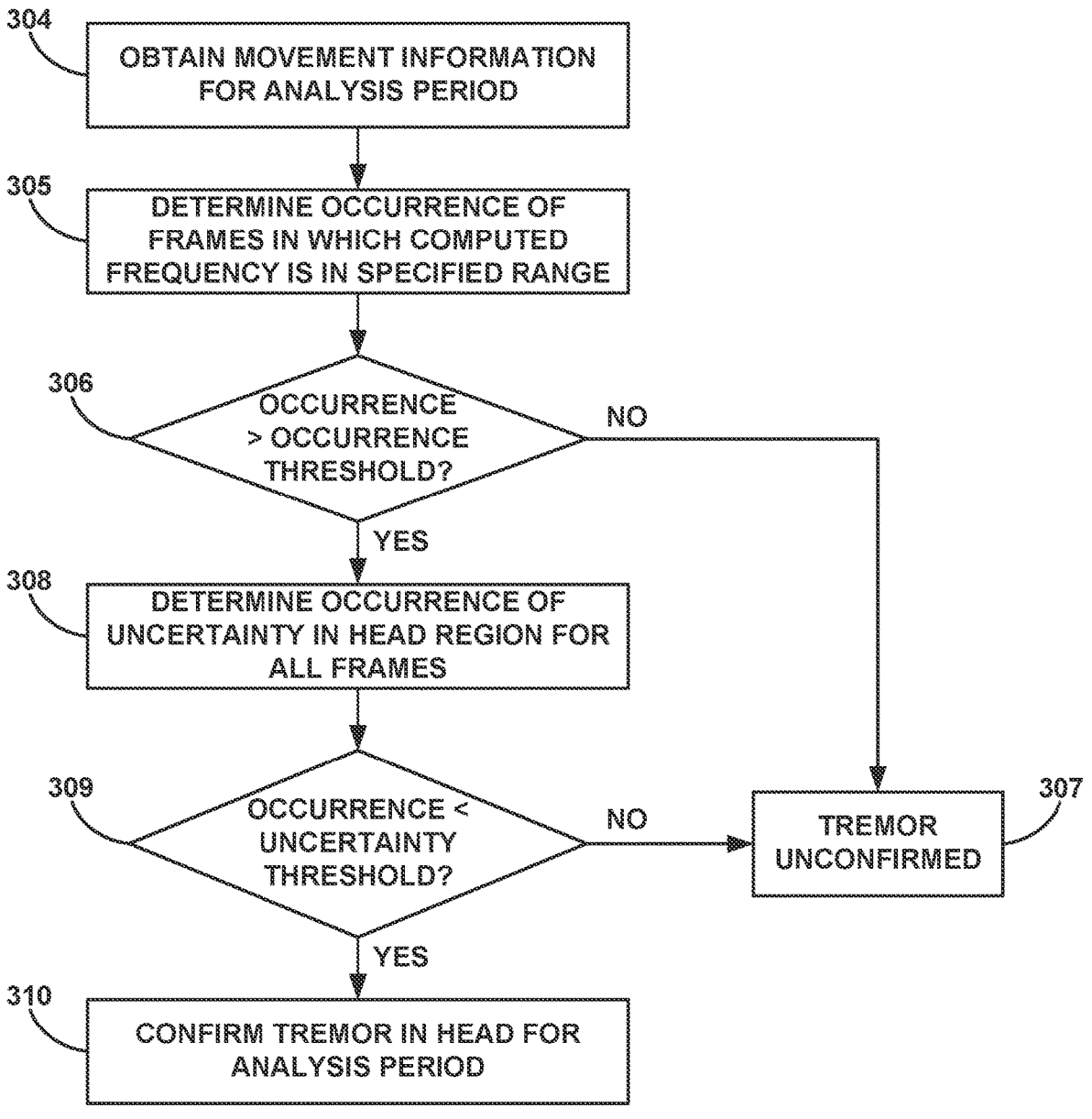
FIG. 17 is a flow diagram that illustrates an example process for identifying tremor in a patient.

FIG. 17 is a flow diagram that illustrates an example process for identifying tremor in a patient. The process of FIG. 17 may require the movement information, or movement parameter values, calculated to determine the frequency with which the patient was moving in the period of time the video information was captured. As shown in FIG. 17, processors 80 may obtain the movement information for the analysis period (304). The movement information may include the calculated movement parameter values described in FIG. 13. For example, processors 80 may be configured to apply a fast Fourier transform (FFT) to the real motion pixels of the frame to generate amplitude spectrums in a frequency domain, select three frequencies having the highest amplitude spectrums in the frequency domain, select, based on the comparison, one of the three frequencies that falls within a predetermined range of frequencies and has the highest amplitude spectrum of the three frequencies, and store the selected one of the three frequencies as a detected frequency for the respective frame. Processors 80 may perform this frequency analysis on each of the frames with real motion pixels.

Processors 80 may then determine the occurrence of frames in which the detected or computed frequency is within the specified range (305). In other words, this step may include a determination of the occurrence with which a subset of frames includes the detected frequency that falls within the specified, or predetermined, frequency range. If the occurrence of the frames is less than an occurrence threshold ("NO" branch of block 306), processors 80 may determine that there is no tremor and that the tremor is unconfirmed (307). If the occurrence of frames is greater than the occurrence threshold ("YES" branch of block 306), processors 80 may determine an occurrence of the uncertainty of the respective areas (such as the uncertainty of the head region) corresponding to the anatomical region for the frames of the period of time (308). This occurrence may be the frequency at which the uncertainty is greater than a threshold for each frame.

If the occurrence of the uncertainty in each frame is greater than an uncertainty occurrence threshold ("NO" branch of block 309), processors 80 will determine that the tremor is unconfirmed and not present (307). If the occurrence of the uncertainty in each frame is less than the uncertainty occurrence threshold ("YES" branch of block 309), processors 80 may be configured to confirm that the behavior of tremor was present in the frames of the analysis period (310). In this manner, processors 80 may identify tremor as at least one patient behavior that occurred during the period in response to determining the occurrence of the specified frequency exceeded the occurrence threshold and the uncertainty was less than the uncertainty occurrence threshold.

Each of the processes described herein may be performed on the same video information 50 such that multiple different patient behaviors may be assessed on the same video frames. In this manner, processors 80 may be configured to identify different behaviors present in the same frames and/or same patient motions. For example, processors 80 may perform the processes of FIGS. 14-17 on the same video frames. Although dyskinesia, bradykinesia, and tremor are described herein as some predetermined patient behaviors to be identified from the video information, other patient behaviors (e.g., dystonia, rigidity, restless leg syndrome, etc.) may be identified in other examples using similar techniques. Each of the thresholds herein may be based on at least one of the type of behavior to be identified, asymptomatic movement parameter values, clinician experience, other patient data, individual patient history, patient age, currently delivered therapies, or any other related input.

In some examples, processors 80 and/or additional devices may be configured to process the video data in multiple ways to identify a single patient behavior. For instance, processors 80 may process the video data to identify tremor according to the examples above. Processors 80 may also process the same video data to identify whether the tremor occurred during patient movement, as may be determined by determining whether a velocity of a motion center of one or more body regions of the patient is greater than a threshold. An entire body region of the patient may be used to determine whether the patient is moving between two different areas of the video frame, such as between two different locations within the room where the patient resides. Processor 80 may utilize both the frequency and velocity information obtained from the video data to identify whether the patient behavior relates to tremor during rest (e.g., the patient is stationary) or tremor during motion (e.g., the patient is ambulatory).

The behaviors identifiable by processors 80 described above are some examples, but processors 80 may be configured to identify any number of alternative or additional patient behaviors. For example, processors 80 may be configured to define behaviors associated with a patient's gait, vertical stability, postural stability, posture symmetry, arm-swing size, overall body rigidity, overall poverty movement (e.g., lack of movement), whether the patient is experiencing passive motion, and any other such behaviors. Processors 80 may define behaviors associated with any one or more parts of the patient's body. For instance, behaviors associated with facial features, such as lip movement or tongue manipulation, may be defined by processors 80 from the video data.

In some cases, processors 80 may be configured to define one or more behaviors associated with multiple parts of the patient's body.

Figure 18:
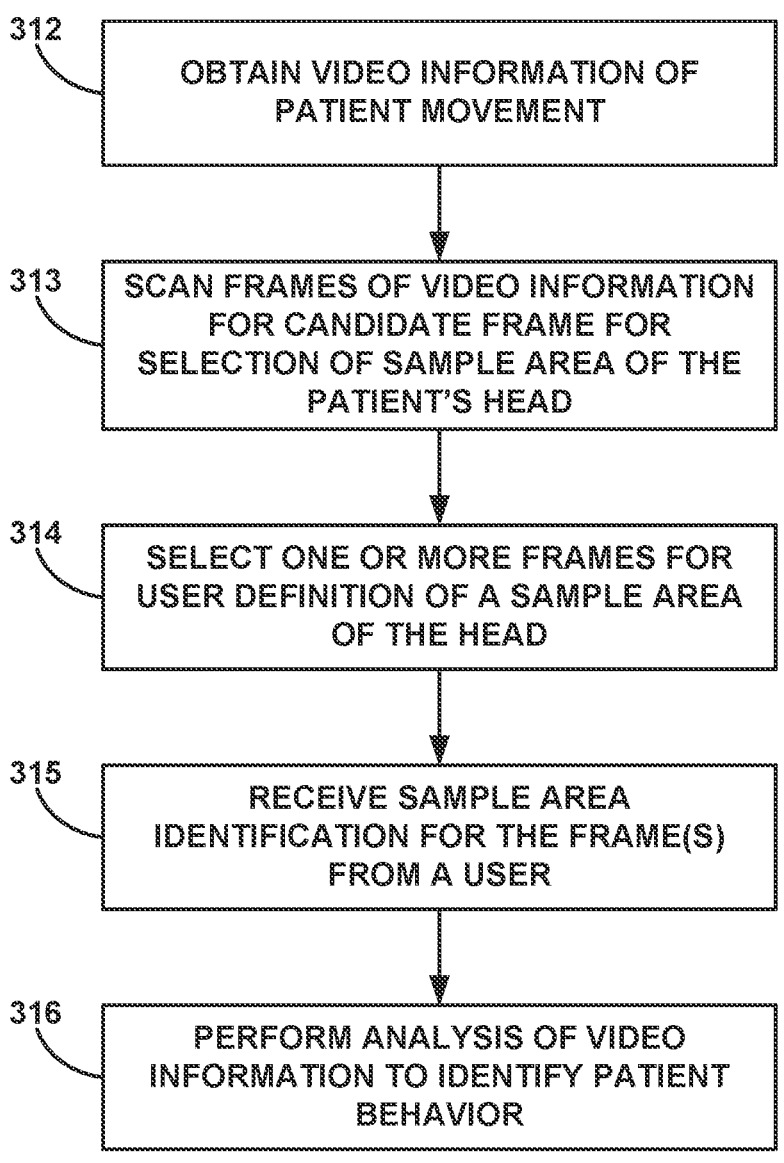
FIG. 18 is a flow diagram that illustrates an example process for suggesting one or more frames of the video information in which to define a sample area of an anatomical region of the patient.

FIG. 18 is a flow diagram that illustrates an example process for suggesting one or more frames of video information 50 in which to define a sample area of an anatomical region of patient 12. The process of FIG. 18 may be performed by processors 80 in order to present candidate video frames that may be suitable for defining a sample area. In some examples, the process of FIG. 18 may be used to identify two or more sample areas within the plurality of frames within the video information when patient 12 may have moved positions or otherwise changed how one or more anatomical regions can be viewed. In this manner, processors 80 may identify potential problematic frames for analyzing patient motion and may present candidate frames intended to resolve any analysis issues before the analysis is even performed.

As shown in FIG. 18, processors 80 may obtain video information 50 of patient movement (312). Processors 80 may then scan the plurality of frames for one or more candidate frames having the anatomical region and for selection (or defining) a sample area of the anatomical region (313). For example, the anatomical region may be head 14 of patient 12. Processors 80 may select, based on the scan, one or more candidate frames to be presented for user definition of respective sample areas (314). Processors 80 may identify frames in which certain areas change dramatically or frames associated with a continuous chain of frames including a similar area.

Processors 80 may output the one or more candidate frames for presentation to a user (e.g., clinician 22). After the user defines one or more sample areas, processors 80 may receive the sample area identification for the respective frames (315). In response to receiving the sample areas, processors 80 may perform the analysis of the video information and included frames to identify the occurrence of any patient behavior within the captured video information (316). In some examples, processes 80 may select one or more candidate frames in response to identifying a group of frames (e.g., consecutive frames) in which calculated uncertainty levels exceed an uncertainty threshold or other issues with the analysis arise.

As described herein, a networked server 44 or any other computing device may perform one or more processes to identify patient behavior from video information captured of patient 12. These identified patient behaviors may be used to diagnose movement disorders or underlying diseases and/or or monitor the progression of such disorders. In addition, the identified patient behaviors may be used to control or improve the delivery of therapy to patient 12. For example, the identified patient behavior may be used as direct feedback used to control therapy delivery. In another example, the identified patient behavior may be used to calibrate other sensors that provide sensed patient parameter values used as feedback in controlling therapy. The types of therapy that may be controlled include electrical stimulation therapy, drug delivery therapy, and/or oral medication prescriptions.

Figure 19:
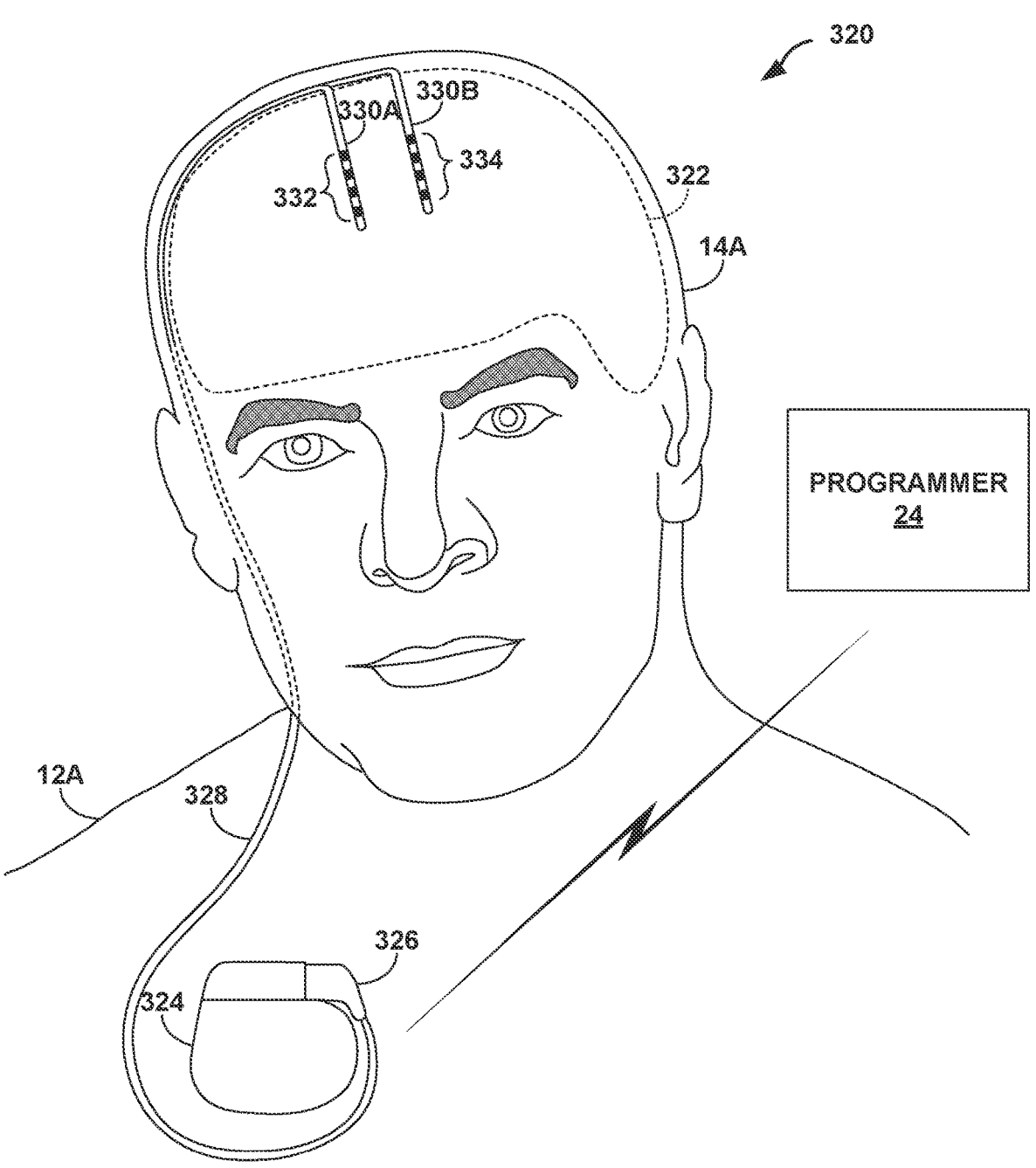
FIG. 19 is a conceptual diagram illustrating an example system that includes an implantable medical device (IMD) configured to deliver deep brain stimulation to a patient.

FIG. 19 is a conceptual diagram illustrating example system 320 that includes implantable medical device (IMD) 324 configured to deliver deep brain stimulation to patient 12A. Patient 12A may be patient 12A of FIGS. 1 and 2 or a different patient. System 320 may be configured to treat a patient condition, such as a movement disorder, neurodegenerative impairment, a mood disorder or a seizure disorder of patient 12A. Patient 12A ordinarily will be a human patient. In some cases, however, therapy system 320 may be applied to other mammalian or non-mammalian, non-human patients. While movement disorders and neurodegenerative impairment are primarily referred to herein, in other examples, therapy system 320 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 320 includes medical device programmer 24, implantable medical device (IMD) 324, lead extension 328, and leads 330A and 330B with respective sets of electrodes 332, 334. In the example shown in FIG. 19, electrodes 332, 334 of leads 330A, 330B are positioned to deliver electrical stimulation to a tissue site within brain 322, such as a deep brain site under the dura mater of brain 322 of patient 12A. In some examples, delivery of stimulation to one or more regions of brain 322, such as the subthalamic nucleus, globus pallidus or thalamus, may be an effective treatment to manage movement disorders, such as Parkinson's disease. Electrodes 332, 334 are also positioned to sense bioelectrical brain signals within brain 322 of patient 12A. In some examples, some of electrodes 332, 334 may be configured to sense bioelectrical brain signals and others of electrodes 332, 334 may be configured to deliver electrical stimulation to brain 322. In other examples, all of electrodes 332, 334 are configured to both sense bioelectrical brain signals and deliver electrical stimulation to brain 322.

IMD 324 includes a therapy module that includes a stimulation generator that generates and delivers electrical stimulation therapy to patient 12A via a subset of electrodes 332, 334 of leads 330A and 330B, respectively. The subset of electrodes 332, 334 that are used to deliver electrical stimulation to patient 12A, and, in some cases, the polarity of the subset of electrodes 332, 334, may be referred to as a stimulation electrode combination. As described in further detail below, the stimulation electrode combination can be selected for a particular patient 12A and target tissue site (e.g., selected based on the patient condition) based on one or more frequency domain characteristics of a bioelectrical brain signal (e.g., a patient parameter) that is sensed by one or more groups of electrodes 332, 334 that are associated with the stimulation electrode combination. The group of electrodes 332, 334 includes at least one electrode and can include a plurality of electrodes. In some examples, the bioelectrical signals sensed within brain 322 may reflect changes in electrical current produced by the sum of electrical potential differences across brain tissue. Examples of bioelectrical brain signals include, but are not limited to, electrical signals generated from local field potentials (LFP) sensed within one or more regions of brain 322, such as an electroencephalogram (EEG) signal, or an electrocorticogram (ECoG) signal. Local field potentials, however, may include a broader genus of electrical signals within brain 322 of patient 12A. Each of these signals may be correlated or calibrated with the identified patient behavior and used for feedback in controlling the delivery of therapy.

In some examples, the bioelectrical brain signals that are used to select a stimulation electrode combination may be sensed within the same region of brain 322 as the target tissue site for the electrical stimulation. As previously indicated, these tissue sites may include tissue sites within the thalamus, subthalamic nucleus or globus pallidus of brain 322, as well as other target tissue sites. The specific target tissue sites and/or regions within brain 322 may be selected based on the patient condition. Thus, in some examples, both a stimulation electrode combination and sense electrode combinations may be selected from the same set of electrodes 332, 334. In other examples, the electrodes used for delivering electrical stimulation may be different than the electrodes used for sensing bioelectrical brain signals.

Electrical stimulation generated by IMD 324 may be configured to manage a variety of disorders and conditions. In some examples, the stimulation generator of IMD 324 is configured to generate and deliver electrical pulses to patient 12A via electrodes of a selected stimulation electrode combination. However, in other examples, the stimulation generator of IMD 324 may be configured to generate and deliver a continuous wave signal, e.g., a sine wave or triangle wave. In either case, a signal generator within IMD 324 may generate the electrical stimulation therapy for DBS according to a therapy program that is selected at that given time in therapy. In examples in which IMD 324 delivers electrical stimulation in the form of stimulation pulses, a therapy program may include a set of therapy parameter values, such as a stimulation electrode combination for delivering stimulation to patient 12A, pulse frequency, pulse width, and a current or voltage amplitude of the pulses. As previously indicated, the stimulation electrode combination may indicate the specific electrodes 332, 334 that are selected to deliver stimulation signals to tissue of patient 12A and the respective polarity of the selected electrodes.

IMD 324 may be implanted within a subcutaneous pocket above the clavicle, or, alternatively, the abdomen, back or buttocks of patient 12A, on or within cranium 32 or at any other suitable site within patient 12A. Generally, IMD 324 is constructed of a biocompatible material that resists corrosion and degradation from bodily fluids. IMD 324 may comprise a hermetic housing to substantially enclose components, such as a processor, therapy module, and memory.

As shown in FIG. 19, implanted lead extension 328 is coupled to IMD 324 via connector 30 (also referred to as a connector block or a header of IMD 324). In the example of FIG. 19, lead extension 328 traverses from the implant site of IMD 324 and along the neck of patient 12A to cranium 32 of patient 12A to access brain 322. In the example shown in FIG. 19, leads 330A and 330B (collectively "leads 330") are implanted within the right and left hemispheres, respectively, of patient 12A in order deliver electrical stimulation to one or more regions of brain 322, which may be selected based on the patient condition or disorder controlled by therapy system 320. The specific target tissue site and the stimulation electrodes used to deliver stimulation to the target tissue site, however, may be selected, e.g., according to the identified patient behaviors and/or other sensed patient parameters. Other lead 20 and IMD 324 implant sites are contemplated. For example, IMD 324 may be implanted on or within cranium 14A, in some examples. Or leads 330 may be implanted within the same hemisphere or IMD 324 may be coupled to a single lead.

Although leads 330 are shown in FIG. 19 as being coupled to a common lead extension 328, in other examples, leads 330 may be coupled to IMD 324 via separate lead extensions or directly to connector 326. Leads 330 may be positioned to deliver electrical stimulation to one or more target tissue sites within brain 322 to manage patient symptoms associated with a movement disorder of patient 12A. Leads 330 may be implanted to position electrodes 332, 334 at desired locations of brain 322 through respective holes in cranium 32. Leads 330 may be placed at any location within brain 322 such that electrodes 332, 334 are capable of providing electrical stimulation to target tissue sites within brain 322 during treatment. For example, electrodes 332, 334 may be surgically implanted under the dura mater of brain 322 or within the cerebral cortex of brain 322 via a burr hole in cranium 32 of patient 12A, and electrically coupled to IMD 324 via one or more leads 330.

Example techniques for delivering therapy to manage a movement disorder are described in U.S. Patent Application Publication No. 2009/0099627 by Molnar et al., entitled, "THERAPY CONTROL BASED ON A PATIENT MOVE-MENT STATE," which was filed on Sep. 25, 2008, which is incorporated herein by reference in its entirety. In some examples described by U.S. Patent Application Publication No. 2009/0099627 by Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12A initiate movement or maintain movement, and upon detecting a rest state of patient 12A, therapy delivery may be deactivated or otherwise modified.

In the example shown in FIG. 19, electrodes 332, 334 of leads 330 are shown as ring electrodes. Ring electrodes may be used in DBS applications because they are relatively simple to program and are capable of delivering an electrical field to any tissue adjacent to electrodes 332, 334. In other examples, electrodes 332, 334 may have different configurations. For example, in some examples, at least some of the electrodes 332, 334 of leads 330 may have a complex electrode array geometry that is capable of producing shaped electrical fields. The complex electrode array geometry may include multiple electrodes (e.g., partial ring or segmented electrodes) around the outer perimeter of each lead 330, rather than one ring electrode. In this manner, electrical stimulation may be directed in a specific direction from leads 330 to enhance therapy efficacy and reduce possible adverse side effects from stimulating a large volume of tissue. In some examples, a housing of IMD 324 may include one or more stimulation and/or sensing electrodes. In alternative examples, leads 330 may have shapes other than elongated cylinders as shown in FIG. 19. For example, leads 330 may be paddle leads, spherical leads, bendable leads, or any other type of shape effective in treating patient 12A and/or minimizing invasiveness of leads 330.

In the example shown in FIG. 19, IMD 324 includes a memory (shown in FIG. 21) to store a plurality of therapy programs that each define a set of therapy parameter values. In some examples, IMD 324 may select a therapy program from the memory based on various parameters, such as sensed patient parameters and the identified patient behaviors. IMD 324 may generate electrical stimulation based on the selected therapy program to manage the patient symptoms associated with a movement disorder.

External programmer 24 wirelessly communicates with IMD 324 as needed to provide or retrieve therapy information. Programmer 24 is an external computing device (e.g., computing device 54 of FIG. 3) that the user, e.g., clinician 22 and/or patient 12A, may use to communicate with IMD 324. For example, programmer 24 may be a clinician programmer that the clinician uses to communicate with IMD 324 and program one or more therapy programs for IMD 324. Alternatively, programmer 24 may be a patient programmer that allows patient 12A to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 324.

When programmer 24 is configured for use by the clinician, programmer 24 may be used to transmit initial programming information to IMD 324. This initial information may include hardware information, such as the type of leads 330 and the electrode arrangement, the position of leads 330 within brain 322, the configuration of electrode array 332, 334, initial programs defining therapy parameter values, and any other information the clinician desires to program into IMD 324. Programmer 24 may also be capable of completing functional tests (e.g., measuring the impedance of electrodes 332, 334 of leads 330).

The clinician may also store therapy programs within IMD 324 with the aid of programmer 24. During a programming session, the clinician may determine one or more therapy programs that may provide efficacious therapy to patient 12A to address symptoms associated with the patient condition, and, in some cases, specific to one or more different patient states, such as a sleep state, movement state or rest state. For example, the clinician may select one or more stimulation electrode combination with which stimulation is delivered to brain 322. During the programming session, patient 12A may provide feedback to the clinician as to the efficacy of the specific program being evaluated or the clinician may evaluate the efficacy based on one or more physiological parameters of patient 12A (e.g., muscle activity or muscle tone). Alternatively, the identified patient behavior from video information 50 may be used as feedback during the initial, and subsequent programming sessions. Programmer 24 may assist the clinician in the creation/identification of therapy programs by providing a methodical system for identifying potentially beneficial therapy parameter values.

Programmer 24 may also be configured for use by patient 12A. When configured as a patient programmer, programmer 24 may have limited functionality (compared to a clinician programmer) in order to prevent patient 12A from altering critical functions of IMD 324 or applications that may be detrimental to patient 12A. In this manner, programmer 24 may only allow patient 12A to adjust values for certain therapy parameters or set an available range of values for a particular therapy parameter.

Programmer 24 may also provide an indication to patient 12A when therapy is being delivered, when patient input has triggered a change in therapy or when the power source within programmer 24 or IMD 324 needs to be replaced or recharged. For example, programmer 24 may include an alert LED, may flash a message to patient 12A via a programmer display, generate an audible sound or somatosensory cue to confirm patient input was received, e.g., to indicate a patient state or to manually modify a therapy parameter.

Therapy system 320 may be implemented to provide chronic stimulation therapy to patient 12A over the course of several months or years. However, system 320 may also be employed on a trial basis to evaluate therapy before committing to full implantation. If implemented temporarily, some components of system 320 may not be implanted within patient 12A. For example, patient 12A may be fitted with an external medical device, such as a trial stimulator, rather than IMD 324. The external medical device may be coupled to percutaneous leads or to implanted leads via a percutaneous extension. If the trial stimulator indicates DBS system 320 provides effective treatment to patient 12A, the clinician may implant a chronic stimulator within patient 12A for relatively long-term treatment.

As described herein, IMD 324 may use identified patient behavior from video information to determine delivery of therapy. For example, one or more processors of IMD 324 may be configured to receive, from a computing device such as networked server 44 or programmer 24, an indication of one or more patient behaviors that occurred during a period of time. These patient behaviors may have been identified from video analysis of the frames capturing the movement of patient 12A. In other words, the patient behavior may be determined by a computing device from video information 50 captured during the period of time. In response to receiving the indication of the patient behavior, IMD 324 may be configured to determine, based on the indication of the patient behavior, a therapy to be delivered to patient 12A. IMD 324 may also output the determination for at least one of delivery of the therapy to patient 12A and display to a user.

For example, IMD 324 may determine the therapy by selecting one or more therapy parameter values (e.g., a set of therapy parameters or a therapy program) that at least partially defines the therapy. In other examples, other computing devices may be configured to determine the therapy based on the identified patient behavior (e.g., movement disorder). For example, networked server 44, programmer 24, or any other computing device may determine the therapy. The therapy may include one or more of electrical stimulation therapy, drug delivery therapy (e.g., drug delivered from an implantable or external drug pump), or oral medication therapy.

In some examples, the therapy may be determined directly from the identified patient behavior. For example, IMD 324 may be configured to select one of a plurality of predetermined therapies, each of the plurality of therapies corresponding to at least one of the plurality of patient behaviors associated with a respective one or more movement parameters generated from video information 50. IMD 324 may store associations between the patient behaviors and predetermined therapies to be delivered upon detection of each behavior. The patient behaviors may be identified continuously, in response to receiving new video information, or on demand from a user. In some examples, programmer 24 may be configured to select the appropriate therapy associated with an identified patient behavior and transmit one or more therapy parameters associated with the patient behavior to IMD 324.

In other examples, the identified patient behaviors may be used as an objective measure of patient movement and to calibrate one or more patient parameters to the identified patient behaviors. IMD 324 may then utilize the calibrated patient parameters as direct feedback to control therapy. For example, networked server 44 may be configured to calculate, from video information 50 captured during a period of time, one or more movement parameters of patient 12A and identify, based on the one or more movement parameters, each of one of a plurality of patient behaviors that occurred during the period of time. Networked server 44 may then obtain values of a patient parameter (e.g., LFP signal or patient accelerations) sensed during the period of time. Networked server 44 may then correlate the values of the patient parameter to each of the one of the plurality of patient behaviors that occurred during the period of time. These patient parameter values may then be associated with respective therapy parameter sets selected to manage the movements of patient 12 in response to subsequent detection of the patient parameter values.

IMD 324 may receive the patient parameter values and associated therapy parameter sets from networked server 44 and store the associations in memory. IMD 324 may then use the sensed patient parameter values as feedback to control therapy delivery. For example, subsequent to the correlation of patient behaviors with the sensed patient parameter values, IMD 324 may be configured to obtain a sensed patient parameter value and identify one or more of the plurality of patient behaviors associated with the sensed patient parameter value. IMD 324 may then determine, based on the identification of the patient behaviors, the therapy to be delivered to the patient. Although networked server 44 was described as performing the correlation between identified patient behaviors and sensed patient parameter values, any other computing device may perform these tasks. For example, programmer 24 and/or IMD 324 may perform the correlations and associations for subsequent feedback.

In some examples, the therapy may be controlled based on feedback from two or more different patient parameters. For example, networked server 44 may be configured to obtain values of a second patient parameter sensed during the period of time and correlate the values of the second patient parameter to each of the one of the plurality of patient behaviors that occurred during the period of time. Subsequently, IMD 324 or programmer 24 may be configured to determine that the values of both the first patient parameter and the second patient parameter are associated with the same patient behavior and identify the same patient behavior as the one or more of the plurality of patient behaviors experienced by patient 12A. In this manner, therapy may be selected only when the values of two or more different patient parameter values indicate the same movement behavior is occurring with patient 12A. Requiring multiple patient parameters as feedback may provide a confirmation and safety check to reduce therapy changes due to false positives.

A variety of different patient parameters may be monitored and used to provide feedback to control stimulation therapy. For example, a patient parameter may be a local field potential (LFP), an electroencephalogram (ECG), an electrogram (EEG), an acceleration of the patient, a relative motion between two locations of the patient, blood pressure, heart rate, patient speech pattern, patient breathing pattern, sleep indication, or a chemical indication. In this manner, one or more sensors may sense a respective patient parameter. IMD 324 may include one or more sensors or be coupled to one or more sensors via lead 328. For example, electrodes 332,334 may be used to sense LFP or ECG signals and an accelerometer or gyroscope may be included within IMD 324 or on lead 328 to sense accelerations or rotations of the patient.

In some examples, video information may be recaptured of patient 12A if therapy is no longer efficacious for patient 12A. For example, programmer 24 may receive user input identifying that the therapy is insufficient even though therapy is being controlled based on previously correlated and calibrated patient parameters or patient behavior. Programmer 24 may transmit an indication of the user input to networked server 44. In response to receiving the indication, networked server 44 may be configured to request capture of supplemental video information of patient motion during a second period of time different than the first period of the previous video information 50. Based on the supplemental video information, networked server 44 may identify any patient behavior within the supplemental video information. Networked server 44 may receive an indication of the patient behavior during the second period and use the patient behavior to determine a different therapy to be delivered to patient 12A based on the indication of the patient behavior during the second period of time. In some examples, networked server 44 may update the correlations or calibrations of the patient parameter values obtained during the second period of time to the newly identified patient behaviors. The updated calibrations may improve the precision with which therapy is directed to patient behavior. Although networked server 44 is described as updating the calibrations of the patient parameters, other devices such as programmer 24 or IMD 324 may perform the updates to the calibrations and/or associations of patient parameter values to therapy parameters.

Although IMD 324 is described as delivering electrical stimulation therapy to brain 322, IMD 324 may be configured to direct electrical stimulation to other anatomical regions of patient 12A. In other examples, system 320 may include an implantable drug pump in addition to, or in place of, electrical stimulator 324. Further, as described in FIG. 20, an IMD may provide other electrical stimulation such as spinal cord stimulation to treat a movement disorder.

Figure 20:
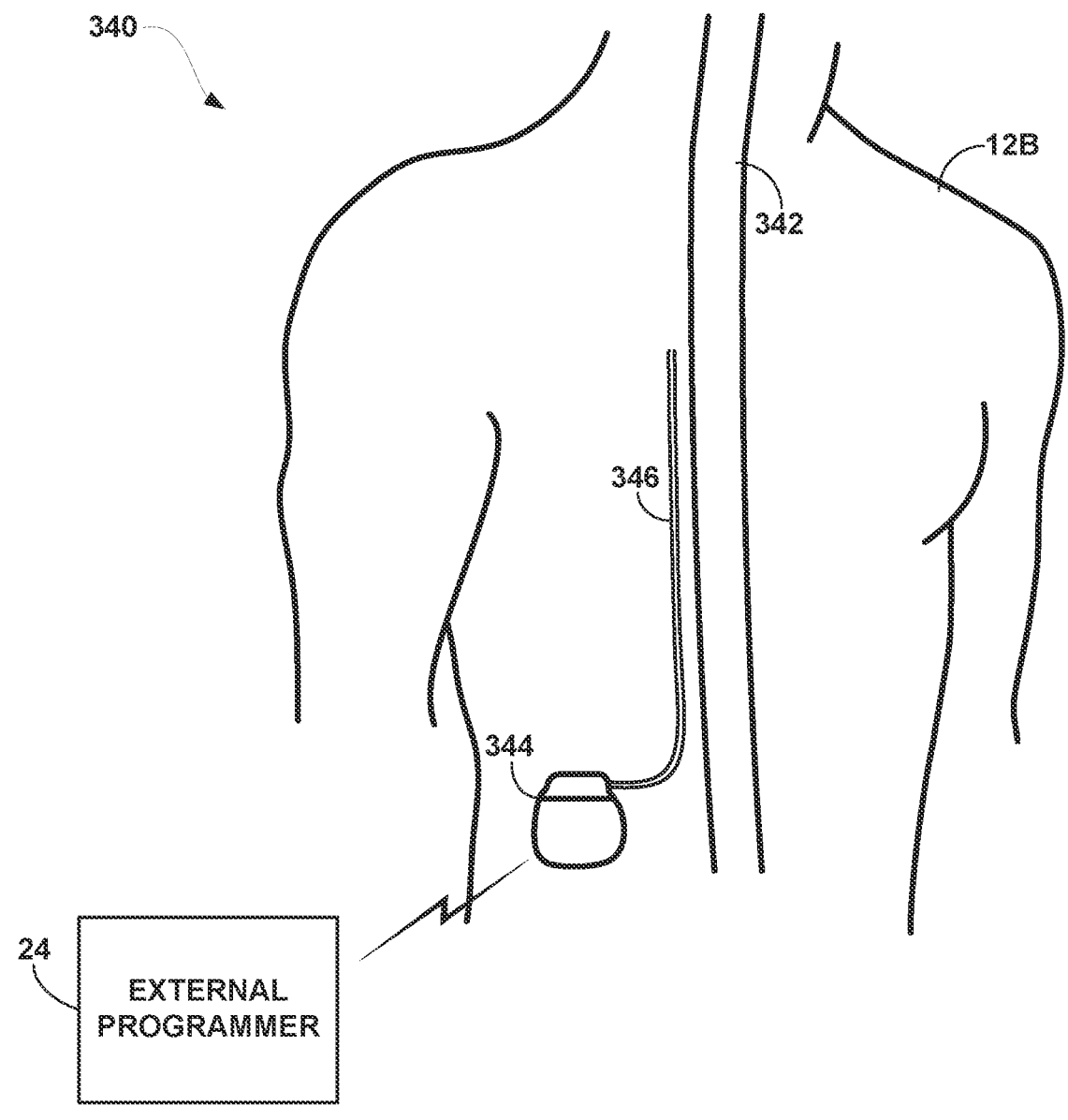
FIG. 20 is a conceptual diagram illustrating an example system that includes an IMD configured to deliver spinal cord stimulation to a patient.

FIG. 20 is a conceptual diagram illustrating example system 340 that includes IMD 344 configured to deliver spinal cord stimulation (SCS) to a patient 12B. Patient 12B may be similar to patient 12A of FIG. 19. System 340 may provide similar therapy and utilize similar feedback (e.g., identified patient behavior and/or sensed patient parameters) to control therapy. In some examples, system 340 may additionally or alternatively be configured to provide peripheral nerve field stimulation (PNFS), occipital nerve stimulation, sacral nerve stimulation (SNS), pelvic floor stimulation, or any other electrical stimulation therapy.

As shown in FIG. 20, system 340 includes an IMD 344 and external programmer 24 shown in conjunction with a patient 12B, who is ordinarily a human patient. In the example of FIG. 20, IMD 344 is an implantable electrical stimulator that delivers neurostimulation therapy to patient 12B, e.g., for relief of chronic pain or other symptoms such as abnormal movements. Generally IMD 344 may be a chronic electrical stimulator that remains implanted within patient 12B for weeks, months, or even years. IMD 344 may be similar to IMD 324 of FIG. 19. In the example of FIG. 20, IMD 344 and lead 346 may be directed to delivering SCS therapy. In other examples, IMD 344 may be a temporary, or trial, stimulator used to screen or evaluate the efficacy of electrical stimulation for chronic therapy. IMD 344 may be implanted in a subcutaneous tissue pocket, within one or more layers of muscle, or other internal location. IMD 344 may be coupled to one or more lead 346.

Electrical stimulation energy, which may be constant current or constant voltage based pulses, for example, is delivered from IMD 344 to one or more targeted locations within patient 12B via one or more electrodes (not shown) of lead 346. The parameters for a program that controls delivery of stimulation energy by IMD 344 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example.

In the example of FIG. 20, lead 346 is disposed within patient 12B, e.g., implanted within patient 12B. Lead 346 tunnels through tissue of patient 12B from along spinal cord 342 to a subcutaneous tissue pocket or other internal location where IMD 344 is disposed. Although lead 346 may be a single lead, lead 346 may include a lead extension or other segments that may aid in implantation or positioning of lead 346. In addition, a proximal end of lead 346 may include a connector (not shown) that electrically couples to a header of IMD 344. Although only one lead 346 is shown in FIG. 20, system 340 may include two or more leads, each coupled to IMD 344 and directed to similar or different target tissue sites. For example, multiple leads may be disposed along spinal cord 342 or leads may be directed to spinal cord 342 and/or other locations within patient 12B.

Lead 346 may carry one or more electrodes that are placed adjacent to the target tissue, e.g., spinal cord 342 for spinal cord stimulation (SCS) therapy. One or more electrodes may be disposed at or near a distal tip of lead 346 and/or at other positions at intermediate points along lead 346, for example. Electrodes of lead 346 transfer electrical stimulation generated by an electrical stimulation generator in IMD 344 to tissue of patient 12B. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. In general, ring electrodes arranged at different axial positions at the distal ends of lead 346 will be described for purposes of illustration.

Similar to IMD 324 of FIG. 19, IMD 344 delivers electrical stimulation therapy to patient 12B via selected combinations of electrodes carried by lead 346. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 20, the target tissue for electrical stimulation delivered via lead 346 is tissue proximate spinal cord 342 (e.g., one or more target locations of the dorsal columns or one or more dorsal roots that branch from spinal cord 342). Lead 346 may be introduced into spinal cord 342 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 342 and to the brain of the patient. Patient 12B may perceive the interruption of pain signals as a reduction in pain and, therefore, efficacious therapy results. For treatment of other disorders, lead 346 may be introduced at any exterior location of patient 12B.

Although lead 346 is described as generally delivering or transmitting electrical stimulation signals, lead 346 may additionally transmit electrical signals obtained via electrodes or various sensors carried by the lead from patient 12B to IMD 344 for monitoring. For example, IMD 344 may utilize detected nerve impulses or muscle impulses to diagnose the condition of patient 12B or adjust the delivered stimulation therapy. Lead 346 may thus transmit electrical signals to and from patient 12B.

A user, such as a clinician or patient 12B, may interact with a user interface of an external programmer 24 to program IMD 344. Programming of IMD 344 may refer generally to the generation and transfer of commands, programs, or other information to control the operation of IMD 344. In this manner, IMD 344 may receive the transferred commands and programs from programmer 24 to control stimulation therapy. For example, external programmer 24 may transmit programs, parameter adjustments, program selections, group selections, user input, or other information to control the operation of IMD 344, e.g., by wireless telemetry or wired connection.

IMD 344 may be constructed of any polymer, metal, or composite material sufficient to house the components of IMD 344 (e.g., components illustrated in FIG. 22) within patient 12B. In this example, IMD 344 may be constructed with a biocompatible housing, such as titanium or stainless steel, or a polymeric material such as silicone or polyurethane, and surgically implanted at a site in patient 12B near the pelvis, abdomen, or buttocks. The housing of IMD 344 may be configured to provide a hermetic seal for components, such as a rechargeable power source. In addition, the housing of IMD 344 may be selected of a material that facilitates receiving energy to charge rechargeable power source 18.

As described herein, information may be transmitted between external programmer 24 and IMD 344. Therefore, IMD 344 and programmer 24 may communicate via wireless communication using any techniques known in the art. Examples of communication techniques may include, for example, radiofrequency (RF) telemetry and inductive coupling, but other techniques are also contemplated. In some examples, programmer 24 may include a communication head that may be placed proximate to the patient's body near the IMD 344 implant site in order to improve the quality or security of communication between IMD 344 and programmer 24. Communication between programmer 24 and IMD 344 may occur during power transmission or separate from power transmission.

Although IMD 344 is generally described in FIG. 20, techniques of this disclosure may also be applicable to external or partially external medical device in other examples. For example, IMD 344 may instead be configured as an external medical device coupled to one or more percutaneous medical leads. The external medical device may be a chronic, temporary, or trial electrical stimulator. In addition, an external electrical stimulator may be used in addition to one or more IMDs 344 to deliver electrical stimulation described herein.

Figure 21:
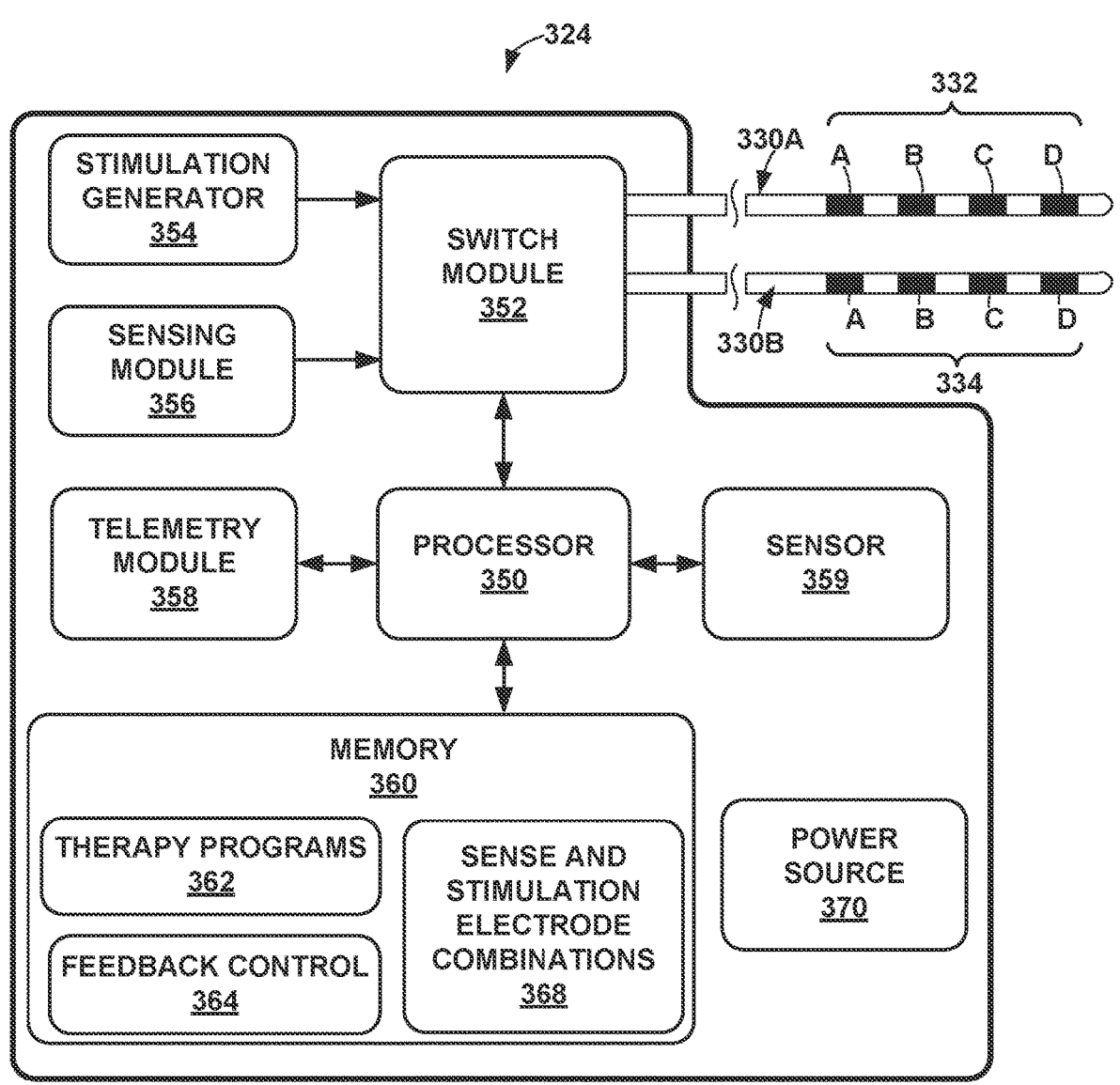
FIG. 21 is a block diagram of the example IMD of FIG. 19 for delivering deep brain stimulation therapy.

FIG. 21 is a block diagram of the example IMD 324 of FIG. 19 for delivering deep brain stimulation therapy. In the example shown in FIG. 21, IMD 324 includes processor 350, memory 360, stimulation generator 354, sensing module 356, switch module 352, telemetry module 358, sensor 359, and power source 370. Memory 360 may include any volatile or non-volatile media, such as a random access memory (RAM), read only memory (ROM), non-volatile RAM (NVRAM), electrically erasable programmable ROM (EEPROM), flash memory, and the like. Memory 360 may store computer-readable instructions that, when executed by processor 350, cause IMD 324 to perform various functions. Memory 360 may be a storage device or other non-transitory medium.

In the example shown in FIG. 21, memory 360 stores therapy programs 362, sense electrode combinations and associated stimulation electrode combinations 368, and feedback control 364 in separate memories within memory 360 or separate areas within memory 360. Each stored therapy program 362 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 368 stores sense electrode combinations and associated stimulation electrode combinations. As described above, in some examples, the sense and stimulation electrode combinations may include the same subset of electrodes 332, 334, or may include different subsets of electrodes. Thus, memory 360 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 350. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 322 in order to mitigate any irregular oscillations or other irregular brain activity within the tissue site associated with the sense electrode combination.

Feedback control 364 may include instructions that determine what feedback to use when controlling therapy delivery such as which therapy programs, therapy parameter sets, or individual therapy parameter values to select. Feedback control 364 may include associations of identified patient behaviors from video information to respective therapy parameter sets intended to treat the identified patient behaviors. In addition, or alternatively, feedback control 364 may include associations of values for one or more sensed patient parameters (e.g., LFP signals or patient accelerations) to respective therapy parameter sets. The values of the sensed patient parameters may be calibrated or correlated with identified patient behaviors from captured video information. In any case, IMD 324 may use the instructions within feedback control 364 to adjust the therapy delivered to patient 12A.

Stimulation generator 354, under the control of processor 350, generates stimulation signals for delivery to patient 12A via selected combinations of electrodes 332, 334. An example range of electrical stimulation parameters believed to be effective in DBS to manage a movement disorder of patient include:

1. Frequency: between approximately 100 Hz and approximately 500 Hz, such as approximately 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milli-Amps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 354 generates electrical stimulation signals in accordance with the electrical stimulation parameters noted above. Other ranges of therapy parameter values may also be useful, and may depend on the target stimulation site within patient 12A. While stimulation pulses are described, stimulation signals may be of any form, such as continuous-time signals (e.g., sine waves) or the like.

In each of the examples described herein, if stimulation generator 354 shifts the delivery of stimulation energy between two therapy programs, processor 350 of IMD 324 may provide instructions that cause stimulation generator 354 to time-interleave stimulation energy between the electrode combinations of the two therapy programs, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs may be used, in other examples.

Processor 350 may include any one or more of a microprocessor, a controller, a digital signal processor (DSP), an application specific integrated circuit (ASIC), a field-programmable gate array (FPGA), discrete logic circuitry, and the functions attributed to processor 350 herein may be embodied as firmware, hardware, software or any combination thereof. Processor 350 controls stimulation generator 354 according to therapy programs 54 stored in memory 360 to apply particular stimulation parameter values specified by one or more of programs, such as amplitude, pulse width, and pulse rate.

In the example shown in FIG. 21, the set of electrodes 332 includes electrodes 332A, 332B, 332C, and 332D, and the set of electrodes 334 includes electrodes 334A, 334B, 334C, and 334D. Processor 350 also controls switch module 352 to apply the stimulation signals generated by stimulation generator 354 to selected combinations of electrodes 332, 334. In particular, switch module 352 may couple stimulation signals to selected conductors within leads 330, which, in turn, deliver the stimulation signals across selected electrodes 332, 334. Switch module 352 may be a switch array, switch matrix, multiplexer, or any other type of switching module configured to selectively couple stimulation energy to selected electrodes 332, 334 and to selectively sense bioelectrical brain signals with selected electrodes 332, 334. Hence, stimulation generator 354 is coupled to electrodes 332, 334 via switch module 352 and conductors within leads 330. In some examples, however, IMD 324 does not include switch module 352.

Stimulation generator 354 may be a single channel or multi-channel stimulation generator. In particular, stimulation generator 354 may be capable of delivering a single stimulation pulse, multiple stimulation pulses, or a continuous signal at a given time via a single electrode combination or multiple stimulation pulses at a given time via multiple electrode combinations. In some examples, however, stimulation generator 354 and switch module 352 may be configured to deliver multiple channels on a time-interleaved basis. For example, switch module 352 may serve to time divide the output of stimulation generator 354 across different electrode combinations at different times to deliver multiple programs or channels of stimulation energy to patient 12A.

Although sensing module 356 is incorporated into a common housing with stimulation generator 354 and processor 350 in FIG. 21, in other examples, sensing module 356 may be in a separate housing from IMD 324 and may communicate with processor 350 via wired or wireless communication techniques. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 322 of patient 12A.

Sensor 359 may include one or more sensing elements that sense values of a respective patient parameter. For example, sensor 359 may include one or more accelerometers, optical sensors, chemical sensors, temperature sensors, pressure sensors, or any other types of sensors. Sensor 359 may output patient parameter values that may be used as feedback to control delivery of therapy. Feedback control 364 may include instructions for processor 350 on how to utilize the signals or values provided by sensor 359. IMD 324 may include additional sensors within the housing of IMD 324 and/or coupled via one of leads 330 or other leads. In addition, IMD 324 may receive sensor signals wirelessly from remote sensors via telemetry module 358, for example. In some examples, one or more of these remote sensors may be external to patient (e.g., carried on the external surface of the skin, attached to clothing, or otherwise positioned external to the patient). Each of the sensor signals may be calibrated by identified patient behavior from video information and incorporated in the feedback control of therapy.

Telemetry module 358 supports wireless communication between IMD 324 and an external programmer 24 or another computing device under the control of processor 350. Processor 350 of IMD 324 may receive, as updates to programs, values for various stimulation parameters such as amplitude and electrode combination, from programmer 24 via telemetry module 358. The updates to the therapy programs may be stored within therapy programs 362 portion of memory 360. Telemetry module 358 in IMD 324, as well as telemetry modules in other devices and systems described herein, such as programmer 24, may accomplish communication by radiofrequency (RF) communication techniques. In addition, telemetry module 358 may communicate with external medical device programmer 24 via proximal inductive interaction of IMD 324 with programmer 24. Accordingly, telemetry module 358 may send information to external programmer 24 on a continuous basis, at periodic intervals, or upon request from IMD 324 or programmer 24.

Power source 370 delivers operating power to various components of IMD 324. Power source 370 may include a small rechargeable or non-rechargeable battery and a power generation circuit to produce the operating power. Recharging may be accomplished through proximal inductive interaction between an external charger and an inductive charging coil within IMD 324. In some examples, power requirements may be small enough to allow IMD 324 to utilize patient motion and implement a kinetic energy-scavenging device to trickle charge a rechargeable battery. In other examples, traditional batteries may be used for a limited period of time.

Throughout the disclosure, a group of electrodes may refer to any electrodes located at the same position along the longitudinal axis of one or more leads. A group of electrodes may include one or more electrodes.

Figure 22:
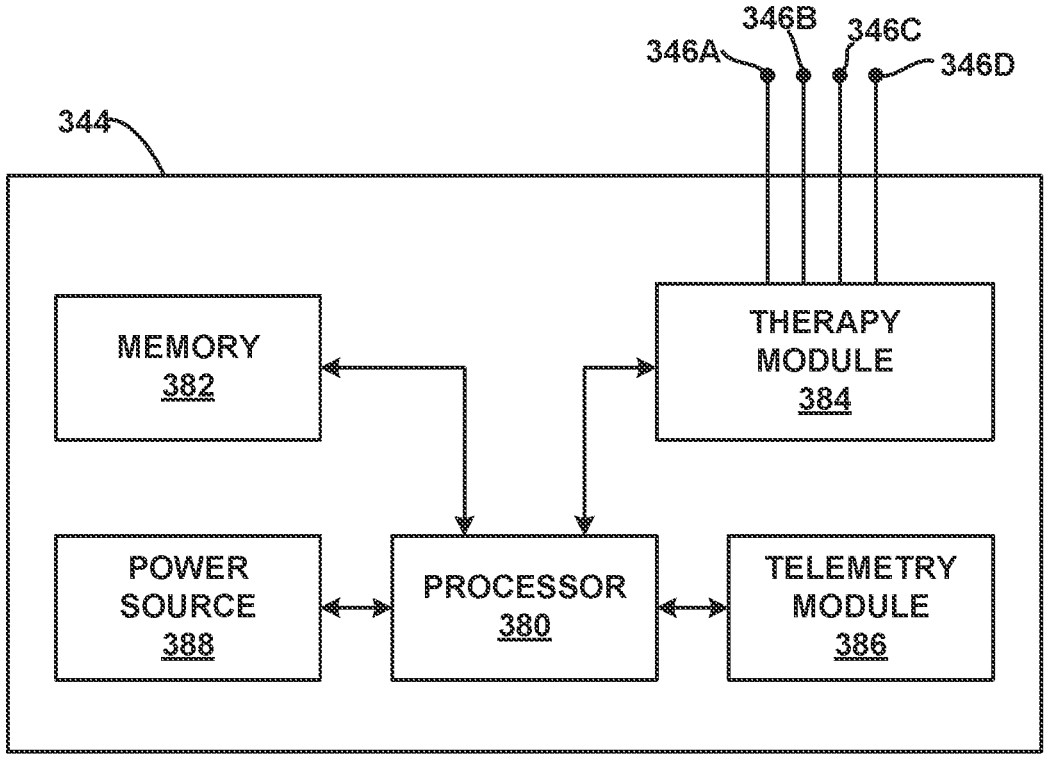
FIG. 22 is a block diagram of the example IMD of FIG. 20 for delivering spinal cord stimulation therapy.

FIG. 22 is a block diagram of example IMD 344 of FIG. 20 for delivering spinal cord stimulation therapy. IMD 344 may be similar to IMD 324 of FIG. 21, such as providing similar feedback function for controlling SCS therapy. As shown in the example of FIG. 22, IMD 344 includes processor 380, therapy module 384, power source 388, memory 382, and telemetry module 386. In other examples, IMD 344 may include a greater or fewer number of components. For example, IMD 344 may also include one or more sensors such as sensor 359 of FIG. 21.

In general, IMD 344 may comprise any suitable arrangement of hardware, alone or in combination with software and/or firmware, to perform the various techniques described herein attributed to IMD 344 and processor 380. In various examples, IMD 344 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 344 also, in various examples, may include a memory 382, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 380, therapy module 384, and telemetry module 386 are described as separate modules, in some examples, processor 380, therapy module 384, and telemetry module 386 may be functionally integrated. In some examples, processor 380, therapy module 384, and telemetry module 386 may correspond to individual hardware units, such as ASICs, DSPs, FPGAs, or other hardware units.

Memory 382 (e.g., a storage device) may store therapy programs or other instructions that specify therapy parameter values for the therapy provided by therapy module 384 and IMD 344. In some examples, memory 382 may also store instructions for communication between IMD 344 and programmer 24, or any other instructions required to perform tasks attributed to IMD 344. Memory 382 may also store feedback control instructions similar to feedback control 364 of IMD 324.

Generally, therapy module 384 may generate and deliver electrical stimulation under the control of processor 380. In some examples, processor 380 controls therapy module 384 by accessing memory 382 to selectively access and load at least one of the stimulation programs to therapy module 384. For example, in operation, processor 380 may access memory 382 to load one of the stimulation programs to therapy module 384. In such examples, relevant stimulation parameters may include a voltage amplitude, a current amplitude, a pulse frequency, a pulse width, a duty cycle, one or more spatial electrode movement patterns that define the combination of electrodes 346A, 346B, 346C, and 346D that therapy module 384 uses to deliver the electrical stimulation signal. Although therapy module 384 may be configured to generate and deliver electrical stimulation therapy via one or more of electrodes 346A, 346B, 346C, and 346D of lead 346, a different therapy module may be configured to provide different therapy to patient 12B, such as drug delivery therapy via a catheter. These and other therapies may be provided by IMD 344.

An exemplary range of electrical stimulation parameters that may be used to deliver effective treatment for chronic pain, e.g., when applied to spinal cord 342, are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz. Pulse frequencies greater than 1,000 Hz may be considered to be greater than the nerve firing potential of affected nerve fibers to inhibit nerve firing. For example, the pulse frequency may be between approximately 1,000 Hz and 10,000 Hz.

Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between approximately 0.1 milliamps (mA) and 50 mA. In other examples, current amplitude may be between approximately 1.0 mA and 10 mA.

Pulse Width: between about 10 microseconds and 5000 microseconds. In some examples, the pulse width may be between approximately 100 microseconds and 1000 microseconds or between approximately 180 microseconds and 450 microseconds. With higher frequency pulses, the pulse width may be smaller to accommodate the increased frequency. For example, the pulse width may be between approximately 10 microseconds and 50 microseconds.

IMD 344 also includes components to receive power from programmer 24 or a separate charging device to recharge a batter of power source 388. Power source 388 may include one or more capacitors, batteries, or other energy storage devices. IMD 344 may thus also include an inductive coil and a recharge module (both not shown) configured to manage the recharging session for power source 388. Although inductive coupling may be used to recharge power source 388, other wireless energy transfer techniques may alternatively be used. Alternatively, power source 388 may not be rechargeable.

Processor 380 may also control the exchange of information with programmer 24 using telemetry module 386. Telemetry module 386 may be configured for wireless communication using radio frequency protocols or inductive communication protocols. Telemetry module 386 may include one or more antennas configured to communicate with programmer 24, for example. Processor 380 may transmit operational information and receive therapy programs or therapy parameter adjustments via telemetry module 386. Also, in some examples, IMD 344 may communicate with other implanted devices, such as stimulators, control devices, or sensors, via telemetry module 386. For example, telemetry module 386 may receive user input, spatial electrode movement patterns, or other commands from programmer 24.

Figure 23:
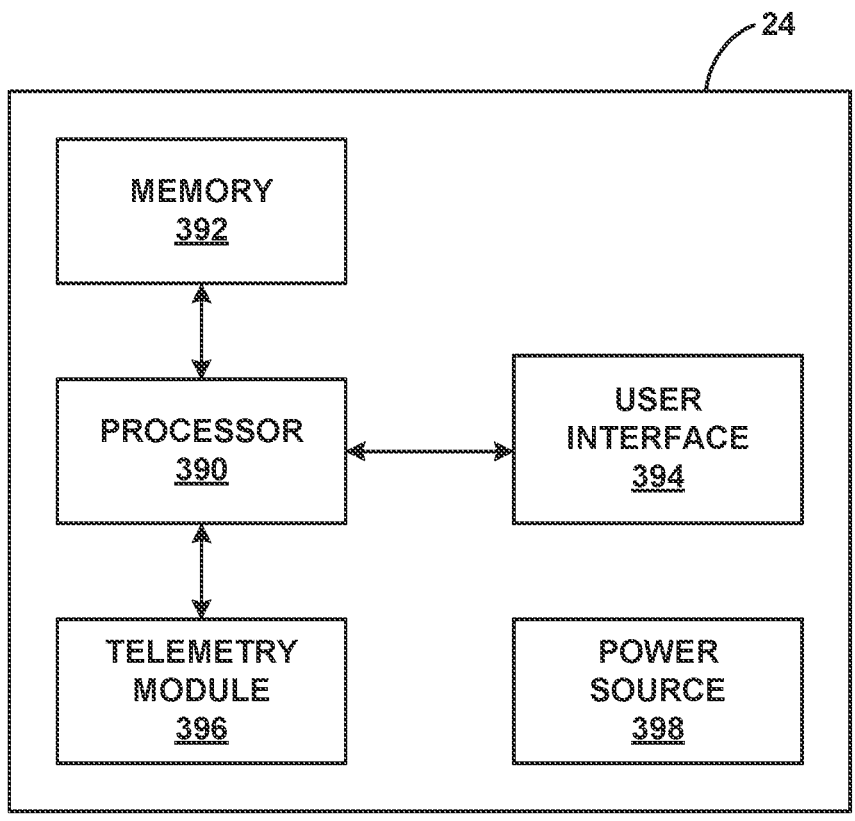
FIG. 23 is a block diagram of the external programmer of FIGS. 1, 19, and 20.

FIG. 23 is a block diagram of external programmer 24 of FIGS. 1, 19, and 20. Although programmer 24 may generally be described as a hand-held device, programmer 24 may be a larger portable device or a more stationary device. In addition, in other examples, programmer 24 may be included as part of an external charging device or include the functionality of an external charging device. As illustrated in FIG. 23, programmer 24 may include a processor 390, memory 392, user interface 394, telemetry module 396, and power source 398. Memory 392 may store instructions that, when executed by processor 390, cause processor 390 and external programmer 24 to provide the functionality ascribed to external programmer 24 throughout this disclosure. For example, processor 390 may be configured to select therapy parameters in response to receiving an indication of an identified patient behavior from video information 50 captured from patient 12 and/or receiving sensed patient parameter values calibrated to be representative of patient behavior.

In general, programmer 24 comprises any suitable arrangement of hardware, alone or in combination with software and/or firmware, to perform the techniques attributed to programmer 24, and processor 390, user interface 394, and telemetry module 396 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 392, such as RAM, ROM, PROM, EPROM, EEPROM, flash memory, a hard disk, a CD-ROM, comprising executable instructions for causing the one or more processors to perform the actions attributed to them. Moreover, although processor 390 and telemetry module 396 are described as separate modules, in some examples, processor 390 and telemetry module 396 are functionally integrated. In some examples, processor 390 and telemetry module 396 correspond to individual hardware units, such as ASICs, DSPs, FPGAs, or other hardware units.

Memory 392 (e.g., a storage device) may store instructions that, when executed by processor 390, cause processor 390 and programmer 24 to provide the functionality ascribed to programmer 24 throughout this disclosure. For example memory 392 may include instructions that cause processor 390 to obtain a parameter set from memory, select a spatial electrode movement pattern, or receive a user input and send a corresponding command to IMD 14, or instructions for any other functionality. In addition, memory 392 may include a plurality of programs, where each program includes a parameter set that defines stimulation therapy User interface 394 may include a button or keypad, lights, a speaker for voice commands, a display, such as a liquid crystal (LCD), light-emitting diode (LED), or organic light-emitting diode (OLED). In some examples the display may be a touch screen. User interface 394 may be configured to display any information related to the delivery of stimulation therapy, identified patient behaviors, sensed patient parameter values, patient behavior criteria, or any other such information. User interface 394 may also receive user input via user interface 394. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry module 396 may support wireless communication between IMD 14 and programmer 24 under the control of processor 390. Telemetry module 396 may also be configured to communicate with another computing device via wireless communication techniques, or direct communication through a wired connection. In some examples, telemetry module 396 may be substantially similar to telemetry module 358 of IMD 324 described herein, providing wireless communication via an RF or proximal inductive medium. In some examples, telemetry module 396 may include an antenna, which may take on a variety of forms, such as an internal or external antenna.

Examples of local wireless communication techniques that may be employed to facilitate communication between programmer 24 and IMD 324 include RF communication according to the 802.11 or Bluetooth specification sets or other standard or proprietary telemetry protocols. In this manner, other external devices may be capable of communicating with programmer 24 without needing to establish a secure wireless connection. As described herein, telemetry module 396 may be configured to transmit a spatial electrode movement pattern or other stimulation parameter values to IMD 324 for delivery of stimulation therapy.

In some examples, selection of therapy parameters or therapy programs may be transmitted to a medical device (e.g., IMD 324 or IMD 344) for delivery to patient 12. In other examples, the therapy may include medication, activities, or other instructions that patient 12 must perform themselves or a caregiver perform for patient 12. For example, in response to receiving an indication of an identified patient behavior or sensed patient parameter value, processor 390 may select a medication and/or dosage of the medication to treat the movement disorder. Processor 390 may control user interface 394 to display such information to the user. In some examples, programmer 24 may provide visual, audible, and/or tactile notifications that indicate there are new instructions. Programmer 24 may require receiving user input acknowledging that the instructions have been completed in some examples.

In other examples, programmer 24 may be configured to receive user input or indications of user input indicating the type of medication, dosage, and/or time the medication was taken by patient 12. Programmer 24 may create a log of the medications or other therapies manually taken by patient 12 in this manner. In some examples, programmer 24 may adjust electrical stimulation therapy and/or drug delivery therapy based on the medication that patient 12 has consumed. For example, programmer 24 may determine (e.g., adjust or maintain) one or more electrical stimulation therapy parameters based on the indication of the drug dosage taken by patient 12. This adjustment may be made due to physiological alterations of patient 12 by the medication.

Figure 24:
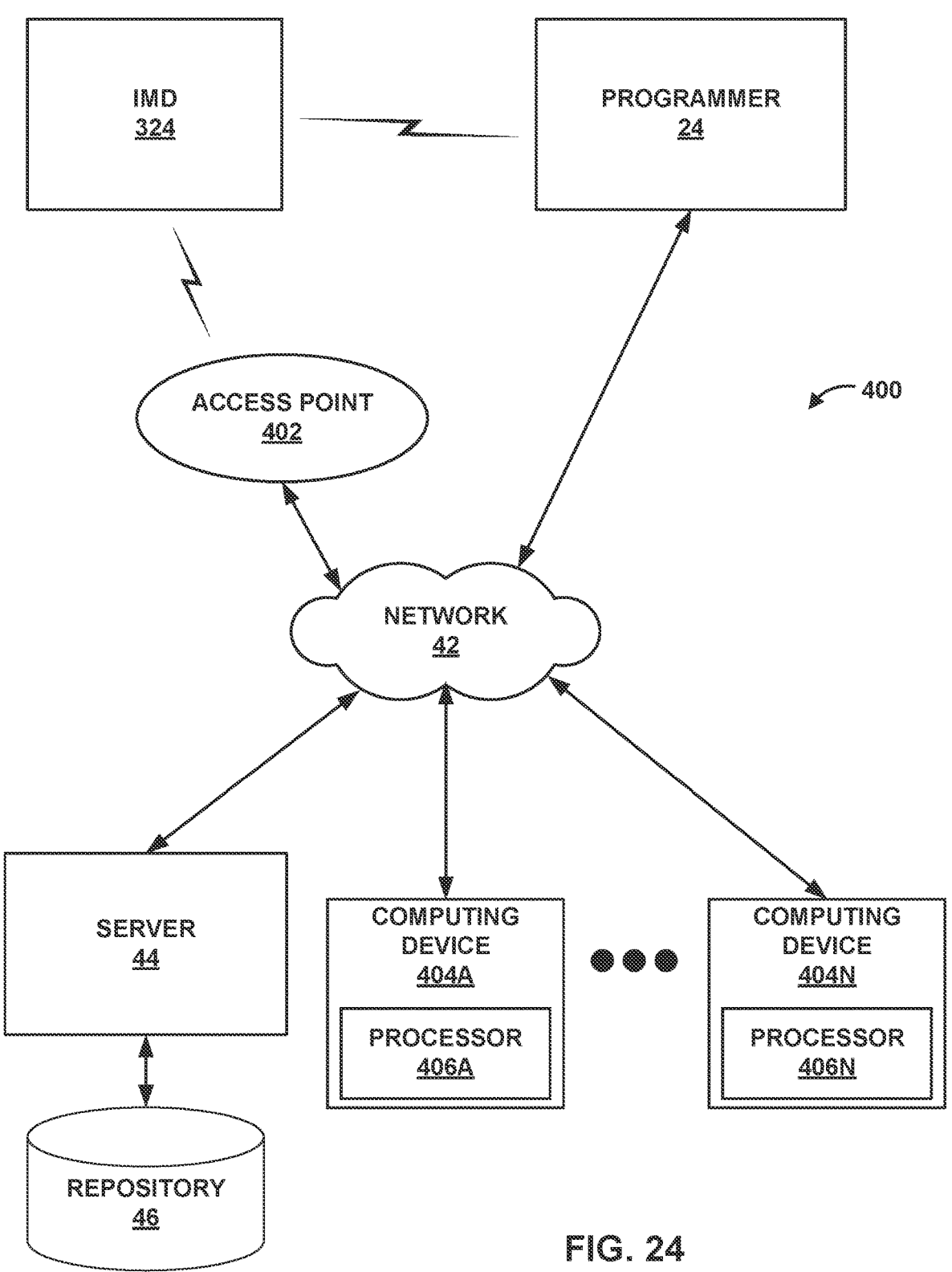
FIG. 24 is a block diagram illustrating an example system that includes a networked server coupled to an IMD and one or more computing devices via a network.

FIG. 24 is a block diagram illustrating example system 400 that includes networked server 44 coupled to IMD 324 (and/or IMD 344) and one or more computing devices 404 via network 42. System 400 may be similar to system 40 of FIG. 3. As shown in FIG. 24, server 44 (e.g., a networked external computing device) and one or more computing devices 404A-404N that are coupled to the IMD 324 and programmer 24 shown in FIG. 19 via a network 42. Network 42 may be generally used to transmit video information 50, behavior information 52, therapy parameter information, or any other data between IMD 324 programmer 24, server 44 and/or computing devices 404.

In some examples, the information transmitted by IMD 324 may allow a clinician or other healthcare professional to monitor patient 12 remotely. In some examples, IMD 324 may use a telemetry module to communicate with programmer 24 via a first wireless connection, and to communicate with access point 402 via a second wireless connection, e.g., at different times. In the example of FIG. 24, access point 402, programmer 24, server 44 and computing devices 404A-404N are interconnected, and able to communicate with each other through network 42. In some cases, one or more of access point 402, programmer 24, server 44 and computing devices 404A-404N may be coupled to network 42 via one or more wireless connections. IMD 324, programmer 24, server 44, and computing devices 404A-404N may each comprise one or more processors, such as one or more microprocessors, DSPs, ASICs, FPGAs, programmable logic circuitry, or the like, that may perform various functions and operations, such as those described herein.

Access point 402 may comprise a device that connects to network 42 via any of a variety of connections, such as telephone dial-up, digital subscriber line (DSL), or cable modem connections. In other examples, access point 402 may be coupled to network 42 through different forms of connections, including wired or wireless connections. In some examples, access point 402 may be co-located with patient 14 and may comprise one or more programming units and/or computing devices (e.g., one or more monitoring units) that may perform various functions and operations described herein. For example, access point 402 may include a home-monitoring unit that is co-located with patient 14 and that may monitor the activity of IMD 324. In some examples, server 44 or computing devices 404 may control or perform any of the various functions or operations described herein.

In some cases, server 44 may be configured to provide a secure storage site for archival of video information, therapy parameters, patient parameters, or other data that has been collected and generated from IMD 324 and/or programmer 24. Network 42 may comprise a local area network, wide area network, or global network, such as the Internet. The system of FIG. 24 may be implemented, in some aspects, with general network technology and functionality similar to that provide by the Medtronic CareLink® Network developed by Medtronic, Inc., of Minneapolis, MN.

Figure 25:
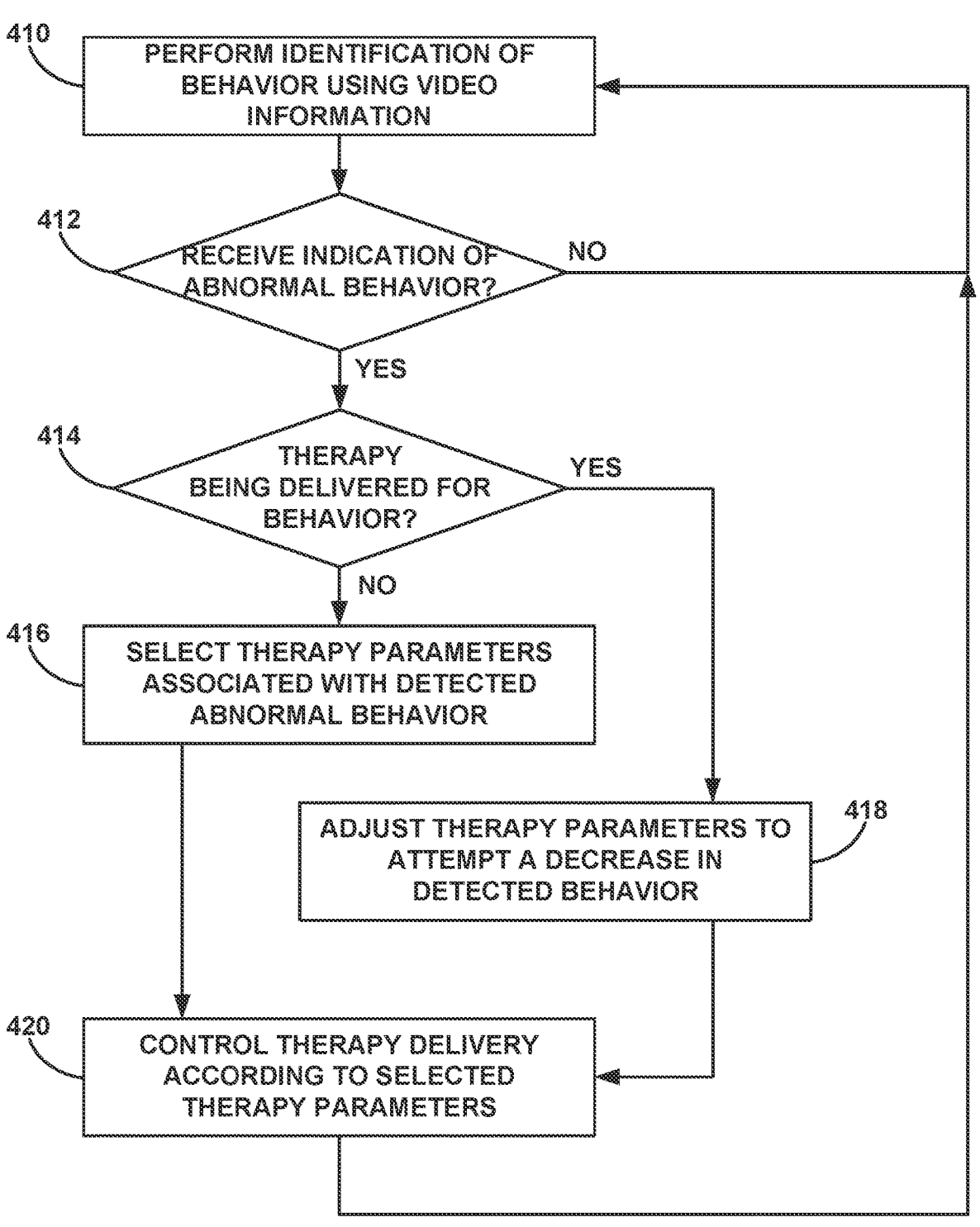
FIG. 25 is a flow diagram illustrating an example process for controlling therapy according to patient behavior identified from video information.

FIG. 25 is a flow diagram illustrating an example process for controlling therapy according to patient behavior identified from video information 50. The process of FIG. 25 will be described with respect to processors 80 of networked server 44 and processor 390 of programmer 24. However, one or more aspects of the process may be performed by other devices such as networked server 44, IMD 324, IMD 344, or computing devices 404.

As shown in FIG. 25, networked server 44 may be configured to perform identification of patient behavior using video information 50 as described herein (410). The identification of patient behavior may be performed as an on-going process to provide feedback for controlling therapy to patient 12A, for example. In other words, video information may be continually, or periodically, capturing new video information of patient 12A. If programmer 24 does not receive any indication of abnormal behavior ("NO" branch of block 412), networked server 44 continues to identify patient behavior (410). If programmer 23 does receive an indication of abnormal behavior ("YES" branch of block 412), programmer 24 checks to determine if therapy is currently being delivered for the identified patient behavior (414).

If therapy is not being delivered to manage the identified therapy ("NO" branch of block 414), programmer 24 may select therapy parameters associated with the detected abnormal behavior (i.e., the identified patient behavior) (416). Programmer 24 may transmit the therapy parameters to IMD 324 such that IMD 324 may control therapy according to the selected therapy parameters (420). If therapy is currently being delivered to manage the identified therapy ("YES" branch of block 414), programmer 24 may adjust one or more therapy parameters to attempt to decrease the severity or presence of the identified behavior (418). Programmer 24 may then transmit the updated therapy parameters to IMD 324 such that IMD 324 may control therapy according to the selected therapy parameters (420).

In some examples, programmer 24 may directly control IMD 324 to deliver therapy according to the selected parameters. In other examples, IMD 324 may select therapy parameters based on the identified patient behavior feedback and control therapy delivery according to the selected therapy parameters instead of programmer 24. Alternatively, networked server 44 may select therapy parameters and/or control therapy delivery. In any case, patient behavior identified from captured video information may be used as feedback to control the delivery of therapy to patient 12A. In addition, therapy parameters may be adjusted if an identified behavior persists even though therapy is currently being delivered to manage the specific identified behavior. This adjustment may be made to improve the efficacy of the delivered therapy.

In other examples, a device (e.g., IMD 324, programmer 24, or networked device 44) may be configured to determine a therapy for a patient from a patient behavior identified from both video information and the values of one or more patient parameters. The patient parameters may be monitored by one or more non-video sensors (e.g., accelerometers, gyroscopes, pressure sensors, or temperature sensors), such that these non-video sensors may generate and transmit a value of the respective patient parameter. Therefore, the values of these patient parameters may be used in combination with video information to identify a behavior of the patient. A device may also use the identified behavior to adjust, select, and/or manage therapy delivered to the patient.

For example, IMD 324 may include one or more processors (e.g., processor 350) configured to obtain one or more values of a patient parameter sensed during the period of time. The value of the patient parameter may, for example, be generated by sensor 359 (e.g., a non-video sensor) or any other non-video sensors. Processor 350 may also obtain video information regarding movement of the patient during the same period of time in which the value of the patient parameter was detected. Processor 350 may then determine, based on video information captured during the period of time and the one or more values of the patient parameter, the patient behavior for the period of time. Responsive to determining the patient behavior, processors 350 may select the appropriate therapy (e.g., select or adjust one or more therapy parameters) for delivery to the patient to treat the determined behavior. In some examples, other devices (e.g., programmer 24 or networked server 44) may contribute to the analysis of the video information, determination of the patient behavior, and/or generation of patient parameter values used to select the appropriate therapy.

Figure 26:
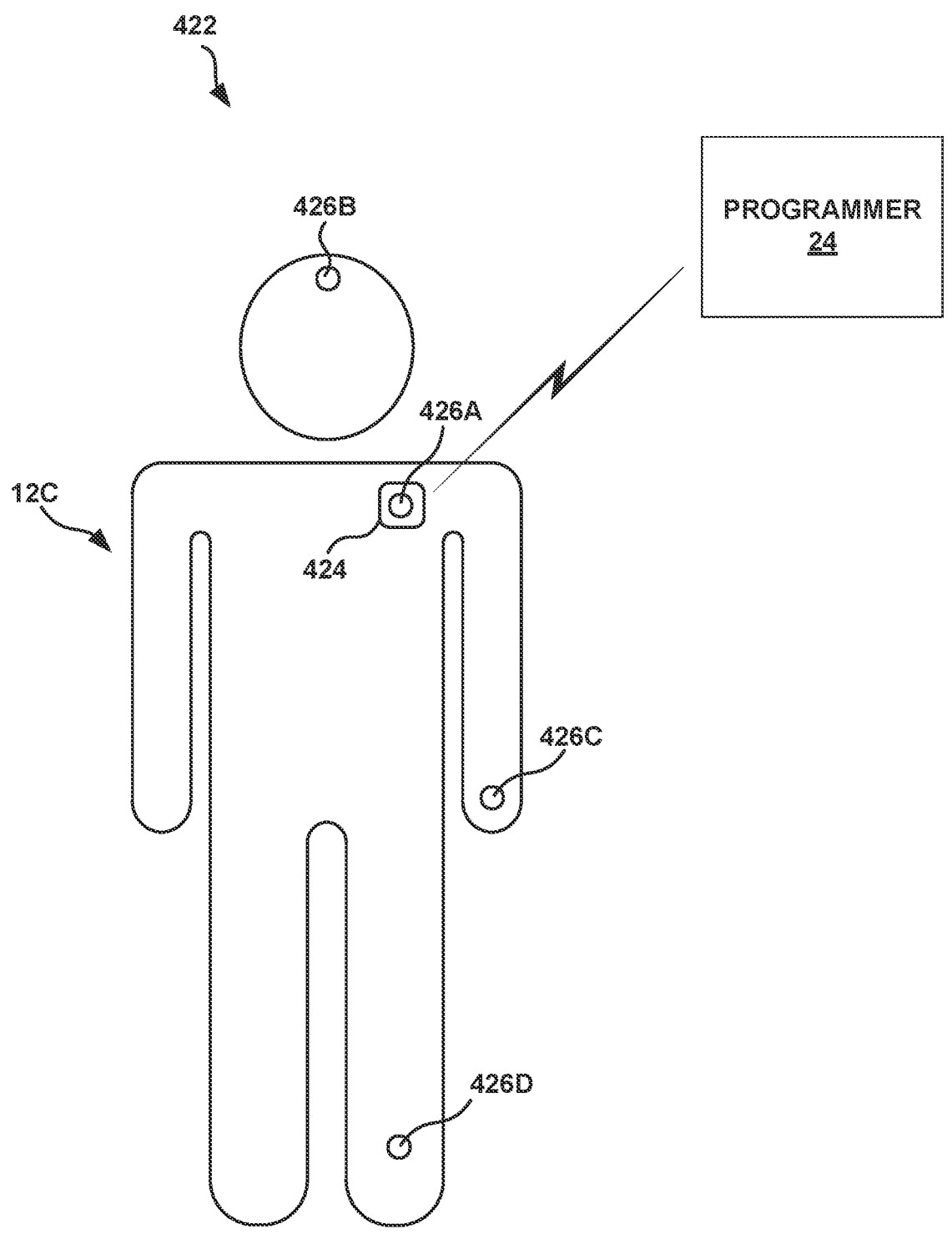
FIG. 26 is a conceptual diagram illustrating an example system that includes sensors configured to sense one or more patient parameters indicative of a patient behavior and monitored to control therapy.

FIG. 26 is a conceptual diagram illustrating example system 422 that includes sensors configured to sense one or more patient parameters indicative of a patient behavior and monitored to control therapy. System 422 includes an implantable medical device (IMD) 424 (e.g., such as IMD 324 or IMD 344) that monitors and/or delivers a therapy to patient 12A. IMD 424 delivers the therapy according to a set of therapy parameters, i.e., a set of values for a number of parameters that define the therapy delivered according to that therapy parameter set, which may also be referred to as a therapy program. In addition, IMD 424 may incorporate the values of sensed patient parameters from one or more sensors located at respective locations of patient 12C (e.g., patient 12). Programmer 24 may be used to communicate with IMD 424 and/or one or more of activity sensors 426.

IMD 424 includes or is coupled to activity sensors 426A-426D (collectively, "activity sensors 426") that detect activity or motion of patient 12A. In one embodiment, activity sensors 426 may comprise accelerometers, gyroscopes, global position system (GPS) units and any other sensors that detect motions of patient 12A. Activity sensors 426 may be multi-axis accelerometers or single-axis accelerometers. As illustrated in FIG. 1, activity sensors 426 may be located at different locations on patient 12A. Activity sensor 426A may, for example, be located on or within a housing of IMD 424. Activity sensor 426B may be located on or within a lead that extends from IMD 424 into the brain of patient 12A. Alternatively, activity sensor 426B may be a stand-alone sensor, i.e., not coupled to any lead, that is located externally or implanted within a head of patient 12A. Activity sensor 426C is located at a limb of patient 12A. In the example illustrated in FIG. 1, activity sensor 426C is located at an arm and, more particularly, at a wrist or hand of patient 12A. Activity sensor 426C may, however, be located on a different limb of patient 12A, such as on the other arm or on a leg. Activity sensors may be worn externally, e.g., on a piece of clothing or a watch, or implanted at the specific locations within patient 12A. Although the example illustrated in FIG. 26 includes three activity sensors, system 422 may include more or less sensors, located at different locations on patient 12C. The techniques of this disclosure may be utilized in any system that includes two or more activity sensors at different locations of patient 12C.

Activity sensors 426 detect activity or motion at respective locations of patient 12C. In particular, as patient 12C moves, activity sensors 426 detect the motion of the respective locations of the body of patient 12C. Activity sensors 426 may, for example, generate signals as a function the motion of the respective portion of the body in terms of magnitude and direction. In the example illustrated in FIG. 26, activity sensor 426A detects motion of a torso of patient 12C, activity sensor 426B detects motion of a head of patient 12C and activity sensor 426C detects motion of the limb of patient 12C.

IMD 424 receives the signals from activity sensors 426. IMD 424 may receive the signals from at least a portion of activity sensors 426 via a wired connection. For example, IMD 424 may receive the signals from activity sensor 426A and 426B, if coupled to a lead, via a wired connection. Alternatively, IMD 424 may receive the signals from at least a portion of activity sensors 426 via wireless telemetry. For example, IMD 424 may receive a signal from activity sensor 426C via wireless telemetry. In this case, activity sensor 426C may include transmit circuitry to transmit the signals to IMD 424. Alternatively, one or more of activity sensors 426 may transmit the signals to a separate monitoring device, which relays the measurements to IMD 424. Activity sensor 426D may be located on a leg or foot of patient 12C.

IMD 424 may analyze the signals from activity sensors 426 to determine when any of the values of the patient parameters indicate a need to control therapy delivery. One or more of the sensed patient parameter values from activity sensors 426 may thus be used to indicate when a patient behavior may be occurring. In some examples, each sensor may provide an individual patient parameter value that is analyzed. In other examples, IMD 424 compares signals of at least two of activity sensors 426 to determine a relative motion between activity sensors 426, and analyzes the relative motion between activity sensors 426. The relative motion represents the manner in which one location of patient 12C moves relative to another location of patient 12C. Using relative motion, therefore, provides a different frame of reference, thus providing for more accurate detection of certain relevant patient motion, such as symptoms of a movement disorder. In this manner one of the patient parameters monitored for indications of patient behavior may be the relative motion between two or more activity sensors 426. In some examples, the relative motions between each pair of activity sensors 426 may be separate patient parameters and calibrated based on the identified patient behavior.

Although four activity sensors 426 are shown in the example of FIG. 26, one, two, three, or more than four activity sensors may be used to provide patient parameter values. Other sensors may also or alternatively be implanted or attached to patient 12C. Such sensors may include temperature sensors, EMG sensors and strain or force gauges to detect muscle movement or flexation, or external electrodes for electrogram generation. In addition, one or more sensors may be located on furniture such as a bed or chair. For example, a hospital bed may include one or more pressure sensors that provide a patient parameter value indicative of patient motion that can be correlated to identified patient behavior from video information captured at the same time. Any and all of these patient parameters may be used as feedback to control therapy delivered to patient 12C.

Figure 27:
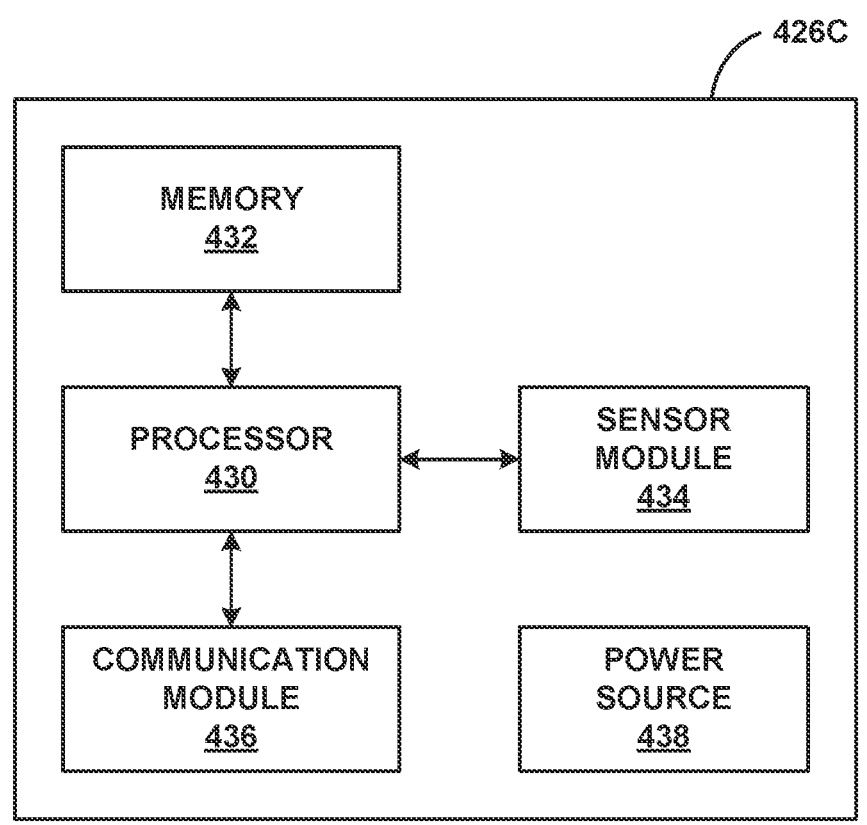
FIG. 27 is a block diagram of an example sensor that senses a patient parameter indicative of patient behavior.

FIG. 27 is a block diagram of an example sensor 426C that senses a patient parameter indicative of patient behavior. Sensor 426C may be similar to sensors 426B, 426D, or any other sensor described herein that may not be included within another device. As illustrated in FIG. 27, sensor 426C may include a processor 430, memory 432, sensor module 434, communication module 436, and power source 438. Memory 432 may store instructions that, when executed by processor 430, cause processor 430 to control the sensing of sensor module 434, communication via communication module 436, and/or the storage and retrieval of data from memory 432.

In general, sensor 426C comprises any suitable arrangement of hardware, alone or in combination with software and/or firmware, to perform the techniques attributed to sensor 426C, and processor 430, sensor module 434, and communication module 436 of sensor 426C. In various examples, sensor 426C may include one or more processors, such as one or more microprocessors, DSPs, ASICs, FPGAs, or any other equivalent integrated or discrete logic circuitry, as well as any combinations of such components. Sensor 426C also, in various examples, may include a memory 432 (e.g., a storage device), such as RAM, ROM, PROM, EPROM, EEPROM, flash memory, a hard disk, a CD-ROM, comprising executable instructions for causing the one or more processors to perform the actions attributed to them. Moreover, although processor 430 and communication module 436 are described as separate modules, in some examples, processor 430 and communication module 436 are functionally integrated. In some examples, processor 430 and communication module 436 correspond to individual hardware units, such as ASICs, DSPs, FPGAs, or other hardware units.

Memory 432 (e.g., a storage device) may store instructions that, when executed by processor 432, cause processor 432 and sensor 426C to provide the functionality ascribed to sensor 426C such as generating values of the patient parameter and transmitting the generated values to another device such as IMD 424 and/or programmer 24. Sensor module 434 may include any components, membranes, devices, etc. configured to translate mechanical, chemical, electromagnetic signal into an electrical signal for use by processor 430. For example, sensor module 434 may include one or more accelerometers that translate mechanical acceleration into an electrical signal representative of the acceleration.

Communication module 436 may support wireless or wired communication according to any protocol known in the art or described herein. Power source 438 may include any rechargeable or non-rechargeable battery, energy scavenging device, or any other such element configured to provide operational power to activity sensor 426C.

Figure 28:
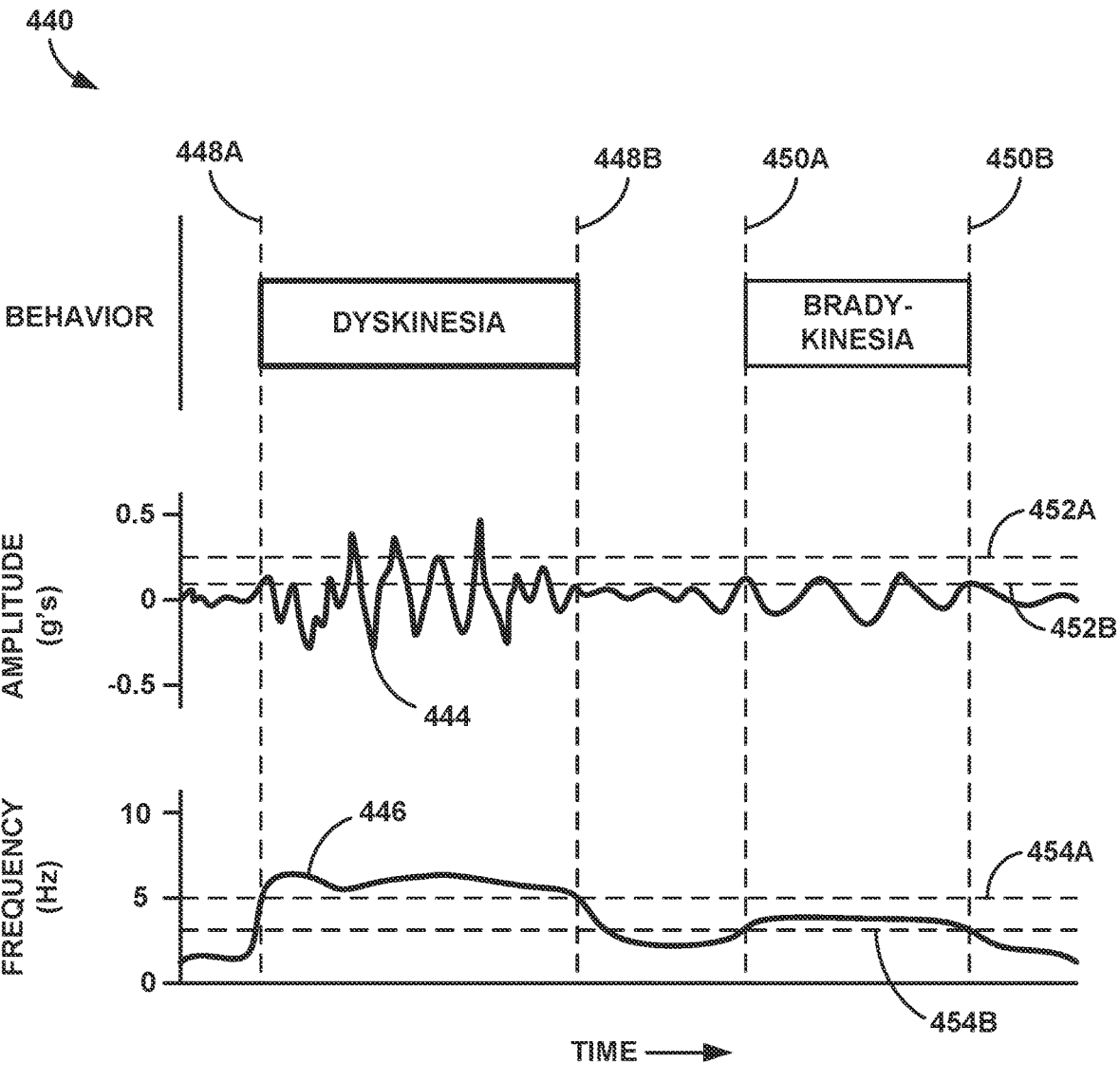
FIG. 28 is a graph illustrating a correlation of determined patient movement from video information to patient parameters sensed during the same period of time during which the video information was captured.

FIG. 28 is a graph illustrating a correlation of determined patient movement from video information to patient parameters sensed during the same period of time during which video information 50 was captured. As shown in graph 440, signal 442 may be a calculated velocity of an anatomical region over time and a plurality of captured video frames. Networked server 44, for example, may identify which patient behaviors occurred over time when the video information was captured, as described herein. In this manner, networked server 44 may be configured to calculate, from video information 50 captured during a period of time, one or more movement parameters of patient 12C and identify, based on the one or more movement parameters, each of one of a plurality of patient behaviors that occurred during the period of time. As shown in FIG. 28, networked server 44 has identified dyskinesia as occurring between times 448A and 448B and bradykinesia as occurring between times 450A and 450B.

During the same period of time in which video information 50 was captured of patient 12C, for example, values of patient parameters were obtained that also reflect some aspect of the patient behavior. In the example of FIG. 28, accelerations from an accelerometer were obtained and processed to calculate an acceleration signal 444 and a frequency signal 446. Frequency signal 446 may be indicative of the frequency with which the accelerations oscillated back and forth due to patient movement. Networked server 44 may correlate acceleration signal 444 and frequency signal 446 to the identified patient behaviors. This process may be referred to as calibrating the patient parameters to respective patient behaviors.

For example, networked server 44 may determine thresholds at which the values of each patient parameter are indicative of the respective behaviors. Acceleration signal 444 is shown in "g's" or the acceleration due to gravity. Based on the magnitude of acceleration signal 444, networked server 44 may determine threshold 452A as indicative of dyskinesia because acceleration signal 444 included magnitudes above threshold 452A between times 448A and 448B. Based on the magnitude of acceleration signal 444, networked server 44 may determine threshold 452B as indicative of bradykinesia because acceleration signal 444 included magnitudes above threshold 452B between times 450A and 450B. Networked server 44 may also set threshold 452A as a maximum threshold for bradykinesia such as amplitudes between thresholds 452A and 452B are interpreted as indicative of bradykinesia.

Frequency signal 446 is shown in Hz over time. Based on the magnitude of frequency signal 446, networked server 44 may determine threshold 454A as indicative of dyskinesia because frequency signal 446 included magnitudes above threshold 454A between times 448A and 448B. Based on the magnitude of frequency signal 446, networked server 44 may determine threshold 454B as indicative of bradykinesia because frequency signal 446 included frequencies above threshold 454B between times 450A and 450B. Networked server 44 may also set threshold 454A as a maximum threshold for bradykinesia such as frequencies between thresholds 454A and 454B are interpreted as indicative of bradykinesia.

The example of FIG. 28 is just one technique to calibrate values of patient parameters with identified patient behaviors from video information 50. In some examples, the thresholds may be based on a change in patient parameter value instead of an absolute value of the patient parameter. In other examples, thresholds may not be used. Instead, actual values of the patient parameter value may be matched to each type of patient behavior. In some examples, networked server 44 may be configured to correlate sensed parameter values obtained prior to the patient behavior being identified in time to the patient behavior. In some situations, a patient parameter value may "lead" or be indicative of the patient behavior. In this manner, one or more patient parameters may be predictive of observable patient behaviors.

FIG. 29 is a flow diagram illustrating an example process for associating sensed patient parameter values with patient behavior identified from video information 50. Although FIG. 29 will be described with respect to processors 80 of networked server 44 and processor 350 of IMD 324, other devices or combination of devices may perform similar functions such as calibrating patient parameters to identified patient behaviors from video information.

As shown in FIG. 29, processors 80 may obtain video information 50 of patient 12A captured by camera 26 during a period of time (460). Processors 80 then identify any patient behavior that occurred during the period of time from the video frames of video information 50 (462). Processors 80 also obtain sensor data from a sensor (e.g., sensor 359) generated for a patient parameter and during the time period of the video information (464). Processors 80 may then select patient parameter values from the sensor data that are indicative, or representative, of the identified patient behavior from the video information (466). Processors 80 may then associate the identified patient behavior and corresponding therapy parameter values with the selected patient parameter values (468). This correlation (or calibration) may, in some examples, include the determination of one or more thresholds or ranges within which the representative patient parameter values will occur.

Once the correlations have been made, networked server 44 may store the correlations in repository 46 and transmit the correlations to programmer 24 and/or IMD 324 for use as feedback to control therapy. Processor 350 of IMD 324 may then monitor the subsequent patient parameter data from the sensor (470). If processor 350 does not detect a patient parameter value indicative of any patient behavior ("NO" branch of block 472), processor 350 may continue to monitor the data from the sensor. If processor 350 detects a patient parameter value indicative of a behavior ("YES" branch of block 472), processor 350 may select the one or more therapy parameters associated with the detected patient parameter values and control therapy delivery using the selected therapy parameters (474).

The example of FIG. 29 may be used for monitoring multiple different patient parameters as well. For example, processor 350 may monitor the values of respective patient parameters and select the therapy parameters associated with the patient parameter values associated with the values that are sensed. In some examples, if multiple patient parameter values are indicative of a particular behavior, each of the patient parameters might need to be indicative of the same behavior before processor 350 will select the associated therapy parameters. Although IMD 324 is described as monitoring the patient parameter values, programmer 24, networked server 44, and/or another computing device may monitor one or more patient parameters.

Figure 30:
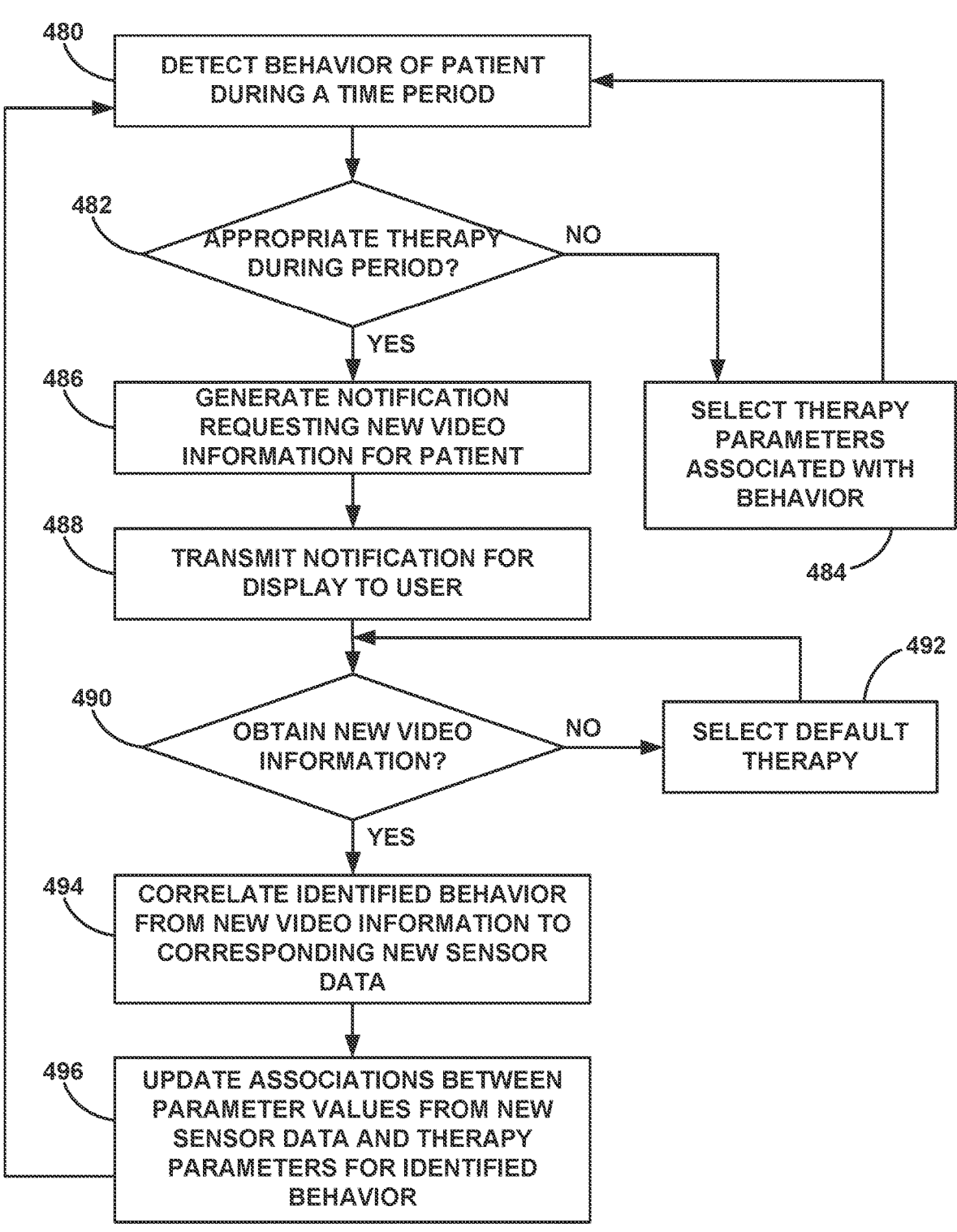
FIG. 30 is a flow diagram illustrating an example process for requesting new video information and updating the associations between sensed patient parameter values and patient behaviors identified from the new video information.

FIG. 30 is a flow diagram illustrating an example process for requesting new video information and updating the associations between sensed patient parameter values and patient behaviors identified from the new video information. At some point during therapy, one or more therapies may no longer be as effective as they once were. In addition, patient disease progression may cause changes to the severity, duration, or type of exhibited behavior. Therefore, it may be desirable to capture new video information and update the correlations between patient behaviors and sensed patient parameter values. Although FIG. 30 will be described with respect to processors 80 of networked server 44 and processor 350 of IMD 324, other devices or combination of devices may perform similar functions such as calibrating patient parameters to identified patient behaviors from video information.

Processor 350 of IMD 324 may detect a patient behavior from sensor data during a time period (480). If the appropriate therapy for the behavior was not being delivered when the behavior was detected ("NO" branch of block 482), processor 350 may select therapy parameters associated with the behavior (484) and continue to detect patient behavior (480). If the appropriate therapy for the detected behavior was being delivered when the behavior was detected ("YES" branch of block 482), processor 350 may generate a notification requesting new video information capturing motion of patient 12A (486). Processor 350 may transmit the notification for display to a user (e.g., patient 12A or clinician 22) such that video information can be captured (488). The user or clinician may then arrange for new video information to be captured of patient 12A. If camera 26 is already in place to capture video, processor 350 may transmit the notification to computing device 30 for initiation of video capture.

If networked server 44 has not received new video information or updated associations between the patient parameter values and the therapy parameters ("NO" branch of block 490), processor 350 may be instructed to select a default therapy (492) and wait for updated instructions. The default therapy may be a known acceptable therapy, a minimal therapy based on the last identified behavior, or even a therapy selected by the patient or clinician. If networked server 44 receives new video information captured from patient 12A ("YES" branch of block 490), networked server 44 may analyze the new video information to identify any patient behaviors, obtain new sensor data, and correlate the patient parameter values of the sensor data to the newly identified patient behaviors (494). Networked server 44 may then update the associations between the patient parameter values of the new sensor data and the therapy parameter values for the identified patient behaviors (496).

Although networked server 44 may initially identify patient behaviors by using only video information, networked server 44 may alternatively obtain patient parameter data from various other sources (e.g., any sensors described herein) and determine one or more patient behaviors from a combination of the video information and the obtained patient parameter data. As one example, networked server 44 may use video information in conjunction with patient parameter data from accelerometers, gyroscopes or GPS devices to distinguish between tremor during patient rest, tremor during patient action, or tremor while a patient is attempting to hold a static posture. The patient parameter data used in the initial behavior identification process may then also be associated with the identified behavior for use in detecting subsequent instances of the behavior. A determined behavior may then be used to selecting corresponding therapy parameters as discussed herein. Thus, in some examples, networked server 44 may be configured to identify one or more patient behaviors from video information and information obtained from other sources, such as one or more sensors from which patient parameters are derived. In a similar manner, networked server 44 (or any other similarly configured device) may detect a previously-identified patient behavior by monitoring both patient parameter data as well as video data. For instance, a patient may have one or more video systems installed in his or her home. While the patient remains in this environment, networked server 44 may obtain video information from the one or more video systems and obtain patient parameter values detected by one or more non-video sensors (e.g., accelerometers, pressure sensors, etc.) in an on-going or intermittent basis to subsequently determine one or more behaviors of the patient. For example, a video system may transfer video information wirelessly, either in raw format or in a processed format, to IMD 324, 344, programmer 24, and/or networked server 44 for use in determining the patient behavior. The one or more patient parameters may be combined with the video information to determine the patient behavior, or the patient parameters may be used to confirm a patient behavior determined from the video information. Any devices described herein may, in some examples, adjust therapy from the determined patient behavior As discussed herein, networked server 44, IMD 324, or programmer 24, for example, may periodically obtain and/or request new video information from one or more video systems. The new video information may then be used to re-identify patient behaviors following the initial identification, or calibration, of the patient behaviors. Subsequently determined patient behaviors (e.g., re-identified patient behaviors) may be used by one or more systems to track changes in one or more symptoms and/or disease progression. Additionally, the determined patient behaviors may be used to adjust therapy based on the stage of the disease. In some cases, networked device 44 (or another device such as programmer 24) may generate a notification based on one of more determined patient behaviors. The notification may instruct the patient to take one or more actions, such as take a medication, perform an activity, call a clinician, or schedule an appointment with a clinician. Networked server 44 may also transmit the notification to the clinician or otherwise follow up with the patient regarding the determined patient behavior. In this manner, determination of patient behaviors from video information (and patient parameters in some examples) can be used by a device or system to identify symptom or disease trends for the patient and take other appropriate actions (e.g., adjust therapy or provide instructions to a patient) in response to various behaviors that may indicate one or more disease states.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to server 44 and programmer 24, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between programmer 24 and server 44. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:
1. A system comprising:
a memory; and
processing circuitry in communication with the memory, the processing circuitry configured to:
  obtain video information of patient motion captured over a period of time for a patient, wherein the video information comprises a plurality of frames;
  receive, with respect to one frame of the plurality of frames, a selection of a sample area representative of an anatomical region;
  calculate, for each frame of other frames of the plurality of frames, one or more movement parameters corresponding to the anatomical region during the period of time,
    wherein the one or more movement parameters comprise at least one of:
      one or more time parameter values corresponding to the motion of the anatomical region over the period of time; or
      one or more frequency domain parameter values corresponding to the motion of the anatomical region over the period of time;
    wherein to calculate the one or more movement parameters, the processing circuitry is configured to, for each frame of the other frames of the plurality of frames:
      identify one or more motion centers corresponding to the anatomical region;
      for each of the one or more motion centers, determine a corresponding motion center from a prior frame;
      for each of the one or more motion centers, calculate a velocity for the respective frame;
      for each of the one or more motion centers, calculate a velocity change and a velocity angle between the motion center and the corresponding motion center from the prior frame; and
      for each of the one or more motion centers, store the velocity, the velocity change, and the velocity angle as respective parameter values; and
  determine, based on at least one of the velocity, the velocity change, or the velocity angle, that bradykinesia occurred during the period of time for the patient.

2. The system of claim 1, wherein to calculate the one or more movement parameters, the processing circuitry is configured to, for each frame of the other frames of the plurality of frames:
  determine a center of a corresponding area representing the anatomical region;
  calculate, based on movement of the center of the corresponding area from a prior frame of the plurality of frames, a velocity of the anatomical region as a first parameter value; and
  calculate a ratio of a distance the center of the corresponding area moved from the prior frame to a distance of the center of the anatomical region moved during the period of time, wherein the ratio is a second parameter value.

3. The system of claim 2, wherein the processing circuitry is further configured to:
  compare, for each frame of the other frames of the plurality of frames, the second parameter value to a tortuosity threshold;
  generate, based on the comparison for each frame of the other frames of the plurality of frames, a frequency for which the second parameter value exceeded the tortuosity threshold during the period of time;
  generate, for each frame of the other frames of the plurality of frames, an uncertainty of the corresponding area representing the anatomical region;
  determine that the frequency is greater than a tortuosity occurrence threshold and the uncertainty is less than an uncertainty occurrence threshold and
  in response to the determination, identify dyskinesia for the anatomical region during the period of time.

4. The system of claim 1, wherein the processing circuitry is further configured to:
  determine, for each frame of the other frames of the plurality of frames, that at least one of one or more motion centers within the respective frame have a velocity greater than a velocity threshold, a velocity change less than a velocity change threshold, and a velocity angle less than a velocity angle threshold;
  indicate, based on the determination, that bradykinesia occurred in the respective frame;
  determine that bradykinesia occurred in more than a threshold number of frames; and
  determine that an uncertainty of the respective areas corresponding to the anatomical region occurred at a frequency less than an uncertainty occurrence threshold,
  wherein the processing circuitry is configured to, in response to determining that bradykinesia occurred in more than a threshold number of frames and determining that the uncertainty occurred at the frequency less than the uncertainty occurrence threshold, identify bradykinesia for the anatomical region during the period of time.

5. The system of claim 1, wherein the processing circuitry is further configured to:
  determine, for each frame of the other frames of the plurality of frames, that at least one of the one or more motion centers within the respective frame have a velocity greater than a velocity threshold, a velocity change greater than a velocity change threshold, and a velocity angle greater than a velocity angle threshold;
  indicate, based on the determination, that dyskinesia occurred in the respective frame;
  determine that dyskinesia occurred in more than a threshold number of frames;

determine that an uncertainty of the respective areas corresponding to the anatomical region occurred at a frequency less than an uncertainty occurrence threshold and in response to determining that dyskinesia occurred in more than a threshold number of frames and determining that the uncertainty occurred at the frequency less than the uncertainty occurrence threshold, identify dyskinesia for the anatomical region during the period of time.

6. The system of claim 1, wherein to identify the one or more motion centers, the processing circuitry is configured to:

generate raw motion pixels for each frame of the other frames of the plurality of frames, wherein the raw motion pixels are a difference between pixels of each frame of the other frames of the plurality of frames and its respective prior frame;

for each raw motion pixel of each frame of the other frames of the plurality of frames, determine a gray intensity value;

for each raw motion pixel of each frame of the other frames of the plurality of frames, compare the respective gray intensity value to a gray intensity threshold;

identify raw motion pixels greater than the gray intensity threshold as intensity motion pixels;

generate a motion track map comprising the intensity motion pixels of each frame of the other frames of the plurality of frames;

for each of the intensity motion pixels of each frame of the other frames of the plurality of frames, determine the intensity motion pixels occurring in a continuous or an adjacent area of a subsequent frame;

identify the determined intensity motion pixels as real motion pixels representative of movement of the anatomical region;

update the motion track map to include only the identified real motion pixels;

for the identified real motion pixels each frame of the other frames of the plurality of frames, combine neighboring real motion pixels into respective motion groups of each frame of the other frames of the plurality of frames; and calculate a motion center for each of the respective motion groups.

7. The system of claim 1, wherein to calculate the one or more movement parameters corresponding to the anatomical region during the period of time, the processing circuitry is configured to, for each frame of at least a subset of frames of the plurality of frames:

apply a fast Fourier transform to the real motion pixels of the frame to generate amplitude spectrums in a frequency domain;

select three frequencies having the highest amplitude spectrums in the frequency domain;

select, based on the comparison, one of the three frequencies that falls within a predetermined range of frequencies and has the highest amplitude spectrum of the three frequencies; and store the selected one of the three frequencies as a detected frequency for the respective frame, wherein the detected frequency is one of the one or more frequency domain parameter values.

8. The system of claim 7, wherein the processing circuitry is configured to:

determine an occurrence with which the subset of frames of the plurality of frames comprises the detected frequency;

determine that the occurrence is greater than an occurrence threshold;

determine that an uncertainty of the respective areas corresponding to the anatomical region occurred at a frequency less than an uncertainty occurrence threshold; and in response to determining that the occurrence is greater than the occurrence threshold and determining that the uncertainty occurred at the frequency less than the uncertainty occurrence threshold, identify tremor for the anatomical region during the second period of time.

9. The system of claim 1, wherein the processing circuitry is further configured to:

compare the sample area to a corresponding area in a subsequent frame to the one frame of the plurality of frames;

generate a correlation coefficient between the sample area and the corresponding area;

determine that the correlation coefficient is greater than a correlation threshold; and identify, by the one or more processors, the corresponding area in the subsequent frame as the anatomical region represented by the sample area.

* * * * *